US008263547B2

(12) United States Patent
Tsai et al.

(10) Patent No.: US 8,263,547 B2
(45) Date of Patent: Sep. 11, 2012

(54) DISC-1 PATHWAY ACTIVATORS IN THE CONTROL OF NEUROGENESIS

(75) Inventors: Li-Huei Tsai, Cambridge, MA (US); Yingwei Mao, Arlington, MA (US); Jon Madison, Newton, MA (US); Stephen J. Haggarty, Dorchester, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 315 days.

(21) Appl. No.: 12/474,229

(22) Filed: May 28, 2009

(65) Prior Publication Data

US 2010/0015130 A1    Jan. 21, 2010

Related U.S. Application Data

(60) Provisional application No. 61/155,973, filed on Feb. 27, 2009, provisional application No. 61/130,071, filed on May 28, 2008.

(51) Int. Cl.
*A61K 38/00* (2006.01)
*C07K 5/00* (2006.01)
*G01N 33/53* (2006.01)
*C12Q 1/00* (2006.01)

(52) U.S. Cl. .......... 514/1.1; 530/300; 530/839; 435/7.1; 435/4

(58) Field of Classification Search .......... None
See application file for complete search history.

(56) References Cited

U.S. PATENT DOCUMENTS

| | | | |
|---|---|---|---|
| 6,323,029 | B1 | 11/2001 | Butler |
| 6,573,293 | B2 | 6/2003 | Tang et al. |
| 6,800,632 | B2 | 10/2004 | Nuss et al. |
| 7,037,918 | B2 | 5/2006 | Nuss et al. |
| 7,262,336 | B2 | 8/2007 | Young et al. |
| 7,304,071 | B2 | 12/2007 | Cochran et al. |
| 2001/0044436 | A1 | 11/2001 | Nuss |
| 2003/0054345 | A1 | 3/2003 | Meyer et al. |
| 2003/0163836 | A1 | 8/2003 | Garofalo et al. |
| 2003/0194750 | A1 | 10/2003 | Li |
| 2003/0211608 | A1 | 11/2003 | Butler |
| 2003/0216574 | A1 | 11/2003 | Nuss |
| 2004/0039007 | A1 | 2/2004 | Forster |
| 2004/0077591 | A1 | 4/2004 | Dangond |
| 2004/0087657 | A1 | 5/2004 | Richon et al. |
| 2004/0110837 | A1 | 6/2004 | Phiel et al. |
| 2005/0037992 | A1 | 2/2005 | Lyons et al. |
| 2005/0054663 | A1 | 3/2005 | Bennett et al. |
| 2005/0054850 | A1 | 3/2005 | Wu et al. |
| 2005/0171112 | A1 | 8/2005 | Schulz |
| 2005/0210536 | A1 | 9/2005 | Ginns et al. |
| 2005/0255500 | A1 | 11/2005 | Sawa |
| 2005/0272800 | A1 | 12/2005 | Segelstein et al. |
| 2006/0018921 | A1 | 1/2006 | Levenson et al. |
| 2006/0051786 | A1 | 3/2006 | Akil |
| 2006/0135408 | A1 | 6/2006 | Eldar-Finkelman |
| 2006/0135534 | A1 | 6/2006 | Nuss |
| 2006/0183747 | A1 | 8/2006 | Freyne |
| 2006/0281787 | A1 | 12/2006 | Graff |
| 2007/0078083 | A1 | 4/2007 | Barlow et al. |
| 2008/0050314 | A1 | 2/2008 | Golz et al. |
| 2008/0175924 | A1 | 7/2008 | Clelland et al. |
| 2008/0188457 | A1 | 8/2008 | Barlow et al. |
| 2008/0207594 | A1 | 8/2008 | Mussmann et al. |
| 2008/0286197 | A1 | 11/2008 | Korth et al. |
| 2008/0300205 | A1 | 12/2008 | Tsai et al. |
| 2010/0075926 | A1 | 3/2010 | Tsai et al. |
| 2011/0008468 | A1 | 1/2011 | Haggarty et al. |
| 2011/0009475 | A1 | 1/2011 | Fischer et al. |
| 2011/0224303 | A1 | 9/2011 | Tsai et al. |

FOREIGN PATENT DOCUMENTS

| | | | |
|---|---|---|---|
| WO | WO 0140301 | * | 6/2001 |
| WO | WO 02/058637 | | 8/2002 |
| WO | WO 03/102587 | | 12/2003 |
| WO | WO 2004/071269 | | 8/2004 |
| WO | WO 2007/048802 | | 5/2007 |
| WO | WO 2008/144507 | | 11/2008 |

OTHER PUBLICATIONS

Beaulieu Jean-Martin et al. 2008, a β-arrestin 2 Signaling Complex Mediates Lithium Action on Behavior, *Cell* 132, p. 125-136.
Cadigan K. & Liu Y., 2005, Wnt signaling: complexity at the surface, *Journal of Cell Science*, 119, p. 395-402.
Carter, C.J., 2007, Multiple genes and factors associated with bipolar disorder converge on growth factor and stress activated kinase pathways controlling translation initiation; implications for oligodendrocyte viability, *Neurochem Int.*, 50(3): 461-90.
Emamian E. et al., 2004, Convergent evidence for impaired AKT1-GSK3β signaling in schizophrenia, *Nature Genetics*, vol. 36, No. 2, p. 131-137.
Guan J-S et al., 2009, HDAC2 negatively regulates memory formation and synaptic plasticity, *Nature*, 459, p. 1-9.
Ikeda, M. et al., 2005, No association of GSK3beta gene (GSK3B) with Japanese schizophrenia, *Am J Med Genet B Neuropsychiatr Genet*, 134B(1): 90-2.
Ikeda, M. et al., 2007, Possible association of β-arrestin 2 gene with methamphetamine use disorder, but not schizophrenia, *Genes, Brain and Behavior*, 6: 107-112.
Lie, D-C et al., 2005, Wnt signaling regulates adult hippocampal neurogenesis, *Nature*, vol. 437, p. 1370-1375.
Lovestone, S. et al., 2007, Schizophrenia as a GSK-3 dysregulation disorder, *Trends in Neurosciences* Vo. 30, No. 4, pp. 142-149.
Mao, Y. et al., 2009, Disrupted in Schizophrenia 1 Regulates Neuronal Progenitor Proliferation via Modulation of GSK3β/β-Catenin Signaling, *Cell*, 136, 1017-1031.

(Continued)

*Primary Examiner* — Daniel E Kolker
*Assistant Examiner* — Aditi Dutt
(74) *Attorney, Agent, or Firm* — Wolf, Greenfield & Sacks, P.C.

(57) ABSTRACT

The invention relates to methods of treating neurological disorders in a subject, by activating a DISC1 pathway. Methods of promoting neurogenesis in adult neural progenitor cells, enhancing nerve generation and treating GSK3 disorders as well as related compositions are also provided.

9 Claims, 43 Drawing Sheets

OTHER PUBLICATIONS

Montgomery R. et al., 2009, Histone deacetylases 1 and 2 control the progression of neural precursors to neurons during brain development, *PNAS*, vol. 106, No. 19, p. 7876-7881.

Mussmann R. et al., 2007, Inhibition of GSK3 Promotes Replication and Survival of Pancreatic Beta Cells, *Journal of Biological Chemistry*, Vo. 282, No. 16, pp. 12030-12037.

Ozeki Y. et al., Disrupted-in-Schizophrenia-1 (DISC-1): Mutant truncation prevents binding to NudE-like (NUDEL) and inhibits neurite outgrowth, http:/www.pnas.org/content/100/1/289.full, downloaded on May 27, 2009, PNAS 10 0, 289-294 , 2003.

Saha R.N. & Pahan K., 2006, HATs and HDACs in neurodegeneration: a tale of disconcerted acetylation homeostasis; *Cell Death Differ*, 13(4): 539-550.

Singh, K., Analysis of DISC1 mutations in wnt signaling and neural progenitor cell fate, Picower Institute for Learning and Memory, 2008, http://www.hfsp.org/Awardees/abstract.php?id=79&year=2008&kind=LT, downloaded May 16, 2008.

Tsai, S-J et al., 2008, Glycogen synthase kinase-3β gene is associated with antidepressant treatment response in Chinese major depressive disorder, *The Pharmacogenomics Journal*, 8, p. 384-390.

Wnt signaling pathway, Wikipedia, http://en.wikipedia.org/wiki/Wnt_signaling_pathway, downloaded May 16, 2008.

Wood M. A. et al., Transgenic mice expressing a truncated form of CREB-binding protein (CBP) exhibit deficits in hippocampal synaptic plasticity and memory storage, *Learning & Memory*, 12:111-119, 2005.

[No Author Listed] Compound data sheet. CID 6610063 (Jun. 5, 2006), CID 6610127 (Jun. 5, 2006), CID 6610019 (Jun. 5, 2006), CID 6610021(Jun. 5, 2006), CID 6610023 (Jun. 5, 2006), CID 6610025 (Jun. 5, 2006), CID 6610029 (Jun. 5, 2006), CID 6610049 (Jun. 5, 2006), CID 6610051 (Jun. 5, 2006), CID 6610053 (Jun. 5, 2006), CID 6610059 (Jun. 5, 2006), CID 6610061 (Jun. 5, 2006), CID 6610079 (Jun. 5, 2006), CID 6610083 (Jun. 5, 2006), CID 6610084 (Jun. 5, 2006), CID 6610087 (Jun. 5, 2006), CID 10508842 (Oct. 25, 2006), CID 10770612 (Oct. 26, 2006), CID 10811049 (Oct. 26, 2006), CID 11545870 (Oct. 26, 2006), CID 11567962 (Oct. 25, 2006), CID 11604060 (Oct. 27, 2006), CID 11618806 (Oct. 27, 2006), CID 11626825 (Oct. 27, 2006), CID 11640236 (Oct. 27, 2006), CID 11647651 (Oct. 27, 2006), CID 11696973 (Oct. 27, 2006), CID 11734797 (Oct. 27, 2006), CID 11954943 (Nov. 29, 2006), CID 23629586 (Dec. 26, 2007), CID 24770385 (Apr. 28, 2008), CID 24770453 (Apr. 28, 2008).

[No Author Listed] Compound data sheet. CID 3519450 (Sep. 8, 2005), CID 3552796 (Sep. 9, 2005), CID 4428949 (Sep. 15, 2005), CID 5150838 (Sep. 26, 2005), CID 16187129 (Jul. 5, 2007) CID 16187152 (Jul. 5, 2007), CID 16187170 (Jul. 5, 2007), CID 23789436 (Feb. 20, 2008), CID 23818441 (Feb. 20, 2008), CID 23958527 (Feb. 21, 2008).

[No Author Listed] Compound data sheet. CID 23919061 (Feb. 20, 2008), CID 24086260 (Feb. 21, 2008).

Genbank Submission; NIH/NCBI, Accession No. AF222980; GI:8163868;Millar et al.; Jun. 2, 2000.

Genbank Submission; NIH/NCBI, Accession No. XM_029918;NCBI Annotation Project; Dec. 10, 2001.

Genbank Submission; NIH/NCBI, Accession No. L33801; Stambolic et al.; May 16, 1995.

Aberle et al., Beta-catenin is a target for the ubiquitin-proteasome pathway. EMBO J. Jul. 1, 1997;16(13):3797-804.

Adachi et al., Beta-catenin signaling promotes proliferation of progenitor cells in the adult mouse subventricular zone. Stem Cells. Nov. 2007;25(11):2827-36. Epub Aug. 2, 2007.

Arnold et al., Neurodevelopmental abnormalities in schizophrenia: insights from neuropathology. Dev Psychopathol. 1999 Summer;11(3):439-56.

Bax et al., The structure of phosphorylated GSK-3beta complexed with a peptide, FRA Ttide, that inhibits beta-catenin phosphorylation. Structure. Dec. 2001;9(12):1143-52.

Beaulieu et al., Lithium antagonizes dopamine-dependent behaviors mediated by an AKT/glycogen synthase kinase 3 signaling cascade. Proc Natl Acad Sci U S A. Apr. 6, 2004;101(14):5099-104. Epub Mar. 24, 2004.

Beaulieu et al., An Akt/beta-arrestin 2/PP2A signaling complex mediates dopaminergic neurotransmission and behavior. Cell. Jul. 29, 2005;122(2):261-73.

Blackwood et al., Schizophrenia and affective disorders—cosegregation with a translocation at chromosome 1q42 that directly disrupts brain-expressed genes: clinical and P300 findings in a family. Am J Hum Genet. Aug. 2001;69(2):428-33. Epub Jul. 6, 2001.

Bregman et al., An organometallic inhibitor for glycogen synthase kinase 3. J Am Chem Soc. Oct. 27, 2004;126(42):13594-5.

Catapano et al., Kinases as drug targets in the treatment of bipolar disorder. Drug Discov Today. Apr. 2008; 13(7-8):295-302. Epub Apr. 3, 2008.

Chen et al., The mood-stabilizing agent valproate inhibits the activity of glycogen synthase kinase-3. J Neurochem. Mar. 1999;72(3):1327-30.

Chenn et al., Regulation of cerebral cortical size by control of cell cycle exit in neural precursors. Science. Jul. 19, 2002;297(5580):365-9.

Chubb et al., The DISC locus in Psychiatric illness. Mol Psychiatry. Jan. 2008;13(1):36-64. Epub Oct. 2, 2007.

Clapcote et al., Behavioral phenotypes of Disclmissense mutations in mice. Neuron. May 3, 2007;54(3):387-402.

Cohen et al., GSK3 inhibitors: development and therapeutic potential. Nat Rev Drug Discov. Jun. 2004;3(6):479-87.

Cross et al., Inhibition of glycogen synthase kinase-3 by insulin mediated by protein kinase B. Nature. Dec. 21-28, 1995;378(6559):785-9.

Duan et al., Disrupted-In-Schizophrenia 1 regulates integration of newly generated neurons in the adult brain. Cell. Sep. 21, 2007;130(6):1146-58. Epub Sep. 6, 2007.

Einat et al., Protein kinase C inhibition by tamoxifen antagonizes manic-like behavior in rats: implications for the development of novel therapeutics for bipolar disorder. Neuropsychobiology. 2007;55(3-4):123-31. Epub Jul. 18, 2007.

Flagstad et al., Cognitive deficits caused by late gestational disruption of neurogenesis in rats: a preclinical model of schizophrenia. Neuropsychopharmacology. Feb. 2005;30(2):250-60.

Flagstad et al., Disruption of neurogenesis on gestational day 17 in the rat causes behavioral changes relevant to positive and negative schizophrenia symptoms and alters amphetamine-induced dopamine release in nucleus accumbens. Neuropsychopharmacology. Nov. 2004;29(11):2052-64.

Gould et al., Beta-catenin overexpression in the mouse brain phenocopies lithium-sensitive behaviors. Neuropsychopharmacology. Oct. 2007;32(10):2173-83. Epub Feb. 14, 2007.

Gould et al., Effects of a glycogen synthase kinase-3 inhibitor, lithium, in adenomatous polyposis coli mutant mice. Pharmacol Res. Jul. 2003;48(1):49-53.

Gould et al., Emerging experimental therapeutics for bipolar disorder: insights from the molecular and cellular actions of current mood stabilizers. Mol Psychiatry. Aug. 2004;9(8):734-55.

Gould et al., Glycogen synthase kinase-3: a putative molecular target for lithium mimetic drugs. Neuropsychopharmacology. Jul. 2005;30(7):1223-37.

Gould et al., Glycogen synthase kinase-3: a target for novel bipolar disorder treatments. J Clin Psychiatry. Jan. 2004;65(1):10-21.

Gould et al., In vivo evidence in the brain for lithium inhibition of glycogen synthase kinase-3. Neuropsychopharmacology. Jan. 2004;29(1):32-8.

Gould et al., Signaling networks in the pathophysiology and treatment of mood disorders. J Psychosom Res. Aug. 2002;53(2):687-97. Review.

Gould et al., Strain differences in lithium attenuation of d-amphetamine-induced hyperlocomotion: a mouse model for the genetics of clinical response to lithium. Neuropsychopharmacology. Jun. 2007;32(6):1321-33. Epub Dec. 6, 2006.

Gould et al., Targeting glycogen synthase kinase-3 in the CNS: implications for the development of new treatments for mood disorders. Curr Drug Targets. Nov. 2006;7(11):1399-409.

Gould et al., The Wnt signaling pathway in bipolar disorder. Neuroscientist. Oct. 2002;8(5):497-511.

Gregorieff et al., Wnt signaling in the intestinal epithelium: from endoderm to cancer. Genes Dev. Apr. 15, 2005;19(8):877-90.

Hedgepeth et al., Regulation of glycogen synthase kinase 3beta and downstream Wnt signaling by axin. Mol Cell Biol. Oct. 1999;19(10):7147-57.
Hikida et al., Dominant-negative DISC1 transgenic mice display schizophrenia-associated phenotypes detected by measures translatable to humans. Proc Natl Acad Sci U S A. Sep. 4, 2007;104(36):14501-6. Epub Aug. 3, 2007.
Hirabayashi et al., The Wnt/beta-catenin pathway directs neuronal differentiation of cortical neural precursor cells. Development. Jun. 2004;131(12):2791-801. Epub May 13, 2004.
Hodgkinson et al., Disrupted in schizophrenia 1 (DISC1): association with schizophrenia, schizoaffective disorder, and bipolar disorder. Am J Hum Genet. Nov. 2004;75(5):862-72. Epub Sep. 22, 2004.
Ikonomov et al., Molecular mechanisms underlying mood stabilization in manic-depressive illness: the phenotype challenge. Am J Psychiatry. Oct. 1999;156(10):1506-14.
Israsena et al., The presence of FGF2 signaling determines whether beta-catenin exerts effects on proliferation or neuronal differentiation of neural stem cells. Dev Biol. Apr. 1, 2004;268(1):220-31.
Jope et al., Glycogen synthase kinase-3 (GSK3) in psychiatric diseases and therapeutic interventions. Curr Drug Targets. Nov. 2006;7(11):1421-34.
Kaladchibachi et al., Glycogen synthase kinase 3, circadian rhythms, and bipolar disorder: a molecular link in the therapeutic action of lithium. J Circadian Rhythms. Feb. 12, 2007;5:3.
Kamiya et al., A schizophrenia-associated mutation of DISC1 perturbs cerebral cortex development. Nat Cell Biol. Dec. 2005;7(12):1167-78. Epub Nov. 20, 2005. Erratum in: Nat Cell Biol. Jan. 2006;8(1):100.
Kim et al., Receptor-dependent and tyrosine phosphatase-mediated inhibition of GSK3 regulates cell fate choice. Dev Cell. Oct. 2002;3(4):523-32.
Kilpinen et al., Association of DISC1 with autism and Asperger syndrome. Mol Psychiatry. Feb. 2008;13(2):187-96. Epub Jun. 19, 2007.
Klein et al., A molecular mechanism for the effect of lithium on development. Proc Natl Acad Sci U S A. Aug. 6, 1996;93(16):8455-9.
Koike et al., Disc1 is mutated in the 129S6/SvEv strain and modulates working memory in mice. Proc Natl Acad Sci U S A. Mar. 7, 2006;103(10):3693-7. Epub Feb. 16, 2006.
Lei et al., Wnt signaling inhibitors regulate the transcriptional response to morphogenetic Shh-Gli signaling in the neural tube. Dev Cell. Sep. 2006;11(3):325-37.
Leng et al., Synergistic neuroprotective effects of lithium and valproic acid or other histone deacetylase inhibitors in neurons: roles of glycogen synthase kinase-3 inhibition. J Neurosci. Mar. 5, 2008;28(l0):2576-88.
Li et al., Specific developmental disruption of disrupted-in-schizophrenia-1 function results in schizophrenia-related phenotypes in mice. Proc Natl Acad Sci U S A. Nov. 13, 2007;104(46):182805. Epub Nov. 2, 2007.
Lochhead et al., A chaperone-dependent GSK3beta transitional intermediate mediates activation-loop autophosphorylation. Mol Cell. Nov. 17, 2006;24(4):627-33.
Logan et al., The Wnt signaling pathway in development and disease. Annu Rev Cell Dev Biol. 2004;20:781-810.
Ma et al., Cloning and characterization of DISC1, the mouse ortholog of Disci (Disrupted-inSchizophrenia 1). Genomics. Dec. 2002;80(6):662-72.
Maeda et al., Clozapine prevents a decrease in neurogenesis in mice repeatedly treated with phencyclidine. J Pharmacol Sci. Mar. 2007;103(3):299-308. Epub Mar. 7, 2007.
Manji et al., Bipolar disorder: leads from the molecular and cellular mechanisms of action of mood stabilizers. Br J Psychiatry Suppl. Jun. 2001;41:s107-19.
Manji et al., PKC, MAP kinases and the bcl-2 family of proteins as long-term targets for mood stabilizers. Mol Psychiatry. 2002;7 Suppl 1:S46-56.
Manji et al., Signal transduction pathways. Molecular targets for lithium's actions. Arch Gen Psychiatry. Jul. 1995;52(7):531-43.
Manji et al., The underlying neurobiology of bipolar disorder. World Psychiatry. Oct. 2003;2(3):136-46.

Mao et al., Disrupted in schizophrenia 1 regulates neuronal progenitor proliferation via modulation of GSK3beta/beta-catenin signaling, Cell. Mar. 20, 2009;136(6):1017-31.
Mathew et al., Novel drugs and therapeutic targets for severe mood disorders. Neuropsychopharmacology. Aug. 2008;33(9):2080-92. Epub Jan. 2, 2008.
Meijer et al., Pharmacological inhibitors of glycogen synthase kinase 3. Trends Pharmacol Sci. Sep. 2004;25(9):471-80.
Millar et al., DISC1 and PDE4B are interacting genetic factors in schizophrenia that regulate cAMP signaling. Science. Nov. 18, 2005;310(5751):1187-91.
Millar et al., Disruption of two novel genes by a translocation co-segregating with schizophrenia. Hum Mol Genet. May 22, 2000;9(9):1415-23.
Morris et al., DISC1 (Disrupted-In-Schizophrenia 1) is a centrosome-associated protein that interacts with MAP1A, MIPT3, ATF4/5 and NUDEL: regulation and loss of interaction with mutation. Hum Mol Genet. Jul. 1, 2003 ;12(13):1591-608.
Murdoch et al., Isoform-selective susceptibility of Disci/phosphodiesterase-4 complexes to dissociation by elevated intracellular cAMP levels. J Neurosci. Aug. 29, 2007;27(35):9513-24.
Nciri et al., [Effects of low doses of Li carbonate injected into mice. Functional changes in kidney seem to be related to the oxidative status]. C R Biol. Jan. 2008;331(1):23-31. French.
Nciri et al., The effects of subchronic lithium administration in male Wistar mice on some biochemical parameters. Acta Biol Hung. Sep. 2009;60(3):273-80.
Newton et al., Neurogenic actions of atypical antipsychotic drugs and therapeutic implications. CNS Drugs. 2007;21(9):715-25.
O'Donnell et al., The behavioral actions of lithium in rodent models: leads to develop novel therapeutics. Neurosci Biobehav Rev. 2007;31(6):932-62. Epub Apr. 13, 2007.
Pletnikov et al., Inducible expression of mutant human DISC1 in mice is associated with brain and behavioral abnormalities reminiscent of schizophrenia. Mol Psychiatry. Feb. 2008;13(2):173-86, 115. Epub Sep. 11, 2007.
Quiroz et al., Molecular effects of lithium. Mol Interv. Oct. 2004;4(5):259-72.
Reif et al., Neural stem cell proliferation is decreased in schizophrenia, but not in depression. Mol Psychiatry. May 2006;11(5):514-22.
Ross et al., Neurobiology of schizophrenia. Neuron. Oct. 5, 2006;52(1):139-53.
Schüller et al., Beta-catenin function is required for cerebellar morphogenesis. Brain Res. Apr. 6, 2007;1140:161-9. Epub Jul. 7, 2006.
Schurov et al., Expression of disrupted in schizophrenia 1 (DISC1 protein in the adult and developing mouse brain indicates its role in neurodevelopment. Mol Psychiatry. Dec. 2004;9(12):1100-10.
Scott et al., Generation of tissue-specific transgenic birds with lentiviral vectors. Proc Natl Acad Sci U S A. Nov. 2005 8;102(45):16443-7. Epub Oct. 31, 2005.
Seeman, Targeting the dopamine D2 receptor in schizophrenia. Expert Opin Ther Targets. Aug. 2006;10(4):515-31.
Shinoda et al., DISC1 regulates neurotrophin-induced axon elongation via interaction with Grb2. J Neurosci. Jan. 3, 2007;27(1):4-14.
Stolovich et al., Lithium can relieve translational repression of TOP mRNAs elicited by various blocks along the cell cycle in a glycogen synthase kinase-3-and S6-kinase-independent manner. J Biol Chem. Feb. 18, 2005;280(7):5336-42.
Swatton et al., Increased MAP kinase activity in Alzheimer's and Down syndrome but not in schizophrenia human brain. Eur J Neurosci. May 2004;19(10):2711-9.
Tetsu et al., Beta-catenin regulates expression of cyclin D1 in colon carcinoma cells. Nature. Apr. 1, 1999;398(6726):422-6.
Thomas et al., A GSK3-binding peptide from Frati selectively inhibits the GSK3-catalysed phosphorylation of axin and beta-catenin. FEBS Lett. Sep. 17, 1999;458(2):247-51.
Wagman et al., Discovery and development of GSK3 inhibitors for the treatment of type 2 diabetes. Curr Pharm Des. 2004;10(10):1105-37.

Willert et al., Beta-catenin: a key mediator of Wnt signaling. Curr Opin Genet Dev. Feb. 1999;8(1):95-102.

Winston et al., The SCFbeta-TRCP-ubiquitin ligase complex associates specifically with phosphorylated destruction motifs in IkappaBalpha and beta-catenin and stimulates IkappaBalpha ubiquitination in vitro. Genes Dev. Feb. 1, 1999;13(3):270-83.

Zarate et al., Bipolar disorder: candidate drug targets. Author manuscript's title: Putative drugs and targets for bipolar disorder. Mt Sinai J Med. May-Jun. 2008;75(3):226-47.

Zarate et al., Efficacy of a protein kinase C inhibitor (tamoxifen) in the treatmentof acute mania: a pilot study. Bipolar Disord. Sep. 2007;9(6):561-70.

Zarate et al., Molecular mechanisms of bipolar disorder. Drug Disc Today: Disease Mech. 2005;2(4):435-45.

Zechner et al., Beta-Catenin signals regulate cell growth and the balance between progenitor cell expansion and differentiation in the nervous system. Dev Biol. Jun. 15, 2003;258(2):406-18.

* cited by examiner

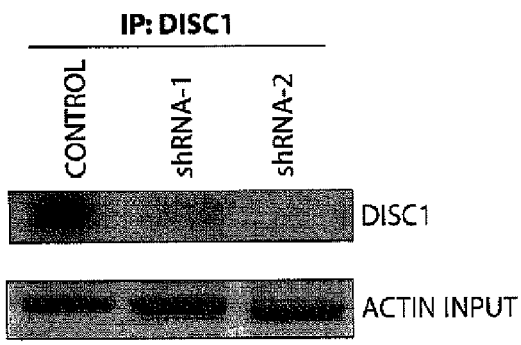
Fig. 6
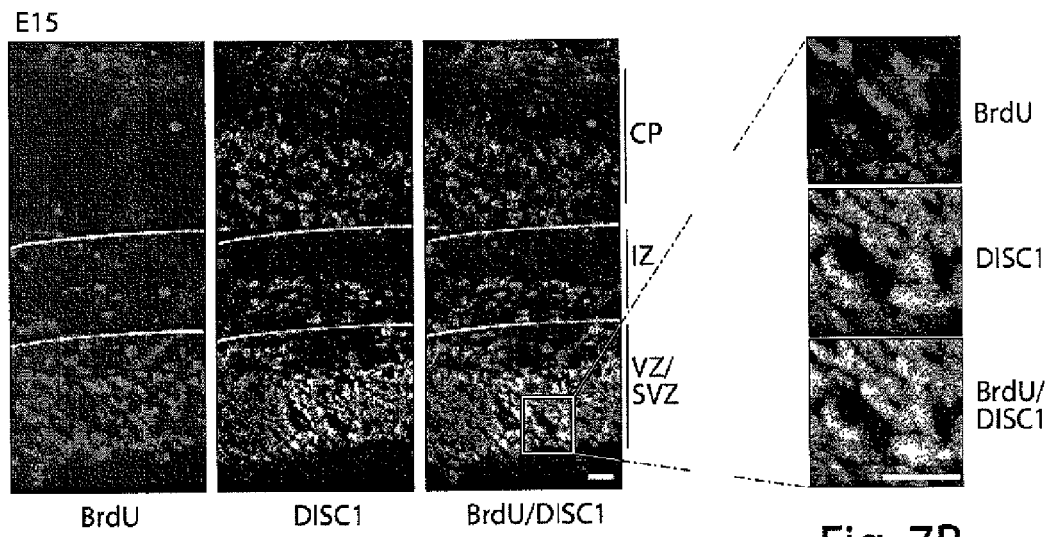
Fig. 7A
Fig. 7B
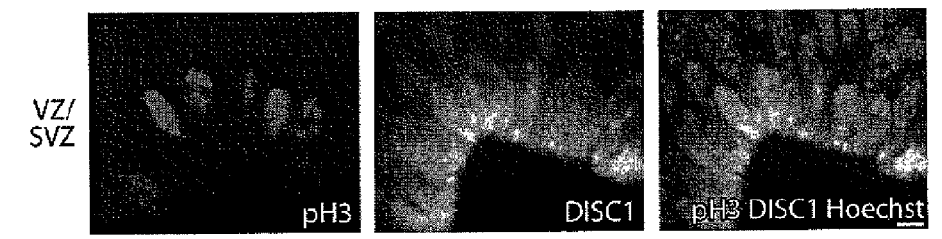
Fig. 7C

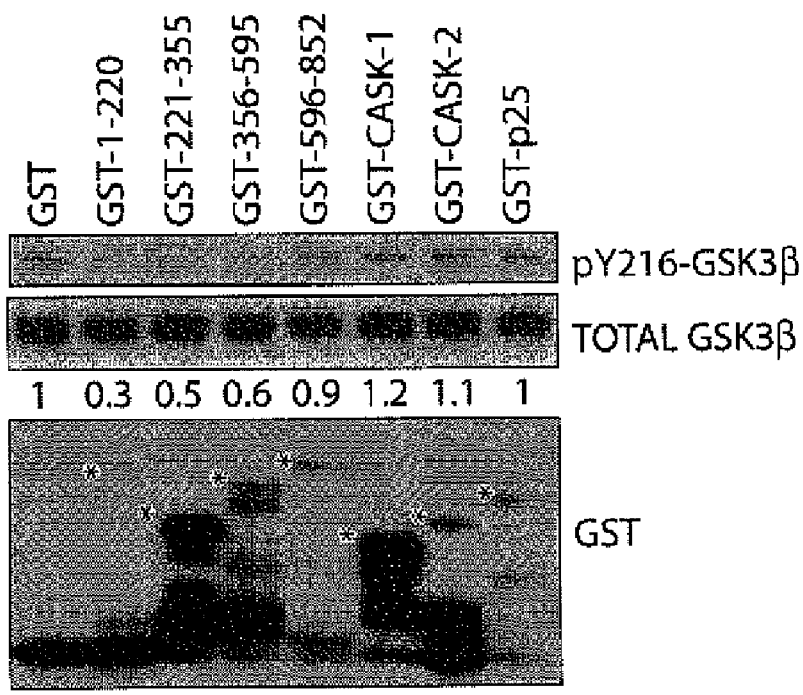
Fig. 10C
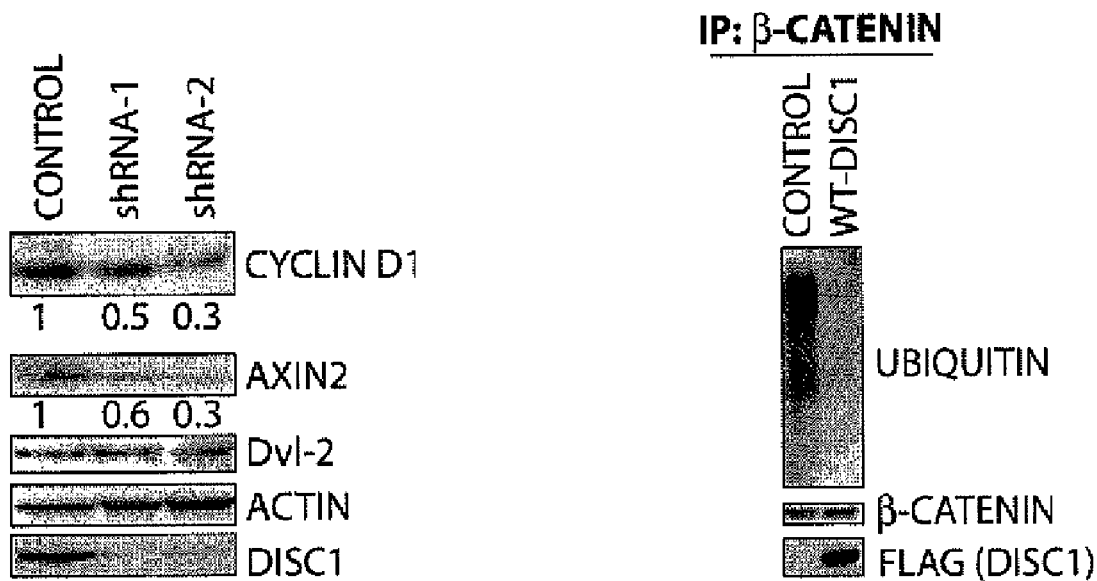
Fig. 10D
Fig. 10E

```
PEPTIDE-1
MOUSE:  40GYMRSTAGSGIGFLSPAVGMPHPSSAGLTGQQSQHSQS 78
HUMAN:  44GYMRSSTGPGIGFLSPAVGTLFRFPGGVSGEESHHSES 81

PEPTIDE-2
MOUSE:  195PADIASLPGFQDTFTSSFSFIQLSLGAAGERGEAEGCLPSREAE238
HUMAN:  193PEVPPTPPGSHSAFTSSFSFIRLSLGSAGERGEAEGCPPSREAE236
```

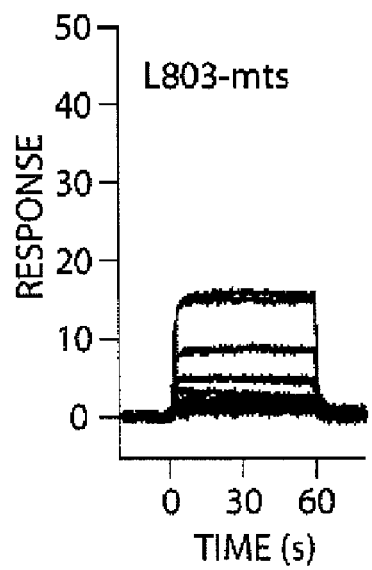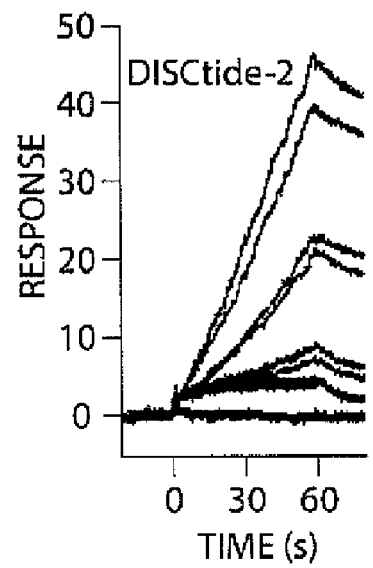
Fig. 18A
Fig. 18B
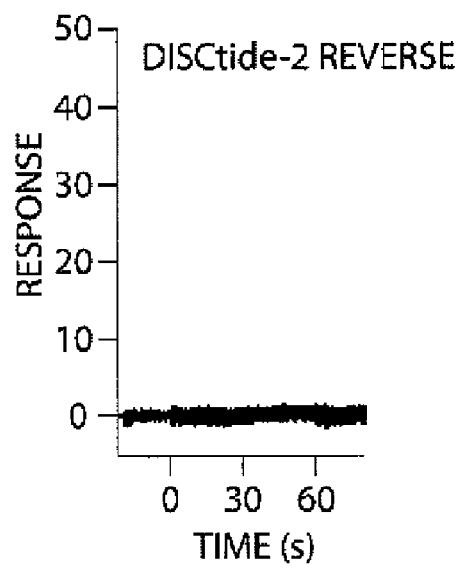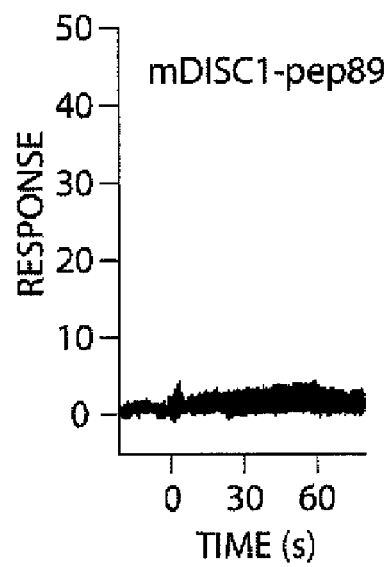
Fig. 18C
Fig. 18D

SEQUENCE LISTING

<160> NUMBER OF SEQ ID NOS: 21

<210> SEQ ID NO 1
<211> LENGTH: 38
<212> TYPE: PRT
<213> ORGANISM: Mus musculus

<400> SEQUENCE: 1

Gly Tyr Met Arg Ser Thr Ala Gly Ser Gly Ile Gly Phe Leu Ser Pro
1               5                   10                  15

Ala Val Gly Met Pro His Pro Ser Ser Ala Gly Leu Thr Gly Gln Gln
            20                  25                  30

Ser Gln His Ser Gln Ser
        35

<210> SEQ ID NO 2
<211> LENGTH: 44
<212> TYPE: PRT
<213> ORGANISM: Mus musculus

<400> SEQUENCE: 2

Pro Ala Asp Ile Ala Ser Leu Pro Gly Phe Gln Asp Thr Phe Thr Ser
1               5                   10                  15

Ser Phe Ser Phe Ile Gln Leu Ser Leu Gly Ala Ala Gly Glu Arg Gly
            20                  25                  30

Glu Ala Glu Gly Cys Leu Pro Ser Arg Glu Ala Glu
        35                  40

<210> SEQ ID NO 3

```
<211> LENGTH: 19
<212> TYPE: DNA
<213> ORGANISM: Artificial sequence
<220> FEATURE:
<223> OTHER INFORMATION: Synthetic oligonucletide

<400> SEQUENCE: 3
cggctgaaac aagagttgg                                                   19

<210> SEQ ID NO 4
<211> LENGTH: 19
<212> TYPE: DNA
<213> ORGANISM: Artificial sequence
<220> FEATURE:
<223> OTHER INFORMATION: Synthetic oligonucletide

<400> SEQUENCE: 4
ggcaaacact gtgaagtgc                                                   19

<210> SEQ ID NO 5
<211> LENGTH: 22
<212> TYPE: DNA
<213> ORGANISM: Artificial sequence
<220> FEATURE:
<223> OTHER INFORMATION: Synthetic oligonucletide

<400> SEQUENCE: 5
gcaggaggtc agcaaggcct tg                                               22

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucletide

<400> SEQUENCE: 6
ctgatattga cgggcagtat                                                  20

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucletide

<400> SEQUENCE: 7
cccaagcctt agtaaacata a                                                21

<210> SEQ ID NO 8
<211> LENGTH: 44
<212> TYPE: PRT
<213> ORGANISM: Homo sapiens

<400> SEQUENCE: 8

Pro Glu Val Pro Pro Thr Pro Pro Gly Ser His Ser Ala Phe Thr Ser
1               5                   10                  15

Ser Phe Ser Phe Ile Arg Leu Ser Leu Gly Ser Ala Gly Glu Arg Gly
            20                  25                  30

Glu Ala Glu Gly Cys Pro Pro Ser Arg Glu Ala Glu
        35                  40

<210> SEQ ID NO 9
<211> LENGTH: 15
<212> TYPE: PRT
<213> ORGANISM: Homo sapiens
```

```
<400> SEQUENCE: 9

Ser Phe Ile Arg Leu Ser Leu Gly Ser Ala Gly Glu Arg Gly Glu
1               5                   10                  15

<210> SEQ ID NO 10
<211> LENGTH: 15
<212> TYPE: PRT
<213> ORGANISM: Mus musculus

<400> SEQUENCE: 10

Ser Phe Ser Phe Ile Gln Leu Ser Leu Gly Ala Ala Gly Glu Arg
1               5                   10                  15

<210> SEQ ID NO 11
<211> LENGTH: 854
<212> TYPE: PRT
<213> ORGANISM: Homo sapiens

<400> SEQUENCE: 11

Met Pro Gly Gly Gly Pro Gln Gly Ala Pro Ala Ala Ala Gly Gly
1               5                   10                  15

Gly Val Ser His Arg Ala Gly Ser Arg Asp Cys Leu Pro Ala Ala
                20                  25                  30

Cys Phe Arg Arg Arg Leu Ala Arg Arg Pro Gly Tyr Met Arg Ser
            35                  40                  45

Ser Thr Gly Pro Gly Ile Gly Phe Leu Ser Pro Ala Val Gly Thr Leu
        50                  55                  60

Phe Arg Phe Pro Gly Gly Val Ser Gly Glu Glu Ser His His Ser Glu
65                  70                  75                  80

Ser Arg Ala Arg Gln Cys Gly Leu Asp Ser Arg Gly Leu Leu Val Arg
                85                  90                  95

Ser Pro Val Ser Lys Ser Ala Ala Ala Pro Thr Val Thr Ser Val Arg
                100                 105                 110

Gly Thr Ser Ala His Phe Gly Ile Gln Leu Arg Gly Thr Arg Leu
            115                 120                 125

Pro Asp Arg Leu Ser Trp Pro Cys Gly Pro Gly Ser Ala Gly Trp Gln
130                 135                 140

Gln Glu Phe Ala Ala Met Asp Ser Ser Glu Thr Leu Asp Ala Ser Trp
145                 150                 155                 160

Glu Ala Ala Cys Ser Asp Gly Ala Arg Arg Val Arg Ala Ala Gly Ser
                165                 170                 175

Leu Pro Ser Ala Glu Leu Ser Ser Asn Ser Cys Ser Pro Gly Cys Gly
            180                 185                 190

Pro Glu Val Pro Pro Thr Pro Gly Ser His Ser Ala Phe Thr Ser
        195                 200                 205

Ser Phe Ser Phe Ile Arg Leu Ser Leu Gly Ser Ala Gly Glu Arg Gly
    210                 215                 220

Glu Ala Glu Gly Cys Pro Pro Ser Arg Glu Ala Glu Ser His Cys Gln
225                 230                 235                 240

Ser Pro Gln Glu Met Gly Ala Lys Ala Ala Ser Leu Asp Gly Pro His
                245                 250                 255

Glu Asp Pro Arg Cys Leu Ser Gln Pro Phe Ser Leu Leu Ala Thr Arg
            260                 265                 270

Val Ser Ala Asp Leu Ala Gln Ala Ala Arg Asn Ser Ser Arg Pro Glu
        275                 280                 285

Arg Asp Met His Ser Leu Pro Asp Met Asp Pro Gly Ser Ser Ser Ser
```

-continued

```
              290                 295                 300
Leu Asp Pro Ser Leu Ala Gly Cys Gly Gly Asp Gly Ser Ser Gly Ser
305                 310                 315                 320

Gly Asp Ala His Ser Trp Asp Thr Leu Leu Arg Lys Trp Glu Pro Val
                    325                 330                 335

Leu Arg Asp Cys Leu Leu Arg Asn Arg Arg Gln Met Glu Val Ile Ser
                340                 345                 350

Leu Arg Leu Lys Leu Gln Lys Leu Gln Glu Asp Ala Val Glu Asn Asp
                355                 360                 365

Asp Tyr Asp Lys Ala Glu Thr Leu Gln Gln Arg Leu Glu Asp Leu Glu
        370                 375                 380

Gln Glu Lys Ile Ser Leu His Phe Gln Leu Pro Ser Arg Gln Pro Ala
385                 390                 395                 400

Leu Ser Ser Phe Leu Gly His Leu Ala Ala Gln Val Gln Ala Ala Leu
                405                 410                 415

Arg Arg Gly Ala Thr Gln Gln Ala Ser Gly Asp Asp Thr His Thr Pro
                420                 425                 430

Leu Arg Met Glu Pro Arg Leu Leu Glu Pro Thr Ala Gln Asp Ser Leu
                435                 440                 445

His Val Ser Ile Thr Arg Arg Asp Trp Leu Leu Gln Glu Lys Gln Gln
        450                 455                 460

Leu Gln Lys Glu Ile Glu Ala Leu Gln Ala Arg Met Phe Val Leu Glu
465                 470                 475                 480

Ala Lys Asp Gln Gln Leu Arg Arg Glu Ile Glu Glu Gln Glu Gln Gln
                485                 490                 495

Leu Gln Trp Gln Gly Cys Asp Leu Thr Pro Leu Val Gly Gln Leu Ser
                500                 505                 510

Leu Gly Gln Leu Gln Glu Val Ser Lys Ala Leu Gln Asp Thr Leu Ala
        515                 520                 525

Ser Ala Gly Gln Ile Pro Phe His Ala Glu Pro Pro Glu Thr Ile Arg
530                 535                 540

Ser Leu Gln Glu Arg Ile Lys Ser Leu Asn Leu Ser Leu Lys Glu Ile
545                 550                 555                 560

Thr Thr Lys Val Cys Met Ser Glu Lys Phe Cys Ser Thr Leu Arg Lys
                565                 570                 575

Lys Val Asn Asp Ile Glu Thr Gln Leu Pro Ala Leu Leu Glu Ala Lys
                580                 585                 590

Met His Ala Ile Ser Gly Asn His Phe Trp Thr Ala Lys Asp Leu Thr
        595                 600                 605

Glu Glu Ile Arg Ser Leu Thr Ser Glu Arg Glu Gly Leu Glu Gly Leu
610                 615                 620

Leu Ser Lys Leu Leu Val Leu Ser Ser Arg Asn Val Lys Lys Leu Gly
625                 630                 635                 640

Ser Val Lys Glu Asp Tyr Asn Arg Leu Arg Arg Glu Val Glu His Gln
                645                 650                 655

Glu Thr Ala Tyr Glu Thr Ser Val Lys Glu Asn Thr Met Lys Tyr Met
                660                 665                 670

Glu Thr Leu Lys Asn Lys Leu Cys Ser Cys Lys Cys Pro Leu Leu Gly
                675                 680                 685

Lys Val Trp Glu Ala Asp Leu Glu Ala Cys Arg Leu Leu Ile Gln Cys
                690                 695                 700

Leu Gln Leu Gln Glu Ala Arg Gly Ser Leu Ser Val Glu Asp Glu Arg
705                 710                 715                 720
```

```
Gln Met Asp Asp Leu Glu Gly Ala Ala Pro Pro Ile Pro Pro Arg Leu
                725                 730                 735

His Ser Glu Asp Lys Arg Lys Thr Pro Leu Lys Val Leu Glu Glu Trp
            740                 745                 750

Lys Thr His Leu Ile Pro Ser Leu His Cys Ala Gly Gly Glu Gln Lys
        755                 760                 765

Glu Glu Ser Tyr Ile Leu Ser Ala Gly Leu Gly Glu Lys Cys Glu Asp
    770                 775                 780

Ile Gly Lys Lys Leu Leu Tyr Leu Glu Asp Gln Leu His Thr Ala Ile
785                 790                 795                 800

His Ser His Asp Glu Asp Leu Ile Gln Ser Leu Arg Arg Glu Leu Gln
            805                 810                 815

Met Val Lys Glu Thr Leu Gln Ala Met Ile Leu Gln Leu Gln Pro Ala
        820                 825                 830

Lys Glu Ala Gly Glu Arg Glu Ala Ala Ser Cys Met Thr Ala Gly
    835                 840                 845

Val His Glu Ala Gln Ala
    850
```

<210> SEQ ID NO 12
<211> LENGTH: 6930
<212> TYPE: DNA
<213> ORGANISM: Homo sapiens

<400> SEQUENCE: 12

```
ggaaggagca ggaggcagcc caggcggagc gggaggagct ggcagcgggg cgcatgccag    60
gcggggtcc tcagggcgcc ccagccgccg ccggcggcgg cggcgtgagc caccgcgcag   120
gcagccggga ttgcttacca cctgcagcgt gctttcggag gcggcggctg gcacggaggc   180
cgggctacat gagaagctcg acagggcctg ggatcgggtt cctttcccca gcagtgggca   240
cactgttccg gttcccagga ggggtgtctg gcgaggagtc ccaccactcg gagtccaggg   300
ccagacagtg tggccttgac tcgagaggcc tcttggtccg gagccctgtt ccaagagtg   360
cagcagcccc tactgtgacc tctgtgagag gaacctcggc gcactttggg attcagctca   420
gaggtggcac cagattgcct gacaggctta gctggccgtg tggccctggg agtgctgggt   480
ggcagcaaga gtttgcagcc atggatagtt ctgagaccct ggacgccagc tgggaggcag   540
cctgcagcga tggagcaagg cgtgtccggg cagcaggctc tctgccatca gcagagttga   600
gtagcaacag ctgcagccct ggctgtggcc ctgaggtccc cccaacccct cctggctctc   660
acagtgcctt tacctcaagc tttagcttta ttcggctctc gcttggctct gccggggaac   720
gtggagaagc agaaggctgc ccaccatcca gagaggctga gtcccattgc cagagccccc   780
aggagatggg agccaaagct gccagcttgg acgggcctca cgaggacccg cgatgtctct   840
ctcagccctt cagtctcttg gctacacggg tctctgcaga cttggcccag gccgcaagga   900
acagctccag gccagagcgt gacatgcatt ctttaccaga catggaccct ggctcctcca   960
gttctctgga tccctcactg gctggctgtg gtggtgatgg gagcagcggc tcaggggatg  1020
cccactcttg ggacaccctg ctcaggaaat gggagccagt gctgcgggac tgcctgctga  1080
gaaaccggag gcagatggag gtaatatcct taagattaaa acttcagaaa cttcaggaag  1140
atgcagttga gaatgatgat tatgataaag ctgacgtt acaacaaga ttagaagacc  1200
tggaacaaga gaaaatcagc ctgcactttc aacttccttc aaggcagcca gctcttagca  1260
gtttcctggg tcacctggca gcacaagtcc aggctgcctt cgccgtggg gccactcagc  1320
aggccagcgg agatgacacc cacacccca ctgagaatgga gccgaggctg ttggaaccca  1380
```

```
ctgctcagga cagcttgcac gtgtccatca cgagacgaga ctggcttctt caggaaaagc      1440
agcagctaca gaaagaaatc gaagctctcc aagcaaggat gtttgtgctg gaagccaaag      1500
atcaacagct gagaagggaa atagaggagc aagagcagca actccagtgg cagggctgcg      1560
acctgacccc actggtgggc cagctgtccc tgggtcagct gcaggaggtc agcaaggcct      1620
tgcaggacac cctggcctca gccggtcaga ttcccttcca tgcagagcca ccggaaacca      1680
taaggagcct ccaggaaaga ataaaatccc tcaacttgtc acttaaagaa atcactacta      1740
aggtgtgtat gagtgagaaa ttctgcagca ccctgaggaa gaaagttaac gatattgaaa      1800
cccaactacc agccttgctt gaagccaaaa tgcatgccat atcaggaaac catttctgga      1860
cggctaaaga cctcaccgag gagattagat cattaacatc agagagagaa gggctggagg      1920
gactcctcag caagctgttg gtgttgagtt ccaggaatgt caaaaagctg ggaagtgtta      1980
aagaagatta caacagactg agaagagaag tggagcacca ggagactgcc tatgaaacaa      2040
gtgtgaagga aaatactatg aagtacatgg aaacacttaa gaataaactg tgcagctgca      2100
agtgtccact gcttgggaaa gtgtgggaag ctgacttgga agcttgtcga ttgcttatcc      2160
agtgcctaca gctccaggaa gccaggggaa gcctgtctgt agaagatgag aggcagatgg      2220
atgacttaga gggagctgct cctcctattc cccccaggct ccactccgag gataaaagga      2280
agaccccttt gaaggtattg gaagaatgga agactcacct catcccctct ctgcactgtg      2340
ctggaggtga acagaaagag gaatcttaca tcctttctgc agaacttgga gaaaagtgtg      2400
aagacatagg caagaagcta ttgtacttgg aagatcaact tcacacagca atccacagtc      2460
atgatgaaga tctcattcag tctctcagga gggagctcca gatggtgaag gaaactctgc      2520
aggccatgat cctgcagctc cagccagcaa aggaggcggg agaaagagaa gctgcagctt      2580
cctgcatgac agctggtgtc cacgaagcac aagcctgagg agtgacggga tggggagggg      2640
aggtgggcca ccatgtttgg acccgggggg ctgctcttcc ctcccccgcc atagctaaga      2700
tgcctgaatc aattacggag atacagagcc ttgaggtctt tcagtggaaa ggtggttcat      2760
gttcattctc atcagtgtga aactgaggag tctgcaattt ggaatatgga gagagagact      2820
gatttgctga atttccttct aaatgtcact caaaaatttc ttttccatgt cattcttggg      2880
aatgtcttcc acaggatttg agaatagttt catctcagcc cccattagag agaagttggg      2940
gtgaattctg gaaaaatgtc tcttttttcct gtgccatttg ccttctgctg caacgaaaat      3000
atttcctgat tcaagattct ataaaaagga aaccaagcat aagactctgt catcatacct      3060
gttacacgtt cctacaggtg cacaatctaa gagagctaat taacctcaga gtctggagtt      3120
aacagctttt caccttactt ctcctgtgat ctaatattat cttagaaaaa ttaatatgca      3180
atttccaaaa gatatttggt taagacaaca acctcccagt gatatgccac ctttcaattt      3240
tccttttgtg gcaatgattg catctgaaga aaggatccct gagagtctct gtttcatcag      3300
gacattctga aatttaccca cagtgaggct gtggatggat caggggacct gtataaaatg      3360
tttgagcctg ttccattttc ccgtggaacc tgtttcactc aatgccaggc agtgcagcat      3420
ttaggaaagc agtgcagtac tcagtaaggc agtgcagtac tcagtaacac aatacagtac      3480
tcaggcagtg cagtactcag taagacagtg cagtgctcag taaggcagtg caatactcag      3540
taacagtgta gtactcagta acagtgaagt actcagtaat acagtacagt attcagtaag      3600
gcagtgaagt actcagtaat acaatacagt actcagttag gcagtgcagt actcaggaat      3660
gcagcacagt actcaggcag tgcaatactc agtgcggtac tcagtaacac agtgcagtac      3720
tcagtaacag tgcagtactc agtaacagtg cagtactcag taaggcagtg cagtactcag      3780
```

```
taacacagtg cagtactcag taatacagta cagtactcag taaggcagta tggtactcag    3840
taaagcaatg caatgctcag taacacagtg cagtgctcaa taaggcagtg cagtgctcag    3900
taaggcagtg aattgcttag taacacagtg tagtgctcag taggacagca tagtactcag    3960
taacacaggg cagctagtac tcagtactat aagtactgag tacttatata ggcaatgtag    4020
tactcagtaa atcagtgcag tactcagtaa tgcaagggca tttcaggctc ctgctgggct    4080
gcttctttgg cccagctggg actcctattg agacagctgc aaaacaggct gatttcaatt    4140
aggcagcact tcccaaagtg cactgaggaa ggtggcccca agagaagctc tctaaacaaa    4200
ggagtaccct ctctggtcaa gtacctttgg taaatacacc ataccataat atctgcttgg    4260
agaaccacaa tgcacattag catattagtc tgagagagaa cttatagtaa ggaaactcac    4320
ttgattttat ctaacctcaa actttccaag tttaatggat cgtgaatttt tttcatgtaa    4380
ctcctattca tatcccatag atctagtatt gtacagcact gcattctctg aggaagtccc    4440
agtccaaact ctgatttaca tcactttaga aaccacactc acactttgc agagtgttga     4500 gcttaataac tacctgccac agattggtaa atttaatcca gtggttgttc tgtttgtgct    4560
tctgttctca tttatgtgtt tagggatagt gaggttcctg ccttcactag gatccacgga    4620
tatgagacca tttttgtcat ttcctgaagt cacactggcg tttccagaag gcatctggtg    4680
ctttgctcag ccttccatgc tgtgcagcac ttctgtcctc agtcaaggag atggccatgc    4740
ttaagccagc aattggctgg ggtccaggaa acaaagcaaa agcacaatat gtgaatgtgc    4800
tgattgtgtt ccctatggct ttatctcgag caaaatacac tctacatatt ttaataataa    4860
gtataattag cttgttcctg gacttcattt tcaatgatga accaaattcc tgaattattt    4920
ataattgtgt ctaaagaaaa ttatgaactg gtcacatggc acttggaatc cttgagttaa    4980
ttccagtgaa gcaaaacttg gaagagtca ggattggcca cattgccaat aacaaattcc     5040
tacttcgaca tatgtctttt caaaaagcct cccagacaca agacatctta accgtcacta    5100
gcccaagtgt tttgtattac tcagacacca tcatgaaata attctgtgag gtcatgatgt    5160
atttgaaaat tctgcaagtt aataactgcc ttgaattgtt tgaacccgaa ataagggttc    5220
tttggtacct ctagtagata gtgtgttcat ttccctgctg caaattttga agtatttggg    5280
caggtgagtc atgtttttaac cacaagccat aactcatctg ttgtctttgc ttggtcttag    5340
agtatcattc agaaagtccg ctaagggcca gcgtgcttct tctggctaca caaccttctc    5400
aggacaagcc cactgtctta agccactttg accctgggag acacaggact gtgtatcctc    5460
aatcatacta tacagcagtt tttgtcaggg gaacataaaa atatccaaga gaggttaggg    5520
cttagattta aaagcatcaa acaacaaca atggaaattt atgttggcga tagccaagac    5580
cacaagcaaa agcacatact ggaaatgatg agttagaatc tgatttgact gggatgtttt    5640
atgagaatgt aagtgtgata ttatactgtc tgccttgctg gaatgctggc tttcaaatgg    5700
tcacccattt ttctttcact ggcctgagtt aggacatgct atcagtaata gtcccagttc    5760
catccaactt tctgaaattt cattttttt tttgagatgg agtctctctc tgtcacccaa      5820
gttggagtgc agtggccccg caatctcggc tcactgcaac ctctacctcc caggttcaag    5880
ctattctact gcctcagcct cccaagtagc tggggttaca ggcatttgcc accgggccct    5940
gatgattttt gtattttag tagagacagg gcttcaccat gttggctagg agggtctcaa     6000
actcctgacc tcaggcgatc cacccccacc tcggcttccc aaagtgctga gattacaggt    6060
gtgagccacc gcacccggcc aactttctga aatttcaaaa ctgaattgat ccttctccaa    6120
attagtatat actattggaa acttgtcttt ccctgcagta aggctggttt ccccacccca    6180
```

```
gaaacatgta acggttggta ccatgctaag cccttgccat gctaagccct ttacagtcat   6240
atcctataat ccccatatca accttataag gaaggtgttt gtagatgatg caactgagcc   6300
ttaagaggac taattccctt tttctaaggc acagagctgg taaaatgtga agtaatagtg   6360
aacctaacag tcagagacag gcagcatgct cttaactagt gctcttccta aagttccttt   6420
aatgtccttt tgagattttg agccatgaa cttacttgtt cacctggcta agaactcatg    6480
gccactgtgg aaatcttggt tagggagtca agaaactga gcctggggca aacgaggctt    6540
cccacactgc caggggagcc tcactgtgaa gtctaggctc agacaggcat caacaaacct   6600
attcacccca ccatcatcct gatctaacca ttccccagtc atcccaggaa aaccactcac   6660
agcctgacac tgggctgact tcttgaaga tcctcatcca attggtgttt ttcagaagtg     6720
ttccaatatt atgaattctg tgttgtggag aaaagcaacc atgcatttac tggtcaatgc   6780
cttcttgtat atgtaattca atacttttac ttttaatatc ctcaccttat ctaatctttg   6840
aattttgtca tgtaatttat tgcttcatta aggttacttt tgttataca aataaaagc     6900 tgatatccaa ggcaaaaaaa aaaaaaaaaa                                    6930
```

```
<210> SEQ ID NO 13
<211> LENGTH: 15
<212> TYPE: PRT
<213> ORGANISM: Mus musculus

<400> SEQUENCE: 13

Pro Leu Ala Ser Pro Ala Leu Asn Gly Pro Ala Asp Ile Ala Ser
1               5                   10                  15

<210> SEQ ID NO 14
<211> LENGTH: 15
<212> TYPE: PRT
<213> ORGANISM: Mus musculus

<400> SEQUENCE: 14

Ala Leu Asn Gly Pro Ala Asp Ile Ala Ser Leu Pro Gly Phe Gln
1               5                   10                  15

<210> SEQ ID NO 15
<211> LENGTH: 15
<212> TYPE: PRT
<213> ORGANISM: Mus musculus

<400> SEQUENCE: 15

Ala Asp Ile Ala Ser Leu Pro Gly Phe Gln Asp Thr Phe Thr Ser
1               5                   10                  15

<210> SEQ ID NO 16
<211> LENGTH: 15
<212> TYPE: PRT
<213> ORGANISM: Mus musculus

<400> SEQUENCE: 16

Leu Pro Gly Phe Gln Asp Thr Phe Thr Ser Ser Phe Ser Phe Ile
1               5                   10                  15

<210> SEQ ID NO 17
<211> LENGTH: 15
<212> TYPE: PRT
<213> ORGANISM: Mus musculus

<400> SEQUENCE: 17

Gln Leu Ser Leu Gly Ala Ala Gly Glu Arg Gly Glu Ala Glu Gly
```

```
<210> SEQ ID NO 18
<211> LENGTH: 15
<212> TYPE: PRT
<213> ORGANISM: Mus musculus

<400> SEQUENCE: 18

Ala Ala Gly Glu Arg Gly Glu Ala Glu Gly Cys Leu Pro Ser Arg
1               5                   10                  15

<210> SEQ ID NO 19
<211> LENGTH: 15
<212> TYPE: PRT
<213> ORGANISM: Mus musculus

<400> SEQUENCE: 19

Gly Glu Ala Glu Gly Cys Leu Pro Ser Arg Glu Ala Glu Pro Leu
1               5                   10                  15

<210> SEQ ID NO 20
<211> LENGTH: 15
<212> TYPE: PRT
<213> ORGANISM: Mus musculus

<400> SEQUENCE: 20

Cys Leu Pro Ser Arg Glu Ala Glu Pro Leu His Gln Arg Pro Gln
1               5                   10                  15

<210> SEQ ID NO 21
<211> LENGTH: 15
<212> TYPE: PRT
<213> ORGANISM: Mus musculus

<400> SEQUENCE: 21

Glu Ala Glu Pro Leu His Gln Arg Pro Gln Glu Met Ala Ala Glu
1               5                   10                  15
```

DISC-1 PATHWAY ACTIVATORS IN THE CONTROL OF NEUROGENESIS

RELATED APPLICATION

This application claims priority under 35 USC §119 to U.S. Provisional Application Nos. 61/130,071, filed May 28, 2008, and 61/155,973 filed Feb. 27, 2009 the entire contents of which are hereby incorporated by reference.

FIELD OF THE INVENTION

The invention relates to methods of treating neurological disorders in a subject, by activating a DISC1 pathway. Methods of promoting neurogenesis in adult neural progenitor cells, enhancing nerve generation and treating GSK3 disorders as well as related compositions are also provided.

BACKGROUND OF THE INVENTION

Few neurological and neuropsychiatric disorders such as schizophrenia, attention deficit disorder (ADD), schizoaffective disorder, bipolar affective disorders and unipolar affective disorder have clinical manifestations that are correlated with demonstrable defects in the structure and/or function of the nervous system. Many of these disorders, however, involve subtle and/or undetectable changes in the cellular and molecular levels of nervous system structure and function. The lack of knowledge of the underlying anatomical or biochemical pathologies slows the development of new therapies for neurological and neuropsychiatric disorders. Rational correlations between these disorders and the underlying neurological signaling pathways have not yet been sufficient to enable the generation of new neurons and yield improved therapies to combat neurological and neuropsychiatric disorders.

New neurons are generated from neural stem cells, in two regions of the adult mammalian central nervous system: the subventricular zone of the lateral ventricle, and the subgranular zone of the hippocampal dentate gyrus. Signals provided by the microenvironment contribute to the regulation of the maintenance, proliferation and neuronal fate commitment of the local stem cells. Many of these signals and signaling pathways are unknown.

The Disrupted In Schizophrenia 1 (DISC1) gene was initially identified as being disrupted by a balanced chromosomal translocation (1; 11) (q42; q14.3) in a large Scottish family with a high incidence of psychiatric disorders including major depression, schizophrenia and bipolar disorder. Subsequent studies provided indications, although no defined molecular/cellular mechanisms, that DISC1 may play a role in brain development.

SUMMARY

The present invention provides in some aspects methods of treating neurological disorders in a subject by promoting neurogenesis in adult neural progenitor cells via compositions that activate the DISC1 pathway. In particular, the invention is based in part on the finding that suppression of DISC1 reduces proliferation of neural progenitors, leading to premature cell cycle exit and differentiation. Conversely, DISC1 gain-of-function promotes progenitor proliferation.

In one aspect, the invention provides a method of treating a neurological disorder in a subject by administering to a subject a DISC1 pathway activator in an effective amount to treat the neurological disorder. In some embodiments, the DISC1 pathway activator has not previously been indicated for the treatment of a neurological disorder.

In some embodiments, the neurological disorder is Alzheimer's disease, schizophrenia or schizo-affective disorder, bipolar disorder or unipolar disorder, depression, substance abuse, neurodegenerative disease, autism or autism spectrum disorder, or a disorder resulting from neural damage such as spinal injuries or brain injuries. The neurodegenerative disease may be for instance, amyotrophic lateral sclerosis or Parkinson's disease. In some embodiments, the invention provides methods for treating brain injury resulting from traumatic injury or stroke.

In some embodiments, the method comprises the administration of a DISC1 pathway activator. In some embodiments, the DISC1 pathway activator is a DISC1 activator. In some embodiments, the DISC1 pathway activator is a DISC1 agonist. In some embodiments, the DISC1 agonist is a DISC1 fragment. The DISC1 fragment may be, for instance, peptide 2. In some embodiments, the DISC1 agonist is a peptide mimetic. In some embodiments, the invention provides a DISC1 pathway activator that is an agent that promotes DISC1-GSK3 binding. The agent that promotes DISC1-GSK3 binding may be, for instance, an antibody. In some embodiments, the DISC1 pathway activator is a DISC1 inducing agent.

In some embodiments, the subject may not have been previously diagnosed as having a DISC1 mutation. In some embodiments, the subject does not have a DISC1 mutation.

Another aspect of the invention is a method of enhancing neural progenitor proliferation and differentiation by contacting a neural progenitor cell with a DISC1 pathway activator in an effective amount to enhance neural progenitor proliferation and differentiation.

In one aspect the invention provides a method of enhancing nerve generation, by contacting a nerve with a DISC1 pathway activator in an effective amount to enhance nerve generation.

The invention in some aspects is a composition of a DISC1 pathway activator, wherein the DISC1 pathway activator is a DISC1 agonist, and a carrier. In some embodiments, the DISC1 agonist is a peptide, wherein the peptide optionally is a DISC1 fragment. In some embodiments the DISC1 fragment is peptide 2. In some embodiments, the DISC1 agonist is a peptide mimetic. In some embodiments, the composition is sterile.

The invention in some aspects is a method involving contacting a DISC1 molecule with a GSK3β molecule, in the presence and in the absence of a putative modulator; detecting binding between the DISC1 molecule and the GSK3β molecule in the presence and absence of the putative modulator; and identifying a modulator based on a decrease or increase in binding between the DISC1 molecule and the GSK3β molecule in the presence of the putative modulator, as compared to binding in the absence of the putative modulator.

In one aspect the invention provides a method for identifying a DISC1 modulator by incubating a DISC1 expressing cell in the presence and in the absence of a putative modulator; detecting GSK3β activity in the presence and absence of the putative modulator; and identifying a DISC1 modulator based on a decrease or increase in the GSK3β activity in the presence of the putative modulator, as compared to the activity in the absence of the putative modulator.

In one aspect the invention provides a method of treating a GSK3 disorder by administering to a subject a DISC1 pathway activator in an effective amount to treat the GSK3 disorder in the subject, wherein the DISC1 pathway activator has not previously been indicated for the treatment of the GSK3 disorder.

In some embodiments, the DISC1 pathway activator is a DISC1 agonist. The DISC1 agonist may be, for instance, a DISC1 fragment, such as for instance, peptide 2. In other embodiments the DISC1 agonist is a small molecule. In some embodiments the DISC1 pathway activator is a DISC1 inducing agent.

In some embodiments the GSK3 disorder is diabetes. In some embodiments the GSK3 disorder is prostate cancer. In some embodiments the GSK3 disorder is an autoimmune disease, an inflammatory disease, a metabolic disorder, an angiogenic disorder, glaucome, baldness, or a cardiovascular disease.

In another aspect the invention is a compound of formula:

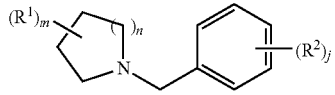

wherein
n is 1 or 2;
m is an integer between 0 and 10, inclusive;
j is an integer between 0 and 5, inclusive;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR^A$; —$C(=O)R^A$; —$CO_2R^A$; —$C(=O)N(R^A)_2$; —CN; —SCN; —$SR^A$; —$SOR^A$; —$SO_2R^A$; —$NO_2$; —$N(R^A)_2$; —$NHC(O)R^A$; or —$C(R^A)_3$; wherein each occurrence of $R^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

each occurrence of $R^2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR^B$; —$C(=O)R^B$; —$CO_2R^B$; —$C(=O)N(R^B)_2$; —CN; —SCN; —$SR^B$; —$SOR^B$; —$SO_2R^B$; —$NO_2$; —$N(R^B)_2$; —$NHC(O)R^B$; or —$C(R^B)_3$; wherein each occurrence of $R^B$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy; and pharmaceutically acceptable salts thereof and uses of the compound in any of the methods described herein.

In another aspect the invention is a compound of formula:

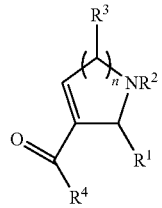

wherein
n is 1 or 2;
$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR^A$; —$C(=O)R^A$; —$CO_2R^A$; —$C(=O)N(R^A)_2$; —CN; —SCN; —$SR^A$; —$SOR^A$; —$SO_2R^A$; —$NO_2$; —$N(R^A)_2$; —$NHC(O)R^A$; or —$C(R^A)_3$; wherein each occurrence of $R^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

$R^2$ is hydrogen, $C_{1-6}$ aliphatic, or a protecting group;
each occurrence of $R^3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR^C$; —$C(=O)R^C$; —$CO_2R^C$; —$C(=O)N(R^C)_2$; —CN; —SCN; —$SR^C$; —$SOR^C$; —$SO_2R^C$; —$NO_2$; —$N(R^C)_2$; —$NHC(O)R^C$; or —$C(R^C)_3$; wherein each occurrence of $R^C$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

$R^4$ is hydrogen; cyclic or acyclic, substituted or unsubstituted, branched or unbranched aliphatic cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR^D$; —$C(=O)R^D$; —$CO_2R^D$; —$C(=O)N(R^D)_2$; —CN; —SCN; —$SR^D$; —$N(R^D)_2$; —$NHC(O)R^D$; or —$C(R^D)_3$; wherein each occurrence of $R^D$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy; and pharmaceutically acceptable salts and uses of the compound in any of the methods described herein.

In another aspect the invention is a compound of formula:

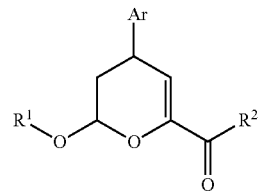

wherein
$R^1$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$C(=O)R^A$; —$CO_2R^A$; —$C(=O)N(R^A)_2$; or —$C(R^A)_3$; wherein each occurrence of $R^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$^B$; —C(=O)R$^B$; —CO$_2$R$^B$; —C(=O)N(R$^B$)$_2$; —SR$^B$; —N(R$^B$)$_2$; —NHC(O)R$^B$; or —C(R$^B$)$_3$; wherein each occurrence of R$^B$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

Ar is independently substituted or unsubstituted, branched or unbranched aryl; or substituted or unsubstituted, branched or unbranched heteroaryl; and pharmaceutically acceptable salts thereof and uses of the compound in any of the methods described herein.

In another aspect the invention is a compound of formula:

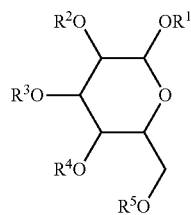

wherein

R$^1$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^A$; —CO$_2$R$^A$; —C(=O)N(R$^A$)$_2$; or —C(R$^A$)$_3$; wherein each occurrence of R$^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

R$^2$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^A$; —CO$_2$R$^A$; —C(=O)N(R$^A$)$_2$; or —C(R$^A$)$_3$; wherein each occurrence of R$^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

R$^3$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^A$; —CO$_2$R$^A$; —C(=O)N(R$^A$)$_2$; or —C(R$^A$)$_3$; wherein each occurrence of R$^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

R$^4$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^A$; —CO$_2$R$^A$; —C(=O)N(R$^A$)$_2$; or —C(R$^A$)$_3$; wherein each occurrence of R$^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

R$^5$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^A$; —CO$_2$R$^A$; —C(=O)N(R$^A$)$_2$; or —C(R$^A$)$_3$; wherein each occurrence of R$^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy; and pharmaceutically acceptable salts thereof and uses of the compound in any of the methods described herein.

In other aspects the invention relates to compositions for use of each of the methods described herein. The invention also encompasses compositions for manufacture of medicaments for the uses and methods described herein. The invention also contemplates uses of compositions for each of the methods described herein. The compositions are any of the activators or compounds described herein.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

Figures 1A, 1B:
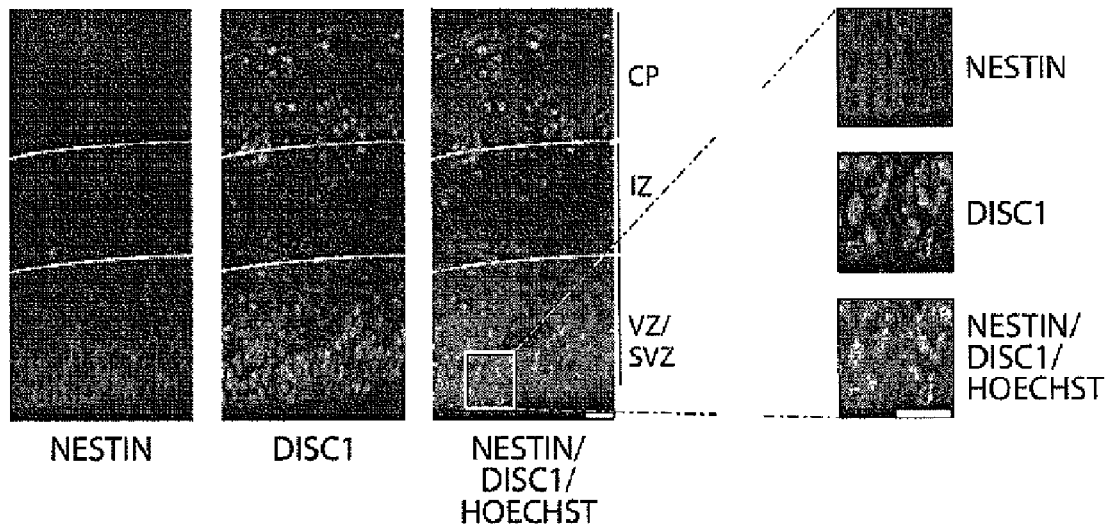
FIG. 1 shows that DISC1 regulates progenitor cell proliferation in vitro. a and b. E15 embryonic brains were sectioned for co-staining with anti-DISC1 and anti-Nestin antibodies. Scale bar=20 μm. c. Cell proliferation is reduced in AHP cells infected with lentivirus expressing DISC1 shRNAs. GFP expression is used as a marker for viral infection. Both DISC1 shRNAs significantly reduced cell proliferation. (n=3, p<0.01). d. BrdU incorporation is decreased in DISC1 knockdown cells. AHPs infected with control, DISC1 shRNA-1, or shRNA-2 lentivirus were pulse labeled with 10 μM BrdU and stained with BrdU antibody. The percentage of GFP positive cells that are also BrdU positive cells is shown (n=4, p<0.01). e. Mitotic index is reduced in DISC1-silenced AHPs. The percentage of GFP positive cells that are also pH3 positive is shown (n=3, p<0.01). f. Histograms for FACS analysis of N2a cells transfected with DISC1 shRNAs. Bar graphs depict the percentage of GFP positive cells in G0/G1 (n=3, p<0.01). g. Cell proliferation is increased in DISC1 overexpressing cells. AHPs were infected with either control or DISC1-WT lentivirus. Cell number was counted for 2 days (n=3, p<0.01). h. BrdU incorporation is increased in DISC1-overexpressing AHPs. AHPs infected with either control or WT-DISC1 lentivirus were labeled with BrdU (10 µM) and stained with anti-BrdU antibody. The percentage of GFP positive cells that are also BrdU positive cells is shown (n=4, p<0.001). i. Increased mitotic index in DISC1 overexpressing AHPs. AHPs infected with either control or WT-DISC1 lentivirus were stained with the pH3 antibody. The percentage of GFP positive cells that are also pH3 positive is shown (n=4, p<0.001).

daily for 7 days. The GFP signal represents lentiviral infected cells in dentate gyrus. Scale bar=50 μm. d. DISC1 knockdown reduced adult progenitor proliferation in dentate gyrus, but this defect can be rescued by SB216763. The percentage of GFP and BrdU double positive cells is shown (n=5, *, p<0.05; , p<0.01; *, p<0.005; ns, not significant). Scale bar=10 μm.

FIG. 6 shows the suppression of DISC1 expression by RNA interference. N2a cells were transduced with control or DISC1 shRNA lentiviruses. Endogenous DISC1 protein was immunoprecipitated and blotted with an anti-DISC1 antibody.

FIG. 7 shows the suppression of DISC1 expression by RNA interference in vivo. a and b. E15 mice were pulse labeled with 100 mg/kg BrdU for 2 hours and embryonic brains were harvested for co-staining with anti-DISC1 and anti-BrdU antibodies. Scale bar=20 μm. c. E15 embryonic brains were sectioned and co-stained with anti-DISC1 and anti-pH3 antibodies. Scale bar=10 μm. d. DISC1 expression is knocked down in vivo. Electroporated embryonic brain sections were stained with anti-DISC1. Circled cells are GFP-positive cells. Scale Bar=20 μm.

FIG. 8 shows that BrdU incorporation is reduced in DISC1 knockdown cells. a. BrdU incorporation is reduced in DISC1 knockdown cells. AHPs infected with either control or DISC1 shRNA lentivirus were pulse labeled with 10 μM of BrdU and stained with BrdU antibody. Scale bar=20 μm. b. Mitotic index is decreased in DISC1-silenced AHPs. AHPs infected with either control or DISC1 shRNA lentivirus were stained with anti-phospho-Histone H3 (pH3) antibody. Scale bar=10 μm. c. BrdU incorporation is increased in DISC1 overexpressing AHPs. AHPs infected with either control or WT-DISC1 lentivirus were labeled with 10 μM of BrdU for an hour and stained with anti-BrdU antibody. Scale bar=20 μm. d. Mitotic index is increased in DISCi overexpressing AHPs. AHPs infected with either control or WT-DISC1 lentivirus were stained with the pH3 antibody. Scale bar=20 μm.

FIG. 9 shows that BrdU incorporation is reduced in DISC1 knockdown brains. a. BrdU incorporation is reduced in DISC1 knockdown brains. E15 electroporated brains were pulse labeled with BrdU (100 mg/kg) for 2 hours and stained with anti-GFP and BrdU antibodies. Arrows indicate GFP and BrdU double positive cells. The bar graph shows the percentage of BrdU and GFP double positive cells to total GFP positive cells in SVZ (n=4, p<0.0005). b. and c. DISC1 shRNAs did not affect the CRE (b) or C/EBP-ATF reporters (c). Bar graph shows the relative luciferase activity (n=3, p<0.0001).

FIG. 10 shows the effects of over-expression of beta-catenin. a. N2a cells were transfected with control, β-catenin shRNA-1 or -2 for 48 hours. Cell lysates were probed with anti-β-catenin and actin antibodies. b. Increased ubiquitination of β-catenin in AHPs expressing DISC1 shRNAs. c. Phosphorylation of Y216 on GSK3β is reduced by all DISC1 fragments at 2 μM in vitro. Stars indicate the different intact GST fusion proteins. Numbers in the panel indicate the relative intensity of the band compared to GST (n=3). d. Cyclin D1 and axin2 expression are reduced in DISC1 silenced AHPs. Numbers in the panel indicate the relative intensity of the band compared to control (n=3). e. Overexpression of DISC1 suppresses the ubiquitination of β-catenin. f. Cyclin D1 and axin2 expression is enhanced in DISC1 overexpressing AHPs. Numbers in the panel indicate the relative intensity of the band compared to vector (n=3).

Figure 10A:
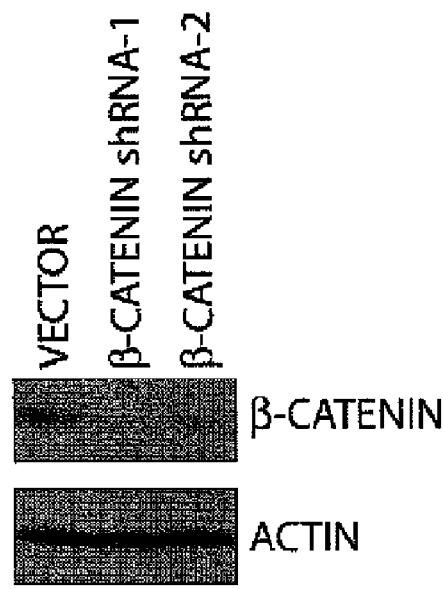
Figure 10B:
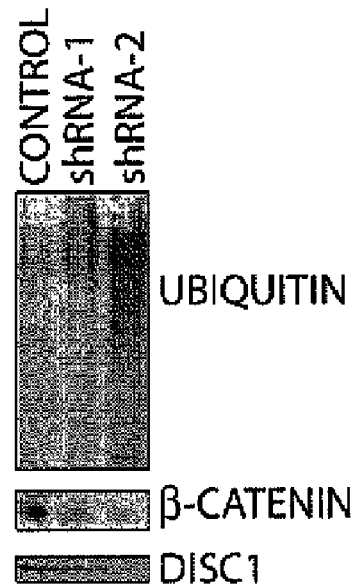
Figures 10F, 11:
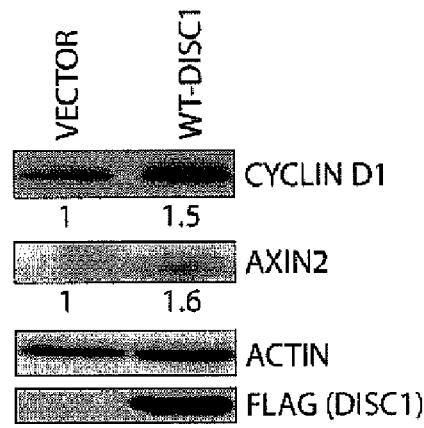

FIG. 11 shows that DISC1 peptides are conserved from mouse to human. Mouse peptide 1 spans amino acids 40 to 78 of mouse DISC1 (SEQ ID NO: 1), while the human homolog spans amino acids 44 to 81 of DISC1 (SEQ ID NO: 9). Mouse peptide 2 spans amino acids 195 to 238 of mouse DISC1 (SEQ ID NO: 2), while the human homolog spans amino acids 193 to 236 (SEQ ID NO: 8).

FIG. 12 shows that the GSK3β inhibitor, SB-216763, can rescue DISC-1 knockdown-induced proliferation defects. a. The GSK3β inhibitor, SB-216763, can rescue DISC-1 knockdown-induced proliferation defects. Primary neural stem cells from E14 brains were infected with control or DISC1 shRNA lentiviruses. 48 hours after transduction, cells were treated with vehicle or SB-216763 (5 μM) for 16 hours and then pulsed with 10 μM BrdU for 2 hours. Shown is percentage of GFP and BrdU double positive cells to total GFP positive cells (n=3, p<0.05). b. The GSK3β inhibitor, SB-216763 or AR-A104418, rescues the TCF activation defect caused by DISC1 knockdown in 293T cells. 1.5 μg of vector or WT-DISC1 was cotransfected with 0.5 μg control or DISC1 shRNA-2, 0.1 μg TCF reporter, and 10 ng pRL-TK vector into 293T cells. 48 hours after transfection, Wnt3a conditional medium with vehicle, SB-216763, or AR-A104418 was added for another 16 hours. The bar graph shows the percentage of relative TCF reporter activity compared to the Wnt3a-treated control (n=3, p<0.0001).

FIG. 13 shows that apoptosis is not elevated by DISC1 silencing in the dentate gyrus. a. Apoptosis is not elevated by DISC1 silencing in the dentate gyrus. Control or DISC1 shRNA-1 lentivirus was injected into the adult dentate gyrus. Brain sections were stained with an anti-active caspase 3 antibody. Scale Bar=20 μm.

FIG. 14 shows behavioral tests performed after DISC1 knockdown using recombinant lentivirus. Behavioral abnormalities in DISC1 knockdown mice. a. DISC1 knockdown in adult dentate gyrus caused increased hyperactivity in the Open Field Test. b and c. DISC1 knockdown in adult dentate gyrus caused depressive-like behavior in the Forced Swimming test and the Novelty Suppression Feeding experiment. b. Forced Swimming Test Mice were put in the beaker with water for 6 minutes and counted the last 4 minutes for the time of immobility. c. Novelty Suppression Feeding Test. Mice were restricted with food for 48 hours and tested for the motivation to eat food. Mice were tested the latency for first bite, the time they spent on food, and the time they ate during 5 minutes. d. DISC1 knockdown causes increased hyperactivity, which can be rescued by a GSK3beta specific inhibitor. Mice were injected and allowed to recover for 2 weeks, then treated with the GDK3beta inhibitor SB216763 at 2 mg/kg/day for two weeks, after that the behavioral test was performed.

Figure 15:
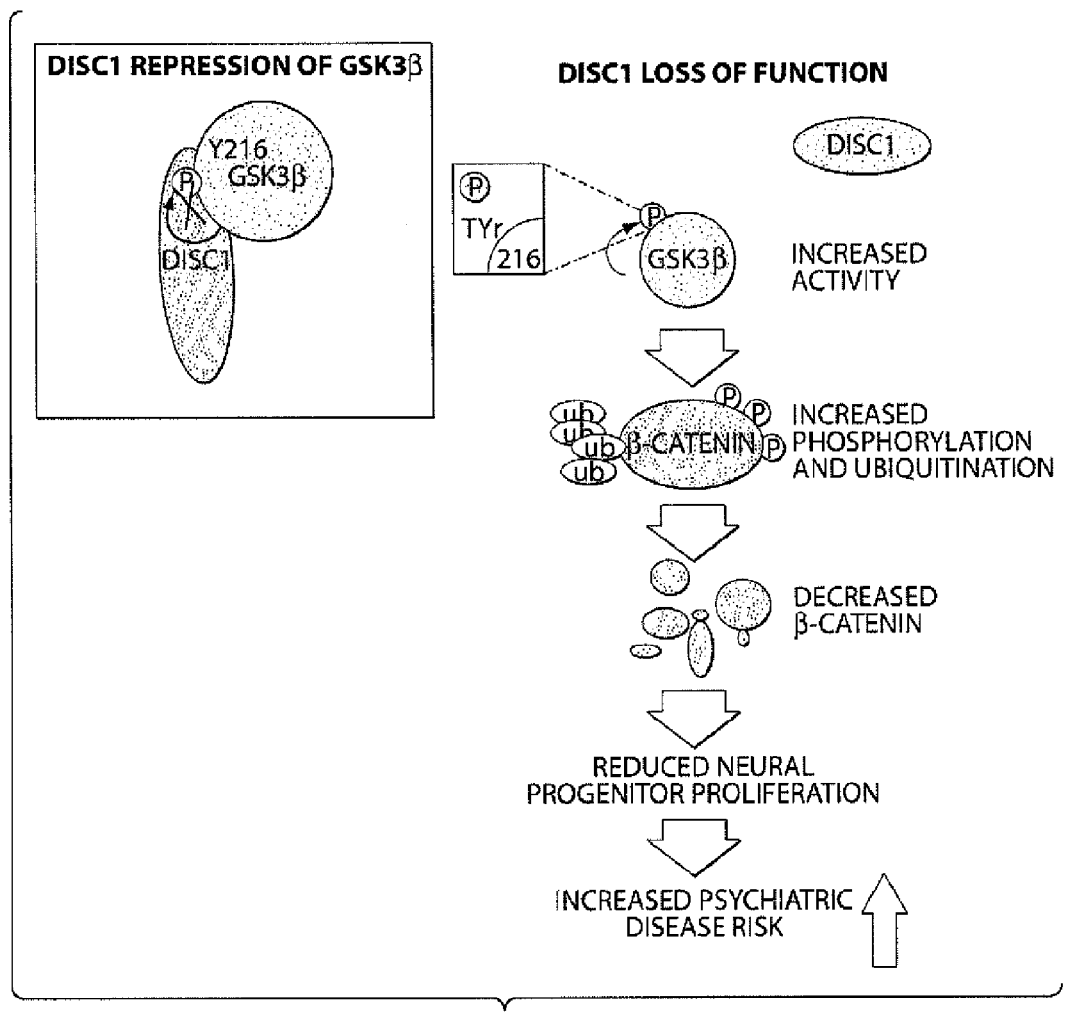

FIG. 15 depicts a role for DISC1 in the development of psychiatric disorders. By regulating GSK3 D activity, DISC1 modulates β-catenin stability and neural progenitor cell proliferation. DISC1 loss-of-function results in neural progenitor proliferation defects and may increase the risk for psychiatric diseases.

Figure 16A:
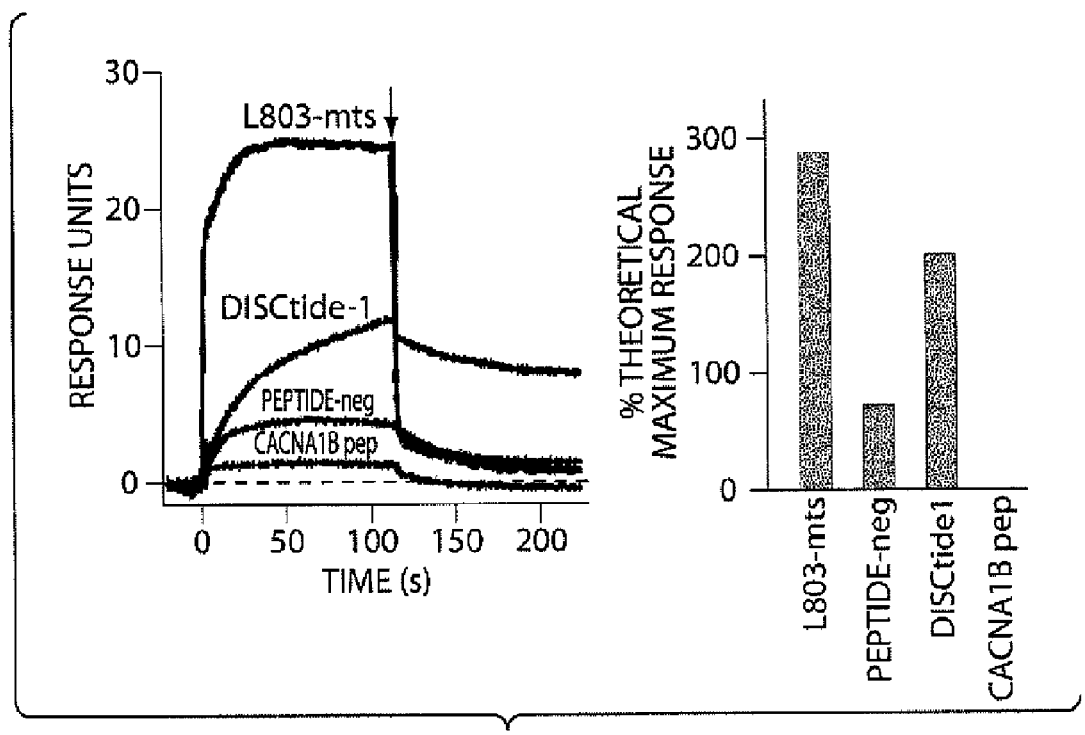
Figure 16B:
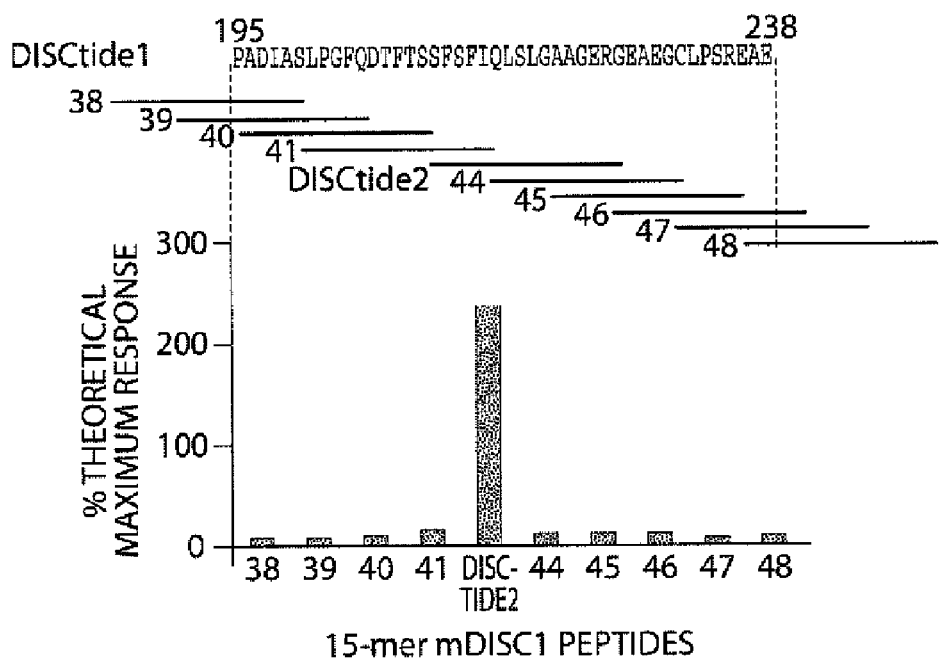

FIG. 16A shows a Surface plasmon resonance (SPR) scan demonstrating that both peptide 2 and L803-MTS bound to GSK3β (percent theoretical maximal response 197% and 259% respectively) at a concentration of 25 μM, while both peptide 1 and the calcium channel peptide showed much lower binding (percent theoretical maximal response 62% and 29% respectively). FIG. 16B is a schematic of overlapping 15-mer peptides that covered peptide 2 and a graph showing the ability of the peptides to bind to GSK3β.

Figure 17A:
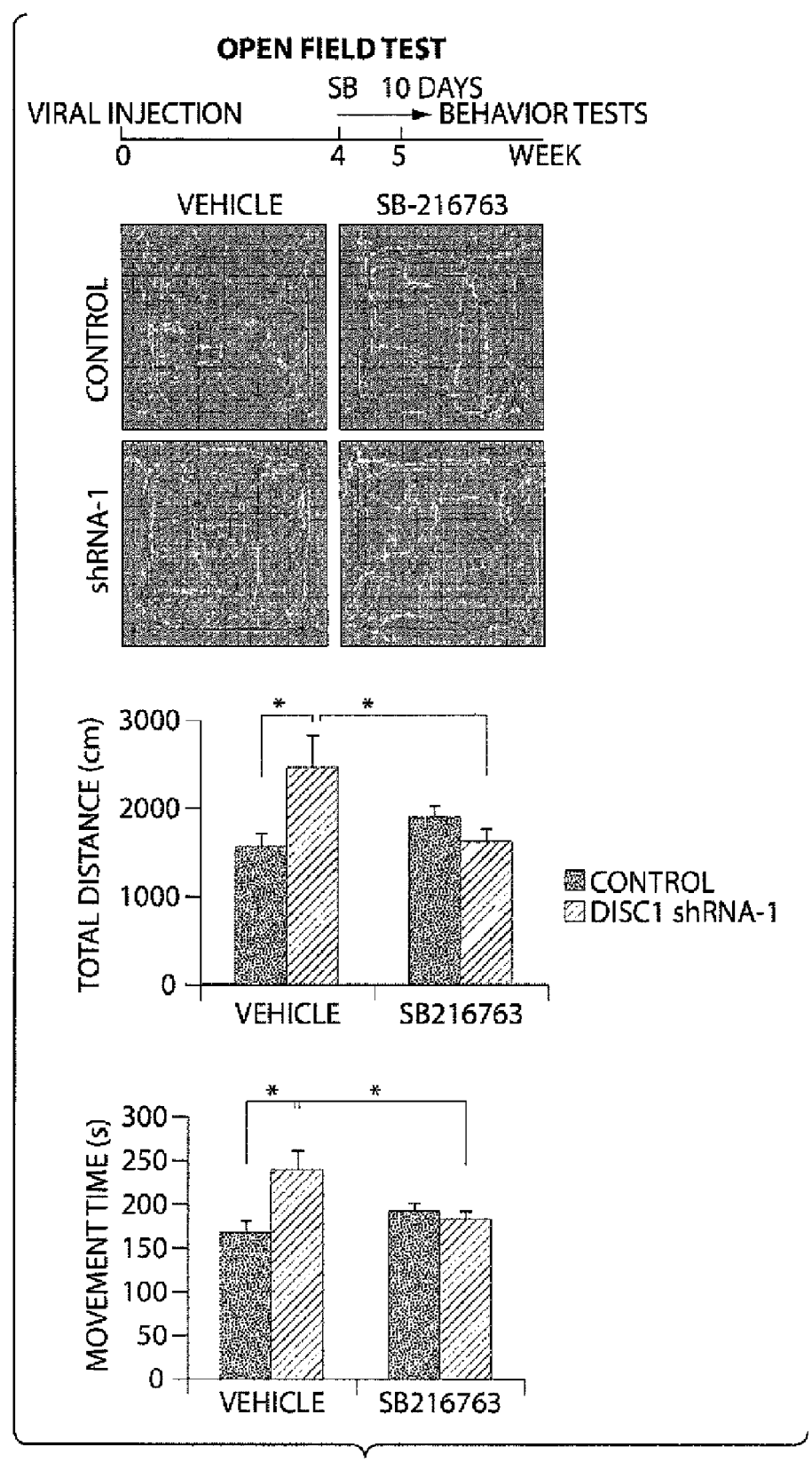
Figure 17B:
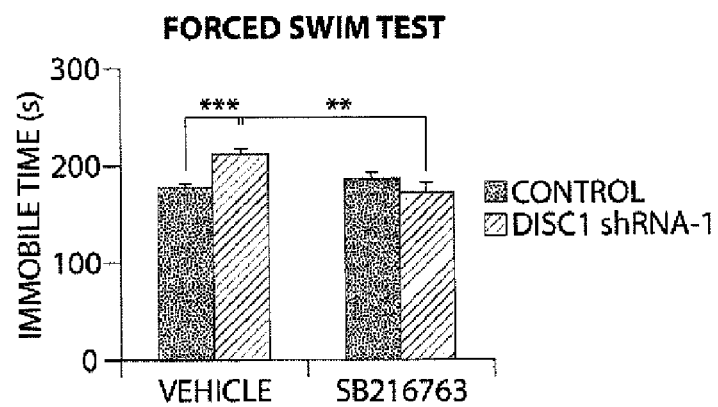
Figure 17C:
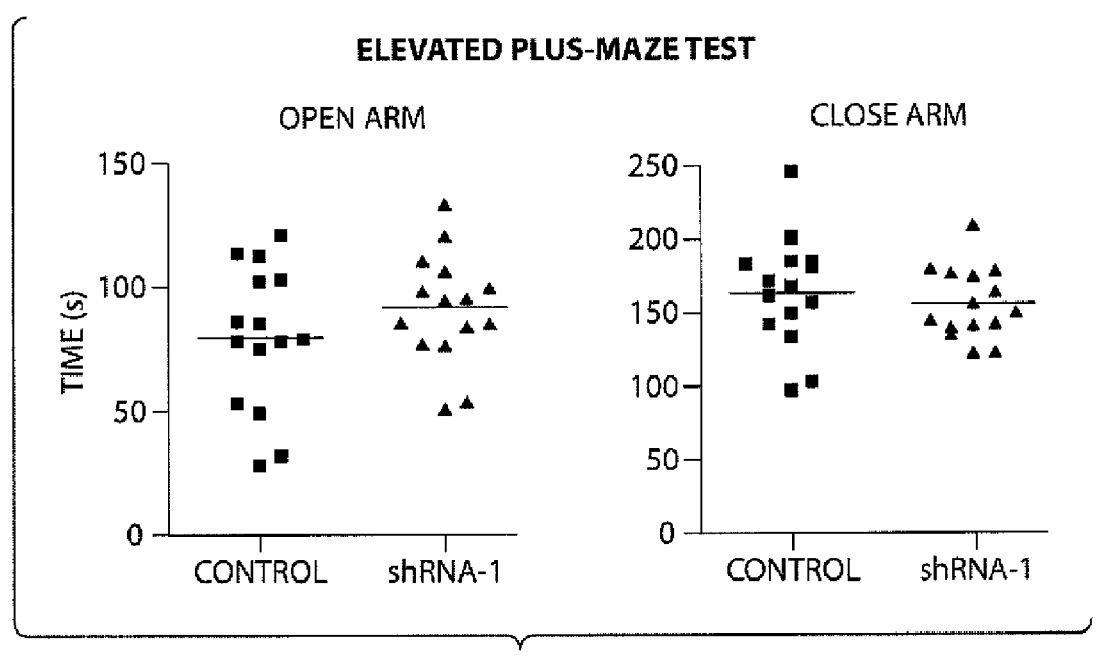

FIG. 17 demonstrates the implications of DISC1/GSK3β/β-catenin interaction in neural psychiatric disorders. FIG. 17A shows the results of an Open Field test in which DISC1 shRNA injected mice traveled a greater distance and spent more time moving in a novel open field than control mice. FIG. 17B is a graph showing the results of a swim test that examined whether DISC1 loss-of-function had consequences on depression-like behavior. DISC1 shRNA infected mice displayed greater immobility, an indicator of depressive behavior, which was also suppressed by SB-216763. Swimming velocity was unchanged. FIG. 17C is demonstrated that DISC1 shRNA infected mice did not display increased anxiety, as there was no difference in time spent in the closed arms versus the aversive open arms in the elevated plus-maze.

Figure 18E:
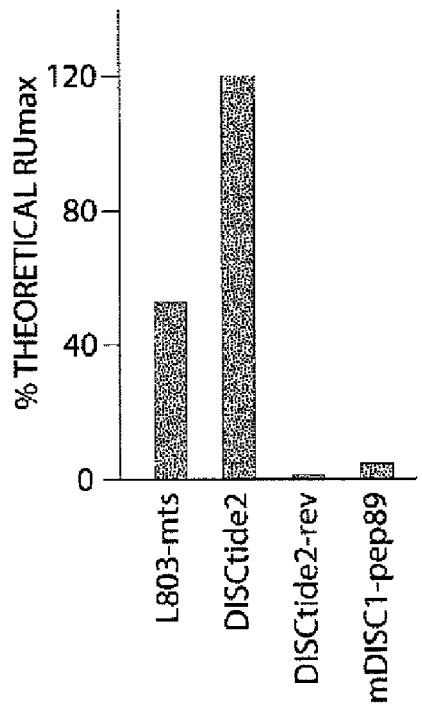

FIG. 18 shows further characterization of peptide 3 establishing that a reversed peptide 3 sequence displayed a negligible binding to GSK3β, demonstrating that the binding of peptide 3 to GSK3β is specific.

Figure 19A:
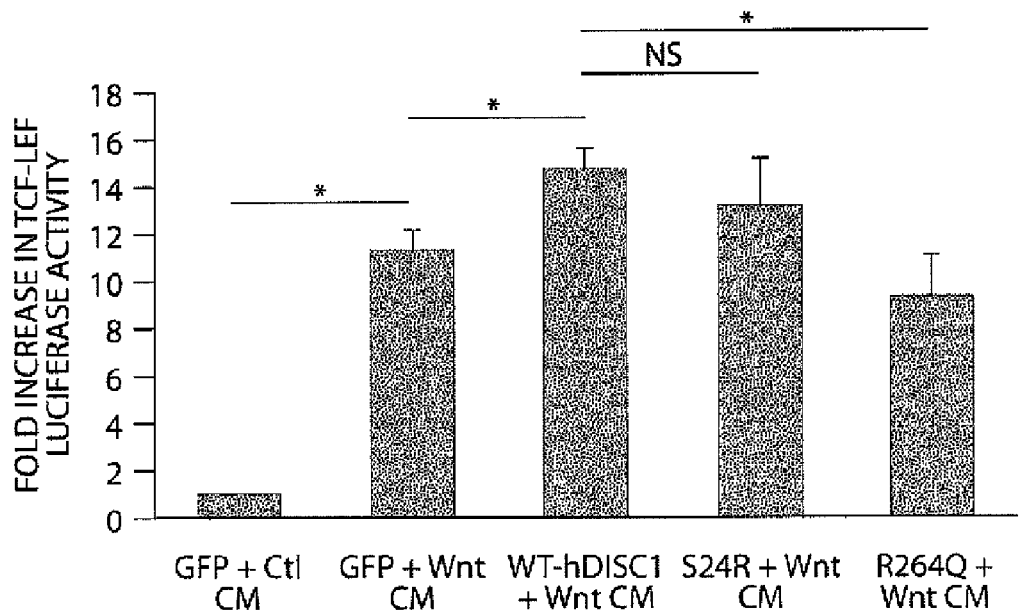
Figure 19B:
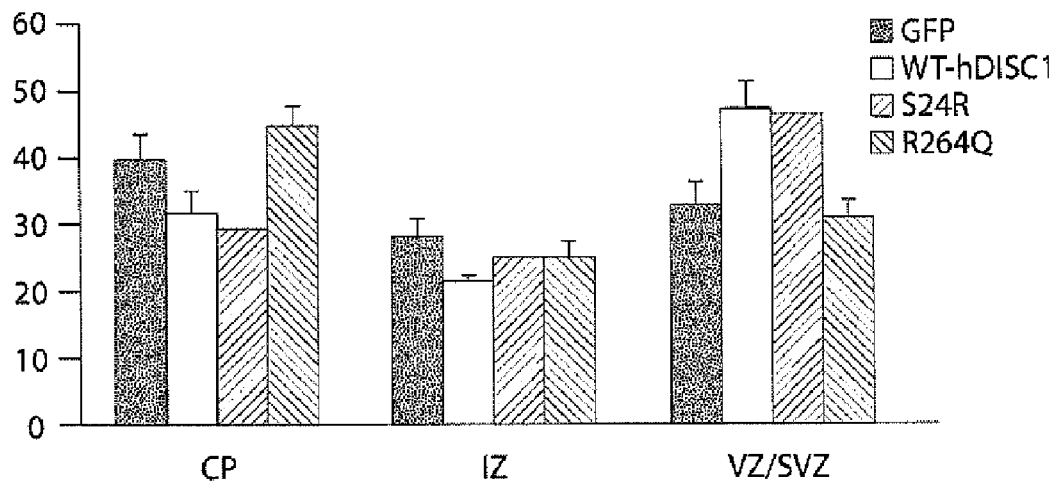

FIG. 19 demonstrates the activity of DISC1 human variants on inhibition of GSK3 and Wnt signaling. FIG. 19A is a bar graph showing the effects of hDISC1 variants on Wnt-induced TCF-LEF reporter activity. FIG. 19B is a set of bar graphs depicting the effects of hDISC1 variants on cell positioning in the developing neocortex after in utero electroporation.

FIG. 20 shows that DISC1 is required for AKT activation. a. Knockdown of DISC1 reduces AKT activation. N2a cells were transfected with control or DISC1 shRNAs. 48 hours after transfection, cell lysates were probed with anti-pT308 AKT antibody, DISC1 and Actin antibody. b. Overexpression of DISC1 increases AKT activation. N2a cells were transfected with vector, DISC1 truncated mutant (1-600aa) or DISC1-WT. cell lysates were probed with anti-pT308 AKT antibody, FLAG and Actin antibody. c. DISC1 associates with AKT. N2a cells were cotransfected with GFP-DISC1 and AKT-HA plasmids. DISC1 protein was immunoprecipitated with GFP antibody and AKT was probed with AKT antibody.

FIG. 21 depicts DISC1 isoforms. (A) Summary of DISC1 exonic structure corresponding to the 4 major isoforms plus the disease-associated truncated mutant. (B) Expression of all 5 isoforms in HE 293 cells as FLAG-tagged recombinant proteins. Cell lysates from these cells were used in SMM assays to find DISC1 ligands.

Figure 22A:
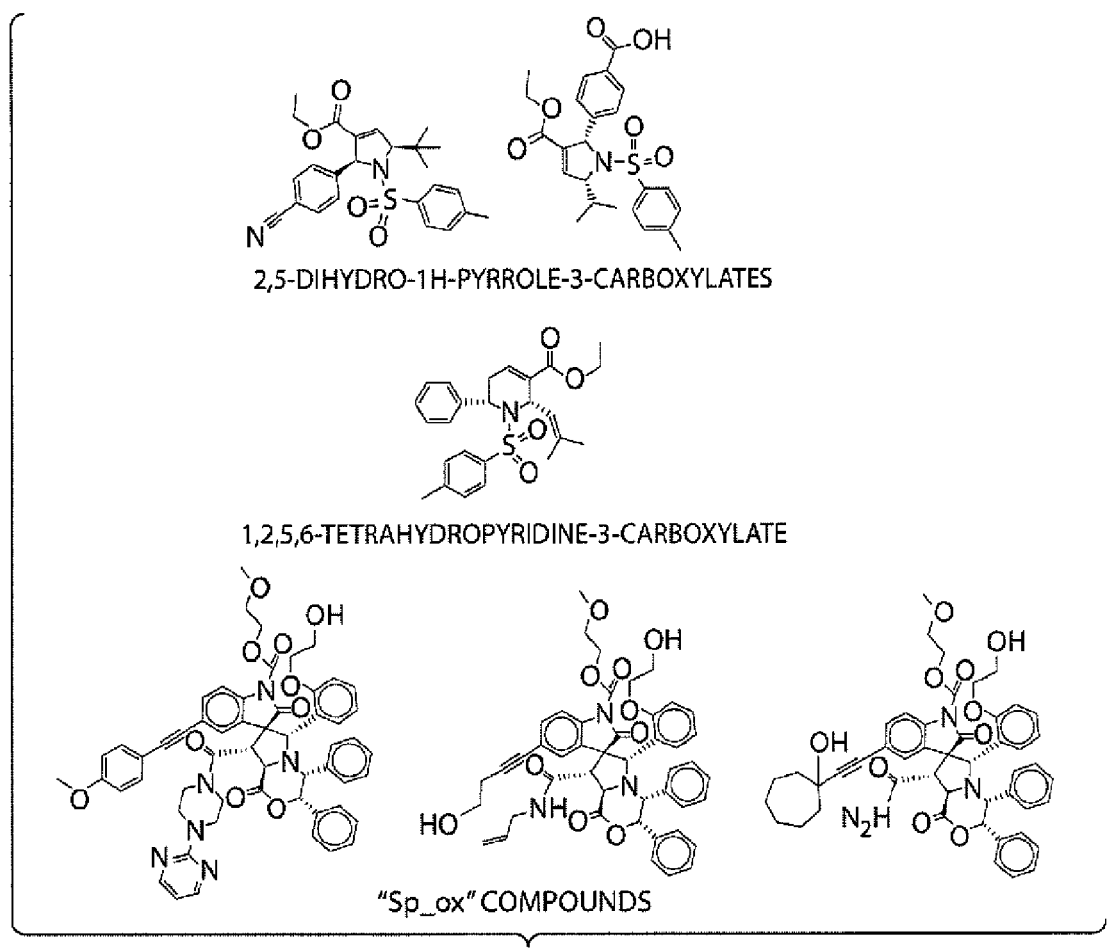
Figure 22B:
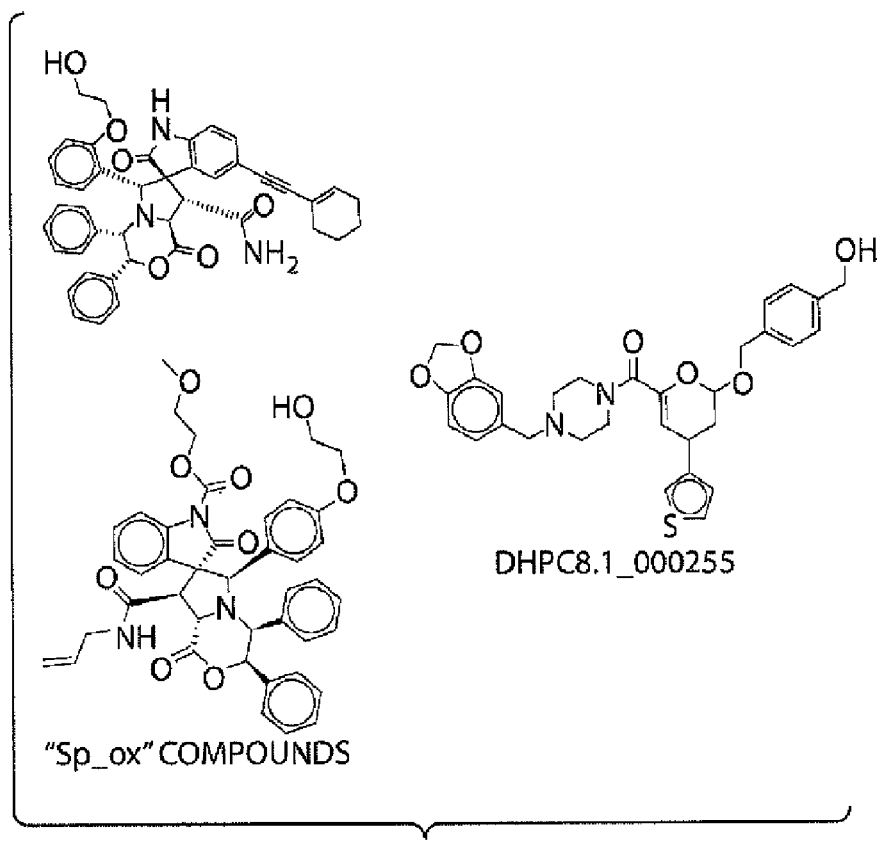
Figure 22C:
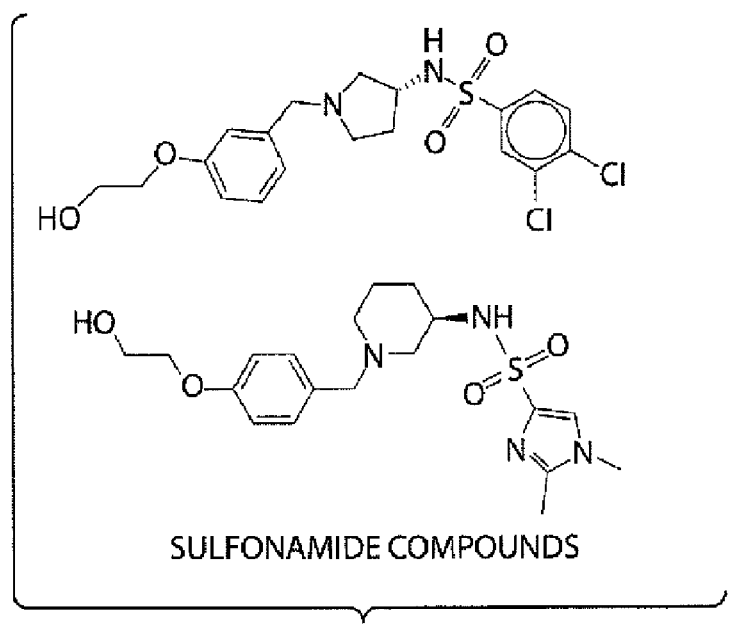

FIG. 22 shows the structures of small molecules that bind to DISC1.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); Wilen, Tables of *Resolving Agents and Optical Resolutions* p. 268 (E. L. Eliel, Ed., Univ. of Notre Dame Press, Notre Dame, Ind. 1972).

It will be appreciated that the compounds of the present invention, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The present invention contemplates any and all such combinations in order to arrive at a stable substituent/moiety. Additional examples of generally applicable substitutents are illustrated by the specific embodiments shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety.

The term "acyl," as used herein, refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)Rx, —C(=S)N(R1)$_2$, and —C(=S)S(R$^{X1}$), C(=NR$^{X1}$)R$^{X1}$, C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "aliphatic," as used herein, includes both saturated and unsaturated, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more sustitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some 10 embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "amino," as used herein, refers to a group of the formula (—NH$_2$). A "substituted amino" refers either to a mono-substituted amine (—NHR$^h$) of a disubstitued amine (—NR$^h{}_2$), wherein the R$^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the R$^h$ substituents of the di-substituted amino group (—NR$^h{}_2$) form a 5- to 6-membered hetereocyclic ring.

The term "alkoxy" refers to a "substituted hydroxyl" of the formula (—OR$^i$), wherein R$^i$ is an optionally substituted alkyl group, as defined herein, and the oxygen moiety is directly attached to the parent molecule.

The term "alkylamino" refers to a "substituted amino" of the formula (—NR$^h{}_2$), wherein R$^h$ is, independently, a hydrogen or an optionally substituted alkyl group, as defined herein, and the nitrogen moiety is directly attached to the parent molecule.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The terms "halo" and "halogen" as used herein refer to an atom selected from fluorine (fluoro, —F), chlorine (chloro, —Cl), bromine (bromo, —Br), and iodine (iodo, —I).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "hydroxy," or "hydroxyl," as used herein, refers to a group of the formula (—OH). A "substituted hydroxyl" refers to a group of the formula (—OR$^i$), wherein R$^i$ can be any substitutent which results in a stable moiety (e.g., a suitable hydroxylprotecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "stable moiety," as used herein, preferably refers to a moiety which possess stability sufficient to allow manufacture, and which maintains its integrity for a sufficient period of time to be useful for the purposes detailed herein.

A "suitable amino protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ),1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl) propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE),5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N$^2$-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES),9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable carboxylic acid protecting group," or "protected carboxylic acid," as used herein, are well known in the art and include those described in detail in Greene (1999). Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "suitable hydroxylprotecting group" as used herein, is well known in the art and include those described in detail in Greene (1999). Suitable hydroxylprotecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl) methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

A "suitable thiol protecting group," as used herein, are well known in the art and include those described in detail in

*Protecting Groups in Organic Synthesis*, T. W. Greene and P. G. M. Wuts, 3rd edition, John Wiley & Sons, 1999, the entirety of which is incorporated herein by reference. Examples of suitably protected thiol groups further include, but are not limited to, thioesters, carbonates, sulfonates allyl thioethers, thioethers, silyl thioethers, alkyl thioethers, arylalkyl thioethers, and alkyloxyalkyl thioethers. Examples of suitable ester groups include formates, acetates, proprionates, pentanoates, crotonates, and benzoates. Specific examples of suitable ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl groups include trimethylsilyl, triethylsilyl, t-butyldimethylsilyl, t-butyldiphenylsilyl, triisopropylsilyl ether, and other trialkylsilyl ethers. Examples of suitable alkyl groups include methyl, benzyl, p-methoxybenzyl, 3,4-dimethoxybenzyl, trityl, t-butyl, and allyl ether, or derivatives thereof. Examples of suitable arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

The term "thio," or "thiol," as used herein, refers to a group of the formula (—SH). A "substituted thiol" refers to a group of the formula (—SR$^r$), wherein R$^r$ can be any substituent that results in the formation of a stable moiety (e.g., a suitable thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

As used herein, the term "pharmaceutically acceptable salt" refers to those salts which are, within the scope of sound medical judgment, suitable for use in contact with the tissues of humans and lower animals without undue toxicity, irritation, immunological response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

DETAILED DESCRIPTION

The invention, in some aspects, relates to methods of treating neurological disorders by activating the DISC1 pathway in a subject. Activation of the DISC1 pathway may result, for instance, in the promotion of neurogenesis in adult neural progenitor cells.

The Disrupted In Schizophrenia 1 (DISC1) gene was initially identified as being disrupted by a balanced chromosomal translocation (1; 11) (q42; q14.3) in a large Scottish family with a high incidence of major depression, schizophrenia and bipolar disorder. To date, alterations in DISC1 have been found throughout its entire coding sequence (Chubb, J. E., Bradshaw, N.J., Soares, D.C., Porteous, D. J. & Millar, J. K. The DISC locus in psychiatric illness. Mol Psychiatry 13, 36-64 (2008)). Some of these mutations affect interactions with DISC1 binding partners. For instance, the Scottish truncated protein loses interaction with NdeI/Lis1 (Morris, J. A., Kandpal, G., Ma, L. & Austin, C. P. DISC1 is a centrosome-associated protein that interacts with MAP1A, MIPT3, ATF4/5 and NUDEL: regulation and loss of interaction with mutation. Hum Mol Genet. 12, 1591-608 (2003)), and point mutations in exon 2 affect binding to PDE4B (Clapcote, S. J. et al. Behavioral phenotypes of Disc1 missense mutations in mice. Neuron 54, 387-402 (2007)).

It has now been discovered according to aspects of the invention that suppression of DISC1 reduces proliferation of neural progenitors, leading to premature cell cycle exit and differentiation. Conversely, DISC1 gain-of-function promotes progenitor proliferation. The evidence described herein imply that DISC1 mediates this function through regulation of GSK3β, an important mediator of Wnt signaling. Wnt3a-stimulated proliferation is blocked by silencing DISC1 expression, and both gain- and loss-of-function experiments imply that DISC1 controls β-catenin/TCF-dependent transactivation. Furthermore, DISC1 directly interacts with GSK3β and inhibits its activity, resulting in stabilization of β-catenin. Finally, both GSK3β inhibitors and expression of stabilized β-catenin can override the impairment of progenitor proliferation caused by DISC1 loss-of-function. Together, these results indicate that DISC1 facilitates neural progenitor proliferation by negatively regulating GSK3β. These data provide a framework for understanding how alterations in neural progenitor proliferation may play a role in the etiology of psychiatric disorders.

Emerging evidence supports a neurodevelopmental basis for schizophrenia (Ross, C. A., Margolis, R. L., Reading, S. A., Pletnikov, M. & Coyle, J. T. Neurobiology of schizophrenia. Neuron 52, 139-53 (2006); Chubb, J. E., Bradshaw, N.J., Soares, D.C., Porteous, D. J. & Millar, J. K. The DISC locus in psychiatric illness. Mol Psychiatry 13, 36-64 (2008); Arnold, S. E. Neurodevelopmental abnormalities in schizophrenia: insights from neuropathology. Dev Psychopathol 11, 439-56 (1999)). Gestational disruption of brain development in rats leads to a reduction of prefrontal cortex and hippocampus size, resulting in schizophrenic behavior changes (Flagstad, P. et al. Disruption of neurogenesis on gestational day 17 in the rat causes behavioral changes relevant to positive and negative schizophrenia symptoms and alters amphetamine-induced dopamine release in nucleus accumbens. Neuropsychopharmacology 29, 2052-64 (2004); Flagstad, P., Glenthoj, B. Y. & Didriksen, M. Cognitive deficits caused by late gestational disruption of neurogenesis in rats: a preclinical model of schizophrenia. Neuropsychopharmacology 30, 250-60 (2005)). In schizophrenia patients, decreases in neural stem cell proliferation have been reported (Reif, A. et al. Neural stem cell proliferation is decreased in schizophrenia, but not in depression. Mol Psychiatry 11, 514-22 (2006)). Moreover, anti-psychotics increase neurogenesis in the hippocampus (Newton, S. S. & Duman, R. S, Neurogenic actions of atypical antipsychotic drugs and therapeutic implications. CNS Drugs 21, 715-25 (2007); Maeda, K. et al. Clozapine prevents a decrease in neurogenesis in mice repeatedly treated with phencyclidine. J Pharmacol Sci 103, 299-308 (2007)).

The data described herein demonstrate the important role of the DISC1 pathway in psychiatric disorders. FIG. 15 is a schematic depicting the pathway and its role in disease. It is shown herein that DISC1 is essential for neural progenitor proliferation in the SVZ/VZ of mouse embryonic brains and in the dentate gyrus of adult brains. Furthermore, this reduction in proliferation was accompanied by an increase in cell cycle exit, leading to a premature depletion of the progenitor pool and reduction in the quantity of neurons produced. Thus, as depicted in FIG. 15, DISC1 loss-of-function may tip the balance between progenitor proliferation and neuronal differentiation, ultimately impacting the production of certain classes of neurons and predisposing to an increased risk for psychiatric disorders.

Although DISC1 has been associated with schizophrenia in the literature, the biochemical pathways that enable DISC1 have been poorly understood prior to the instant invention. For example, the (1; 11) (q42; q14.3) translocation allele of the DISC1 gene closely segregates with the manifestation of psychiatric disorders in a large Scottish pedigree (Blackwood, D. H. et al. Schizophrenia and affective disorders—cosegregation with a translocation at chromosome 1q42 that directly disrupts brain-expressed genes: clinical and P300 findings in a family. Am J Hum Genet. 69, 428-33 (2001)). Multiple haplotypes and SNPs along this gene are associated with bipolar disorder (Hodgkinson, C. A. et al. Disrupted in schizophrenia 1 (DISC1): association with schizophrenia, schizoaffective disorder, and bipolar disorder. Am J Hum Genet. 75, 862-72 (2004)), schizophrenia (Hodgkinson, C. A. et al. Disrupted in schizophrenia 1 (DISC1): association with schizophrenia, schizoaffective disorder, and bipolar disorder. Am J Hum Genet. 75, 862-72 (2004)) and autism spectrum disorders (Kilpinen, H. et al. Association of DISC1 with autism and Asperger syndrome. Mol Psychiatry (2007)). Over-expression of the DISC1 Scottish mutant (Pletnikov, M. V. et al. Inducible expression of mutant human DISC1 in mice is associated with brain and behavioral abnormalities reminiscent of schizophrenia. Mol Psychiatry (2007); Hikida, T. et al. Dominant-negative DISC1 transgenic mice display schizophrenia-associated phenotypes detected by measures translatable to humans. Proc Natl Acad Sci USA 104, 14501-6 (2007)) or the C-terminal portion of DISC1 (Li, W. et al. Specific developmental disruption of disrupted-in-schizophrenia-1 function results in schizophrenia-related phenotypes in mice. Proc Natl Acad Sci USA 104, 18280-5 (2007)) in mouse brains result in behavioral phenotypes reminiscent of schizophrenia. Likewise, point mutations in exon 2 of mouse DISC1 lead to the manifestation of schizophrenia-like or depression-like behaviors (Clapcote, S. J. et al. Behavioral phenotypes of Disc1 missense mutations in mice. Neuron 54, 387-402 (2007)). Furthermore, the 129 strain of mice contain a deletion in exon7 of DISC1 and display a working memory deficit (Koike, H., Arguello, P. A., Kvajo, M., Karayiorgou, M. & Gogos, J. A. Disc1 is mutated in the 129S6/SvEv strain and modulates working memory in mice. Proc Natl Acad Sci USA 103, 3693-7 (2006)).

To date, several proteins have been shown to interact with DISC1 including NudE-like 1 (Ndel1) (Morris, J. A., Kandpal, G., Ma, L. & Austin, C. P. DISC1 (Disrupted-In-Schizophrenia 1) is a centrosome-associated protein that interacts with MAPLA, MIPT3, ATF4/5 and NUDEL: regulation and loss of interaction with mutation. Hum Mol Genet. 12, 1591-608 (2003)), L is 1, phosphodiesterase 4B (PDE4B) (Millar, J. K. et al. DISC1 and PDE4B are interacting genetic factors in schizophrenia that regulate cAMP signaling. Science 310, 1187-91 (2005)), and the transcription factors ATF4 and ATF5 (Morris, J. A., Kandpal, G., Ma, L. & Austin, C. P. DISC1 (Disrupted-In-Schizophrenia 1) is a centrosome-associated protein that interacts with MAPLA, MIPT3, ATF4/5 and NUDEL: regulation and loss of interaction with mutation. Hum Mol Genet. 12, 1591-608 (2003)). Functional studies revealed that DISC1 is involved in neurite outgrowth (Ozeki, Y. et al. Disrupted-in-Schizophrenia-1 (DISC-1): mutant truncation prevents binding to NudE-like (NUDEL) and inhibits neurite outgrowth. Proc Natl Acad Sci USA 100, 289-94 (2003)), neuronal migration (Kamiya, A. et al. A schizophrenia-associated mutation of DISC1 perturbs cerebral cortex development. Nat Cell Biol 7, 1167-78 (2005); Duan, X. et al. Disrupted-In-Schizophrenia 1 regulates integration of newly generated neurons in the adult brain. Cell 130, 1146-58 (2007)), integration of newborn neurons (Duan, X. et al. Disrupted-In-Schizophrenia 1 regulates integration of newly generated neurons in the adult brain. Cell 130, 1146-58 (2007)), and cAMP signaling (Millar, J. K. et al. DISC1 and PDE4B are interacting genetic factors in schizophrenia that regulate cAMP signaling. Science 310, 1187-91 (2005)).

Since it has now been shown according to the invention that multiple domains of DISC1 interact with and inhibit GSK3β, it is expected that compounds which affect the DISC1 pathway and thus, affect this interaction are useful in the treatment of neurological disorders. Thus, in some aspects, the invention relates to a method for treating a neurological disorder in a subject by administering to the subject a DISC1 pathway activator in an effective amount to treat the neurological disorder.

A DISC1 pathway activator as used herein refers to a compound that activates DISC1 pathway and promotes neurogenesis in adult neural progenitor cells. As used herein the term "DISC1 pathway" includes but is not limited to the genes, nucleotides, and polypeptides associated with DISC1, GSK3, and β-catenin as well as upstream or downstream components that contribute to the interaction between DISC1 and GSK3 or are influenced by the interaction between DISC1 and GSK3 respectively.

The terms "DISC1", "GSK3" and "β-catenin" shall be understood to encompass the associated polynucleotides and polypeptides. DISC1 has been previously described. See, in particular, Millar et al., Human Molecular Genetics 2000, 9:1415-1423 and GenBank Accession No. AF222980; GI:8163868. The nucleic acid and peptide sequences for DISC1 are set forth in US Patent Application 2003/0054345, which is incorporated herein by reference for such teachings.

GSK3 (Glycogen synthase kinase 3) is a proline-directed serine/threonine kinase originally identified as having an activity that phosphorylates glycogen synthase. GSK3 includes two isoforms, α and β, both of which are both encompassed by the term GSK3 as used herein. In some embodiments the β isoform is preferred. GSK3 which is constitutively active in resting cells can be inactivated by growth factors or hormones that signal through receptor tyrosine kinases. GSK3 has been shown, for instance, to phosphorylate β-catenin. The nucleic acid and protein sequences of GSK3 are described, for instance, in Genbank XM 029918 (human GSK-3α), Genbank L33801 (human GSK-3β), and US Patent Application No. 2003/0163836, which are incorporated by reference for such teachings.

β-catenin is a cytoplasmic protein that is critical for classical cadherin-mediated intercellular adhesion. Inside the cell, a β-catenin /α-catenin complex interacts with the second cytoplasmic domain (CP2) of the classical cadherins. In addition to its role in cell adhesion, β-catenin is also a key component of certain cellular signaling pathways, leading to activation of gene expression and a variety of developmental and disease processes. In particular, β-catenin functions in Wnt-mediated signaling, associating with LEF-1/TCF DNA binding proteins to form a transcription factor (see Willert and Nusse, Genetics and Development 8:95-102, 1998).

DISC1 pathway activators include but are not limited to DISC1 activators, GSK3 inhibitors, and GSK3 expression inhibitors. A "DISC1 activator" as used herein refers to a molecule that increases the expression level or activity of DISC1 or functionality of DISC1 relative to the level prior to treatment. DISC1 activators include but are not limited to DISC1 inducing agents, DISC1 agonists, agents that promote DISC1-GSK3 binding or DISC1 agonist-GSK3 binding. Increasing the functionality of DISC1 refers to mimicking DISC1 activity on it's targets, such as by inhibiting GS K3 through a DISC1 related mechanism. DISC1 activators do not include FEZ1 inhibitors, AKT inhibitors, GSK3 inhibitors or β-catenin inhibitors that act directly on FEZ1, AKT, GSK3 and β-catenin respectively, other than through a DISC1 mechanism, such as binding of DISC1 or a DISC1 agonist to the target. Although DISC1 activators may influence activity or expression levels of AKT, GSK3 and β-catenin by acting upstream of such molecules, such as lithium, they are not considered to be inhibitors of AKT, GSK3 and β-catenin.

A DISC1 inducing agent as used herein refers to a compound that promotes endogenous DISC1 function. The DISC1 inducing agent may function, for example, by inducing the expression levels of endogenous DISC1, by stabilizing the DISC1 protein, by preventing a decrease in DISC1 activity or by increasing the activity of DISC1 protein. Inducing agents include for instance upstream activators of DISC1 as well as compounds that block DISC1 inhibitors.

A DISC1 agonist as used herein refers to a compound that interacts with GSK3 or produces a compound that interacts with GSK3 and inhibits GSK3 activity. DISC1 agonists include for instance but are not limited to exogenous DISC1 nucleic acids or polypeptides, DISC1 fragments, and peptide mimetics.

A DISC1 fragment is a peptide that is identical to or at least 90% homologous to less than the full length DISC1 peptide, referred to herein as a portion of DISC1. The full length peptide sequence of human DISC1 is presented as SEQ ID NO. 11 (derived from genbank) and the nucleic acid sequence is presented as SEQ ID NO. 12. Variants of such sequences can be identified by the skilled artisan. The portion of DISC1 is representative of the full length DISC1 polypeptide. A fragment is representative of the full length DISC1 polypeptide if it includes at least 10 amino acids (contiguous or non-contiguous) of the DISC1 polypeptide and binds to GSK3. In some embodiments the portion is less than 90% of the entire native human DISC1 polypeptide. In other embodiments the portion is less than 50%, 45%, 40%, 35%, 30%, 25%, 20%, 15%, 10%, or 5% of the entire native human DISC1 polypeptide.

Thus, in some instances the DISC1 fragments is identical to a portion of the native human DISC1 polypeptide. Alternatively, the DISC1 fragment may be at least 90% homologous to a portion of the native human DISC1 polypeptide. In preferred embodiments the DISC1 fragment may be at least 95%, 96%, 97%, 98%, or 99% homologous to a portion of the native human DISC1 polypeptide. As shown in the examples below fragments of DISC1 corresponding to amino acids 1-220, 221-355 ad 356-595 are all able to inhibit GSK3 activity. The fragment corresponding to amino acids 1-220 was the most potent in inhibiting GSK3 activity, at least in the assays used herein.

An example of a DISC1 fragment is human peptide 2. Human DISC1 peptide 2 corresponds to amino acids 193-236 of human DISC1 and has the following sequence PEVPPT-PPGSHSAFTSSFSFIRLSLGSAGERGEAEGCPPSREAE (SEQ ID NO: 8). Another DISC1 fragment is murine DISC1 peptide 2 (195-238aa, PADIASLPGFQDTFTSSFSFIQLSL-GAAGERGEAEGCLPSREAE (SEQ ID NO: 2). Another example of a DISC1 fragment is human peptide 3. Human DISC1 peptide 3 corresponds to amino acids 211-225 of human DISC1 and has the following sequence SFIRLSLG-SAGERGE (SEQ ID NO: 9). Murine DISC1 peptide 3 corresponds to amino acids 211-225 of murine DISC1 and has the following sequence SFSFIQLSLGAAGER (SEQ ID NO: 10). Other specific peptides of varying lengths can be used created from the DISC1 peptide and used according to the methods of the invention.

In addition to the peptides described herein, DISC1 agonists include peptide mimetics, which may in some instances have more favorable pharmacological properties than peptides. A DISC1 peptide mimetic is an organic compound that is structurally similar to DISC1 or a DISC1 fragment. Thus peptide mimetics ideally mimic the function of a DISC1 peptide or fragment thereof but have improved cellular transport properties, low toxicity, few side effects and more rigid structures as well as protease resistance.

Various methods for the development of peptide mimetics, including computational and screening methods, are know in the art. Review articles on such methods include for instance, Zutshi R, et al Inhibiting the assembly of protein-protein interfaces. *Cur Open Chem. Biol* 1998, 2:62-6, Cochran AG: Antagonists of protein-protein interactions. *Chem Biol* 2000, 7:R85-94, and Toogood PL: Inhibition of protein-protein association by small molecules: approaches and progress. *J Med Chem* 2002, 45:1543-58. Another approach, referred to as the supermimetic method, detects peptide mimetics directly using a known protein structure and a mimetic structure. Goede A. et al *BMC Bioinformatics* 2006, 7:11. In that method, specific atomic positions are defined in both structures and then compared with respect to their spatial conformations. In this way, organic compounds that fit into the backbone of a protein can be identified. Conversely, it is possible to find protein positions where a specific mimetic could be inserted. Using such methods it is possible to find organic compounds or design artificial peptides that imitate the binding site and hence the functionality of a protein. Programs for enabling such methods can be downloaded from the SuperMimic website (http://bioinformatics.charite.de/supermimic).

Methods for identifying peptide mimetics and other molecules that bind to a target have been described. For instance, U.S. Pat. No. 6,230,102 to Tidor et al describe a computer implemented system involving a methodology for determining properties of ligands which in turn can be used for designing ligands for binding with protein or other molecular targets. The methods involve defining the electrostatic complement for a given target site and geometry. The electrostatic complement may be used with steric complement for the target site to discover ligands through explicit construction and through the design or bias of combinatorial libraries. The methods lead to the identification of molecules having point charges that match an optimum charge distribution, which can be used to identify binding molecules. Methods using small-molecule microarrays (Bradner et al., "A method for the covalent capture and screening of diverse small molecules in a microarray format" *Nature Protocols* 1:23344-2352, 2006) may also be used to identify chemical compounds that bind a target such as DISC1. Several DISC1 variants (Long, Short, Extra Short, Mutant, Long Variant) were expressed in tissue culture cells and used to identify small molecules that bind to these variants.

Based on the screening of a library of approximately 10,000 small molecules, compounds that bind to DISC1 were identified. FIG. 22. These compounds may bind to one of more isoforms or variants of DISC1. In certain embodiments, the compound binds to one or more of the DISC1 variants (Long, Short, Extra Short, Mutant, Long Variant) as described herein. In certain embodiments, the compound binds at least one of these variants. In certain embodiments, the compound binds at least two of these variants. In certain embodiments, the compound binds at least three of these variants. In certain embodiments, the compound binds at least four of these variants. In certain embodiments, the compound binds at least five of these variants. Compounds which have been found to bind to DISC1 may be useful in the treatment or prevention of neuropsychiatric diseases. Such compounds may be useful themselves as therapeutic agents, or such compounds may be used as lead compounds in developing therapeutic agents. Such compounds may also be useful a chemical probes of the DISC1 pathway. For example, a compound may be useful in understanding the role of DISC1 in psychiatric diseases.

In certain embodiments, the compound discovered to bind DISC1 or an isoform or variant thereof is a spirooxindole compound as described in published PCT application, WO 2008/144507, published Nov. 27, 2008, which is incorporated herein by reference. In certain embodiments, spirooxindole compound have been found to bind at least 3 of the five DISC1 isoforms. In certain embodiments, the compound is of one of the formulae:

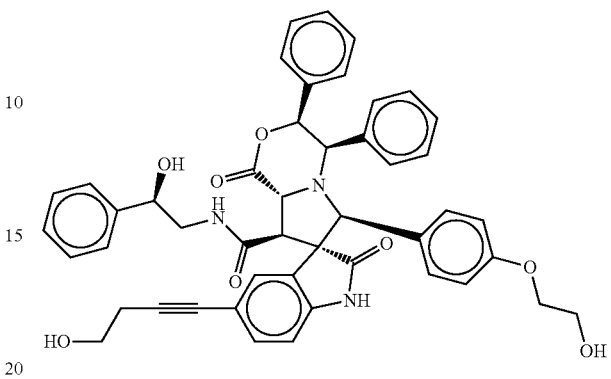

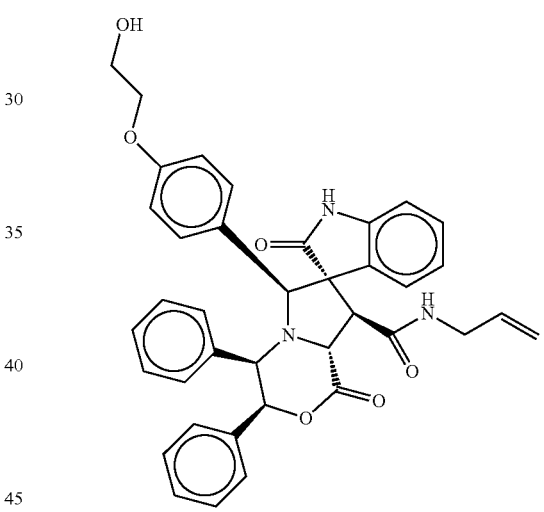

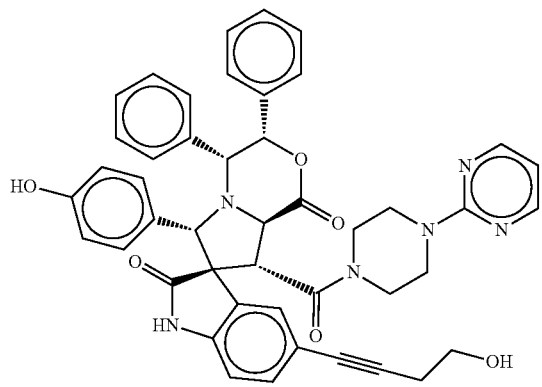

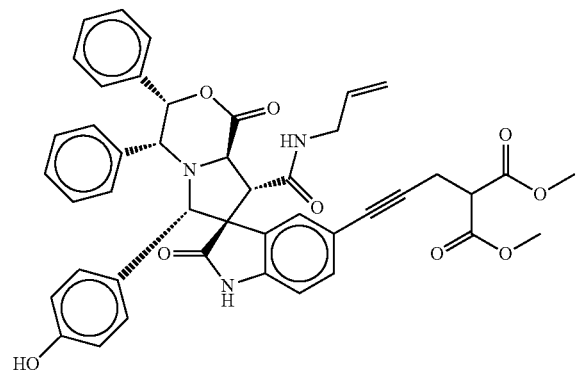

29
-continued
30
-continued
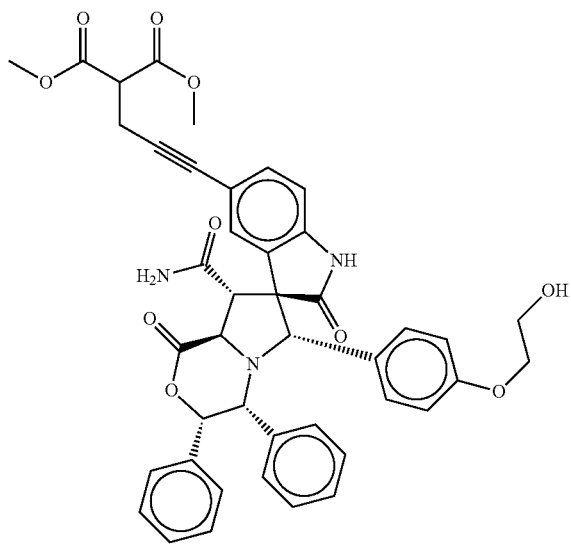
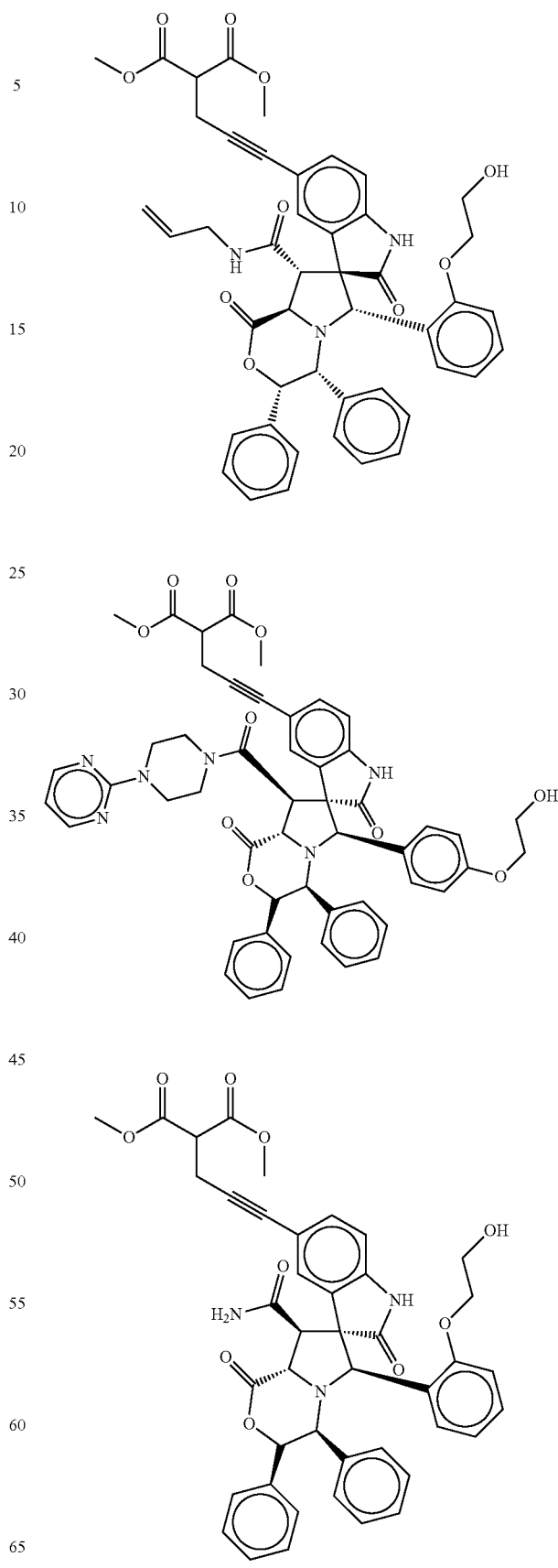

31
-continued
32
-continued
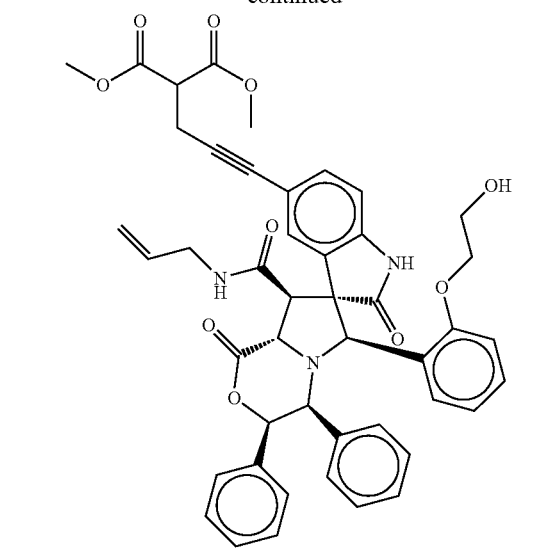
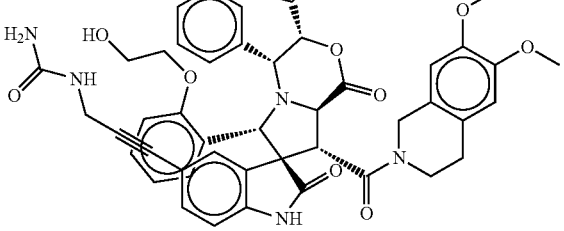
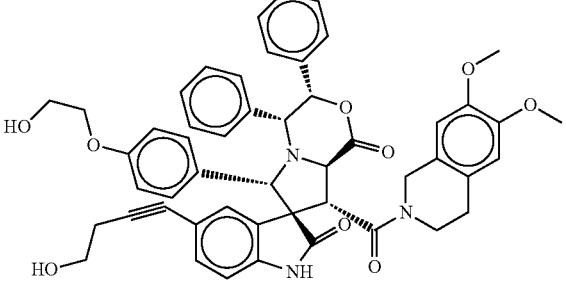
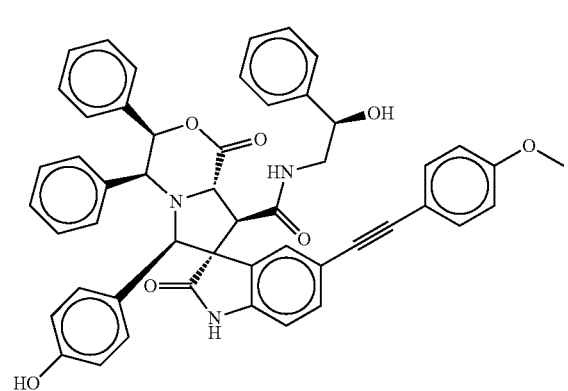
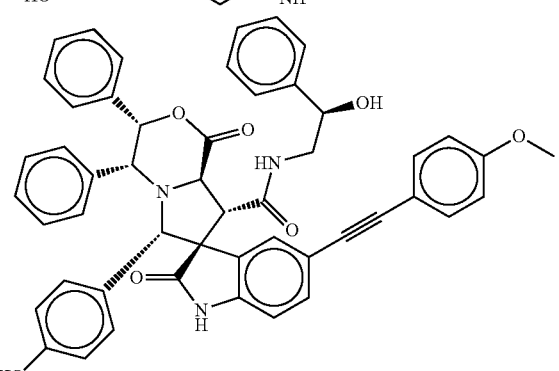
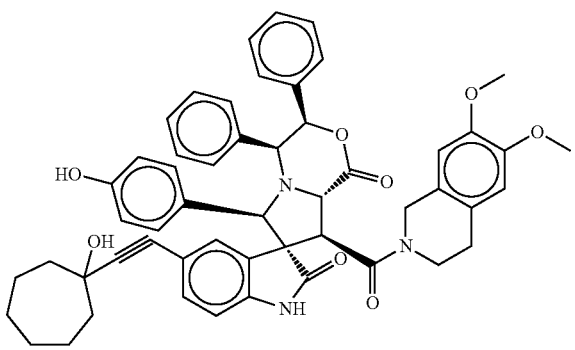
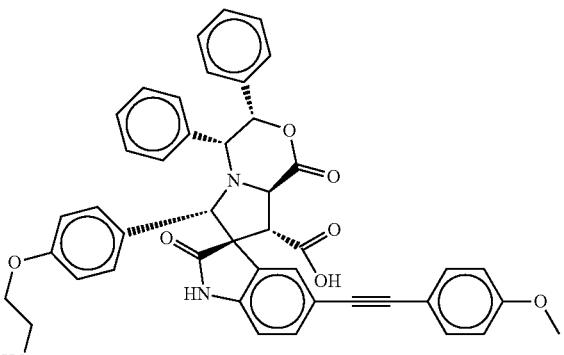
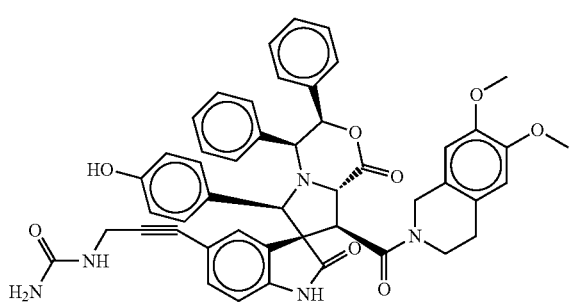
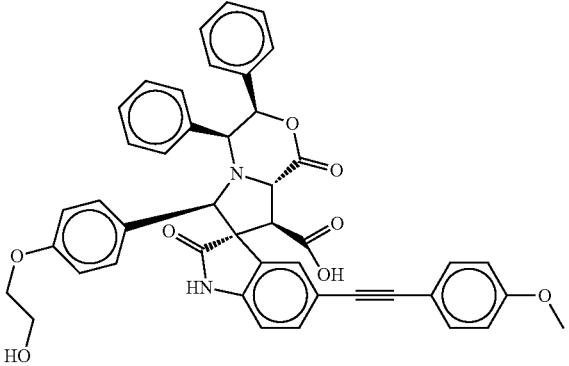

33
-continued
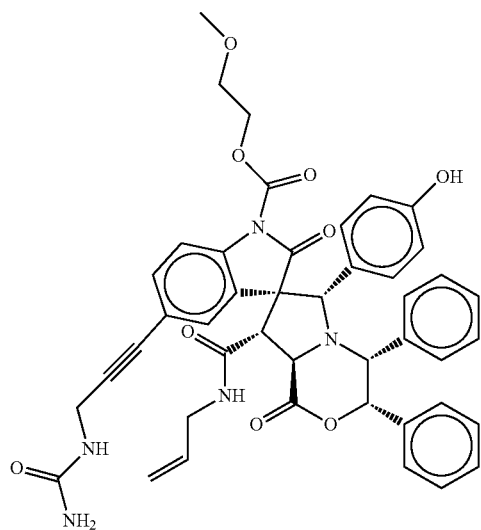
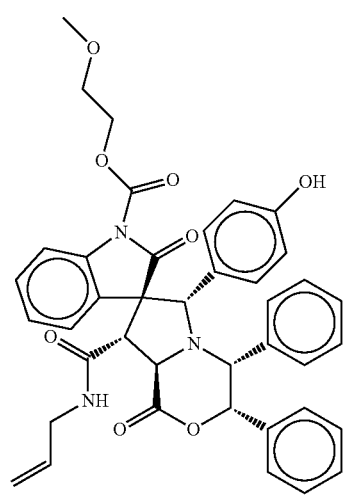
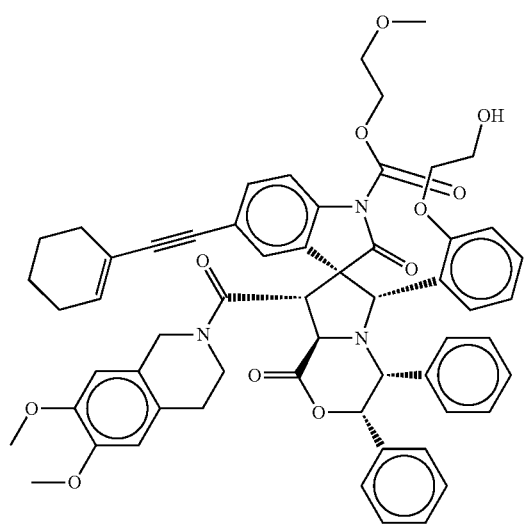
34
-continued
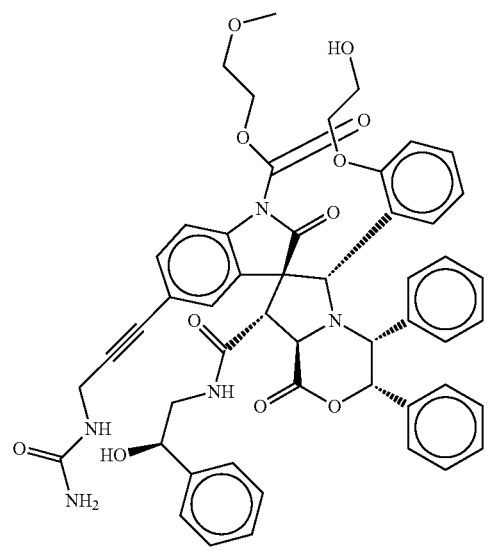
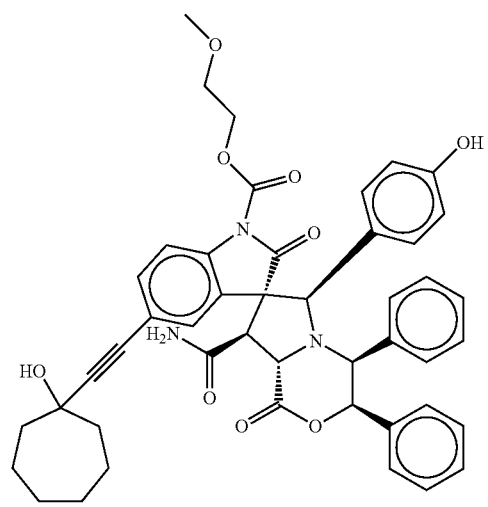
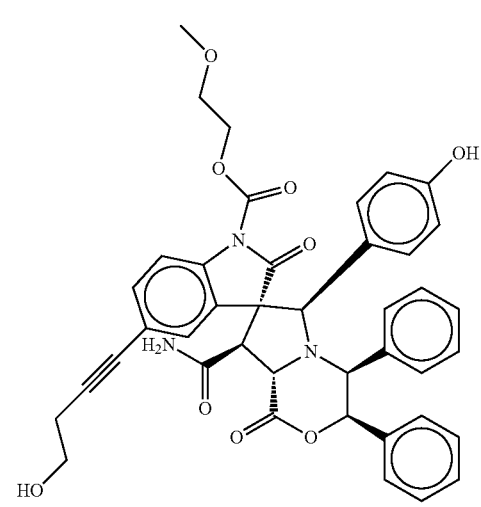

35
-continued
36
-continued
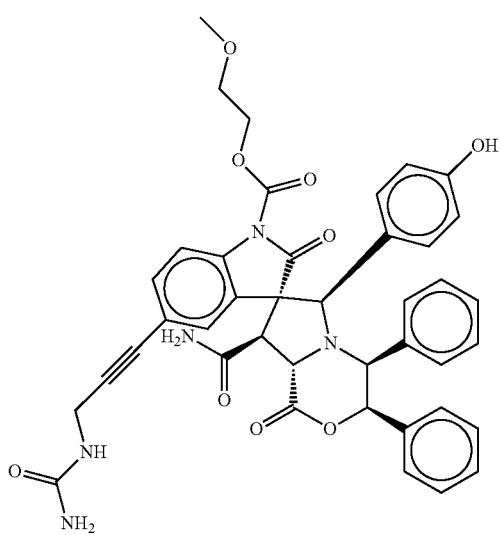
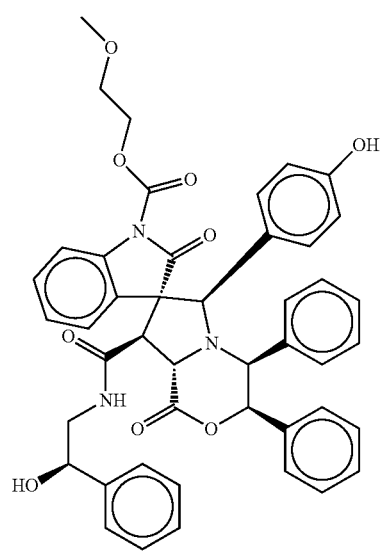
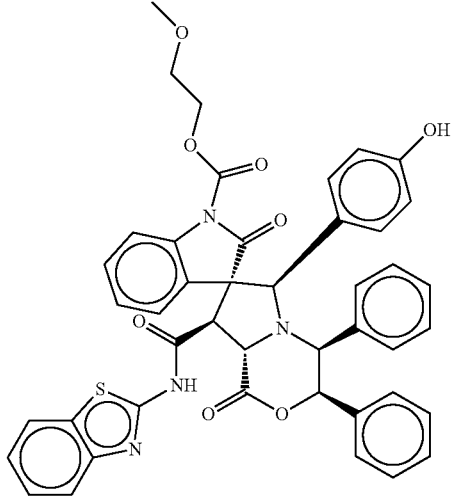
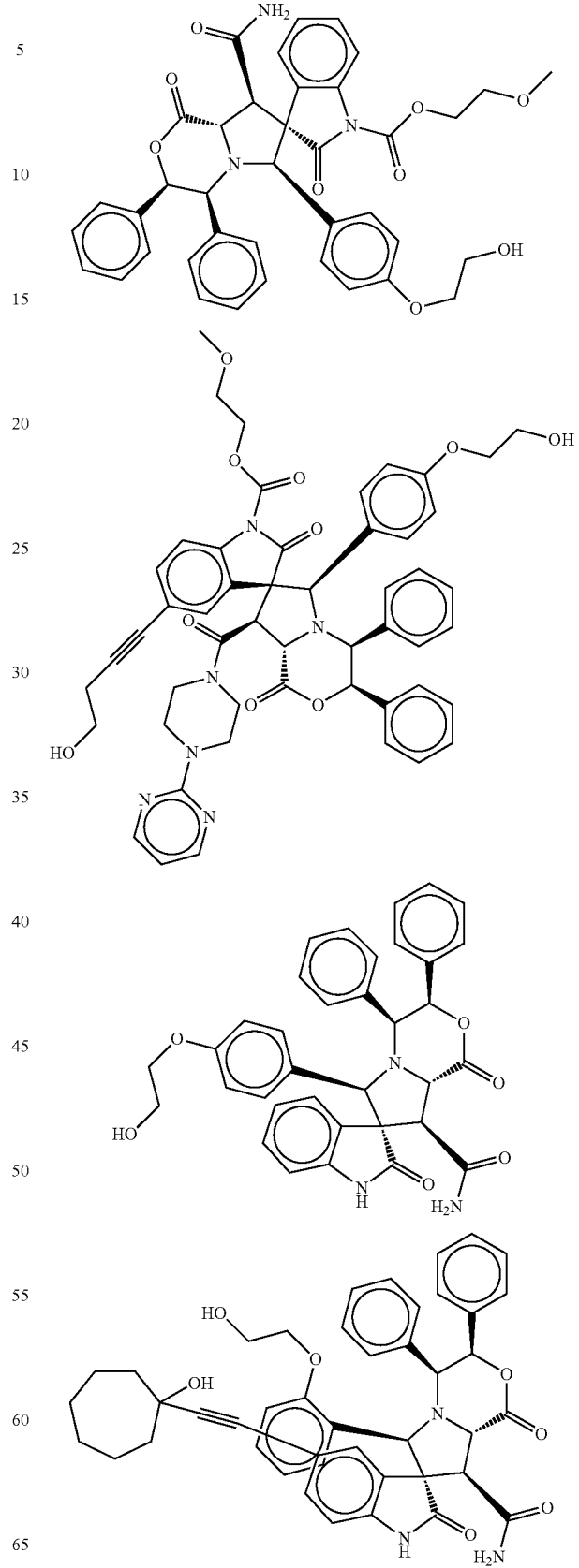

37
-continued
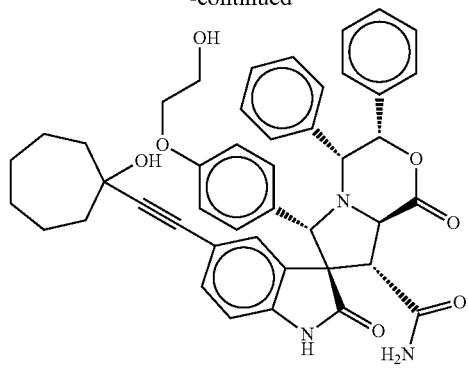
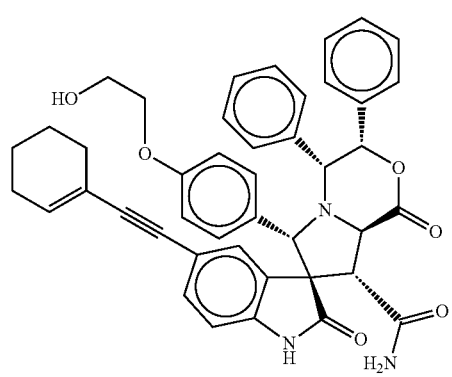
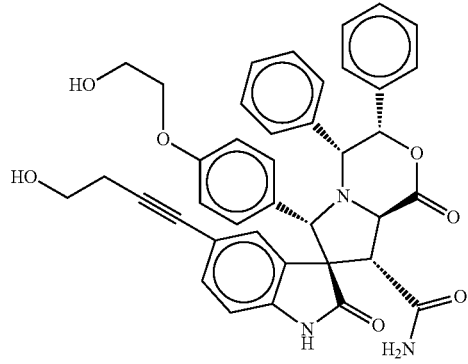
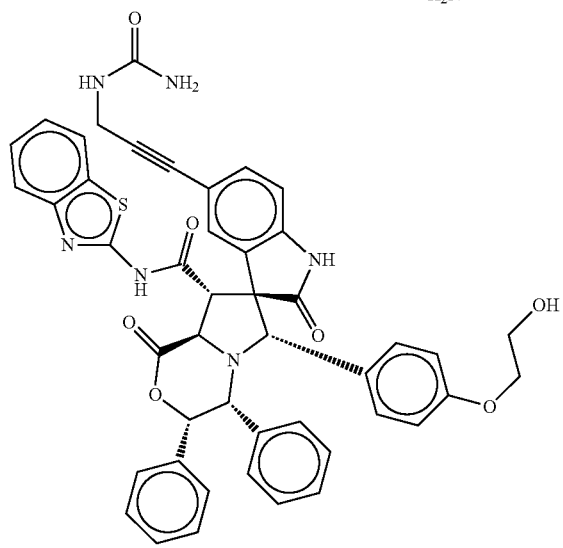
38
-continued
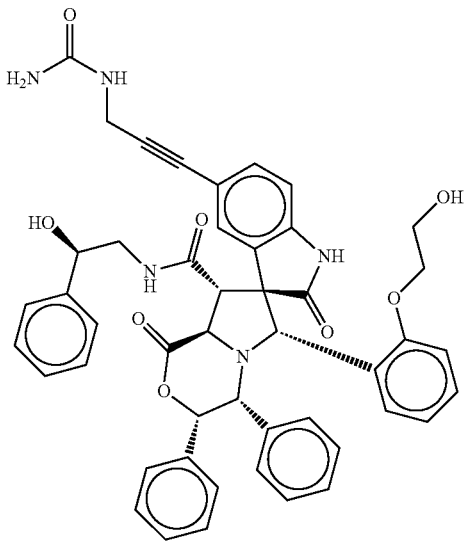
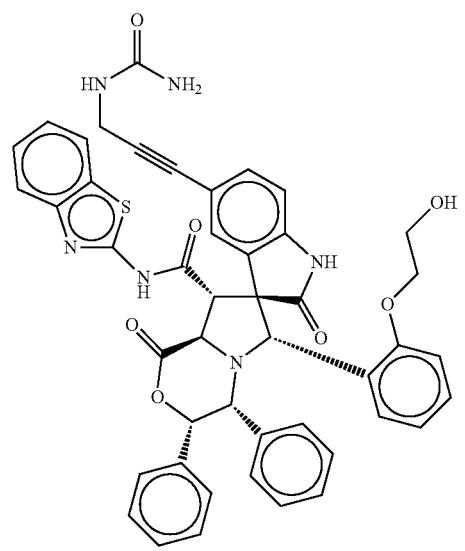
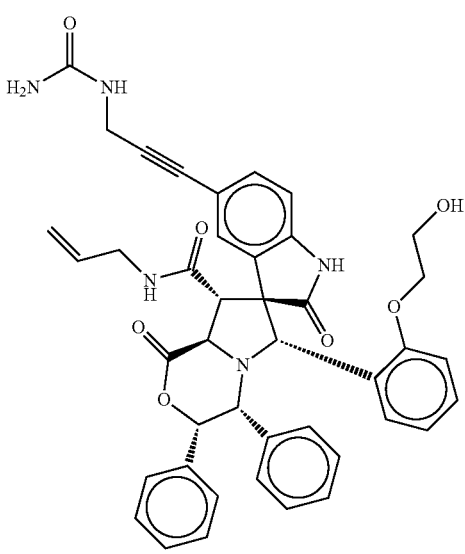

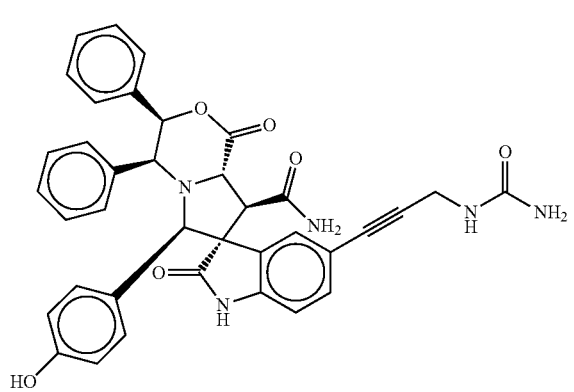
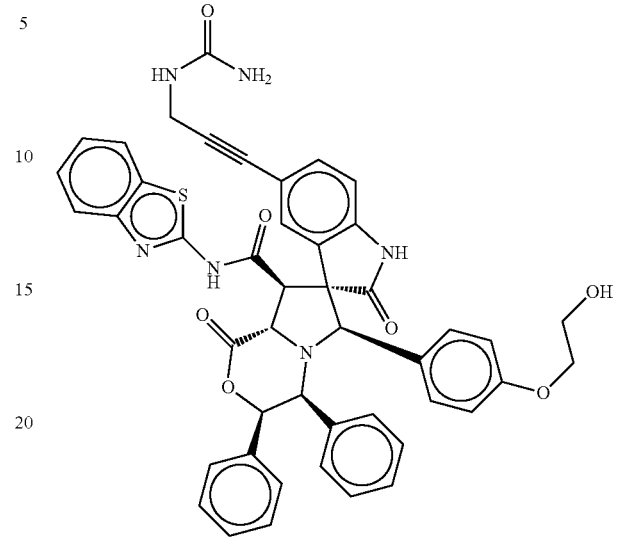
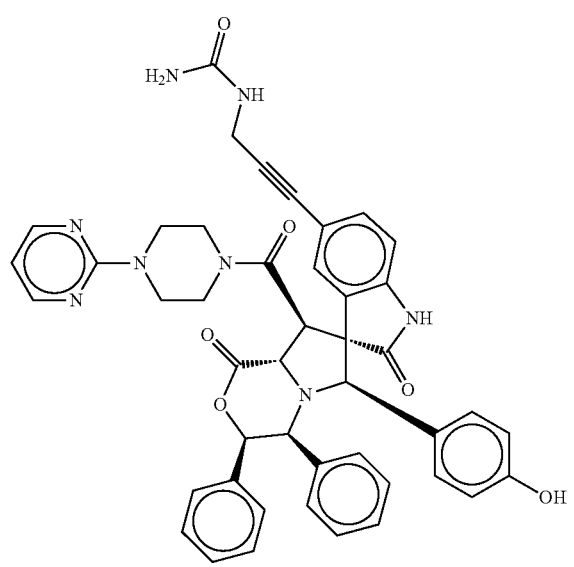
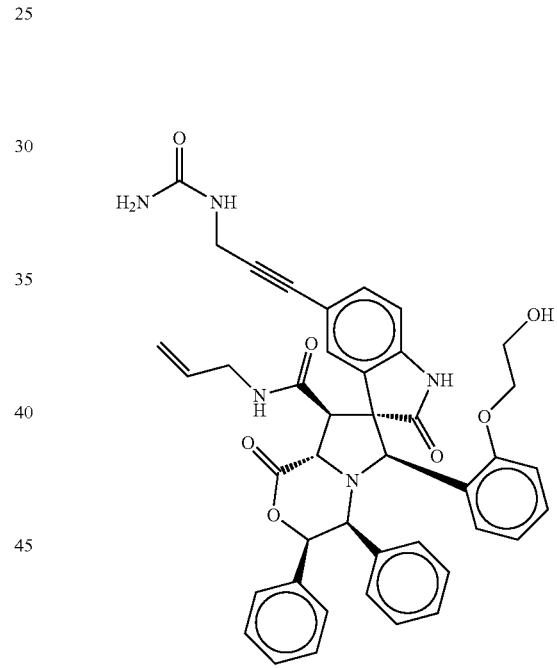
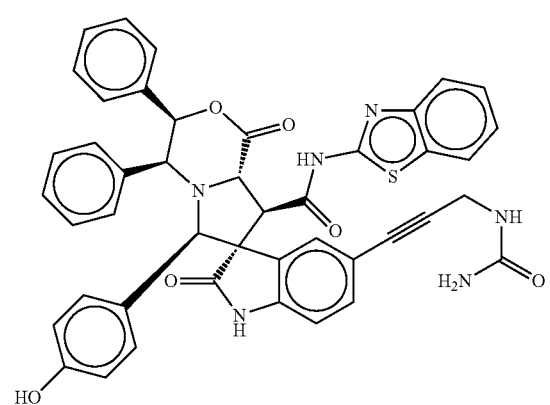
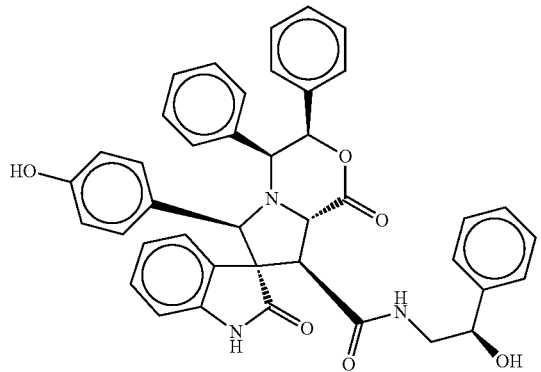

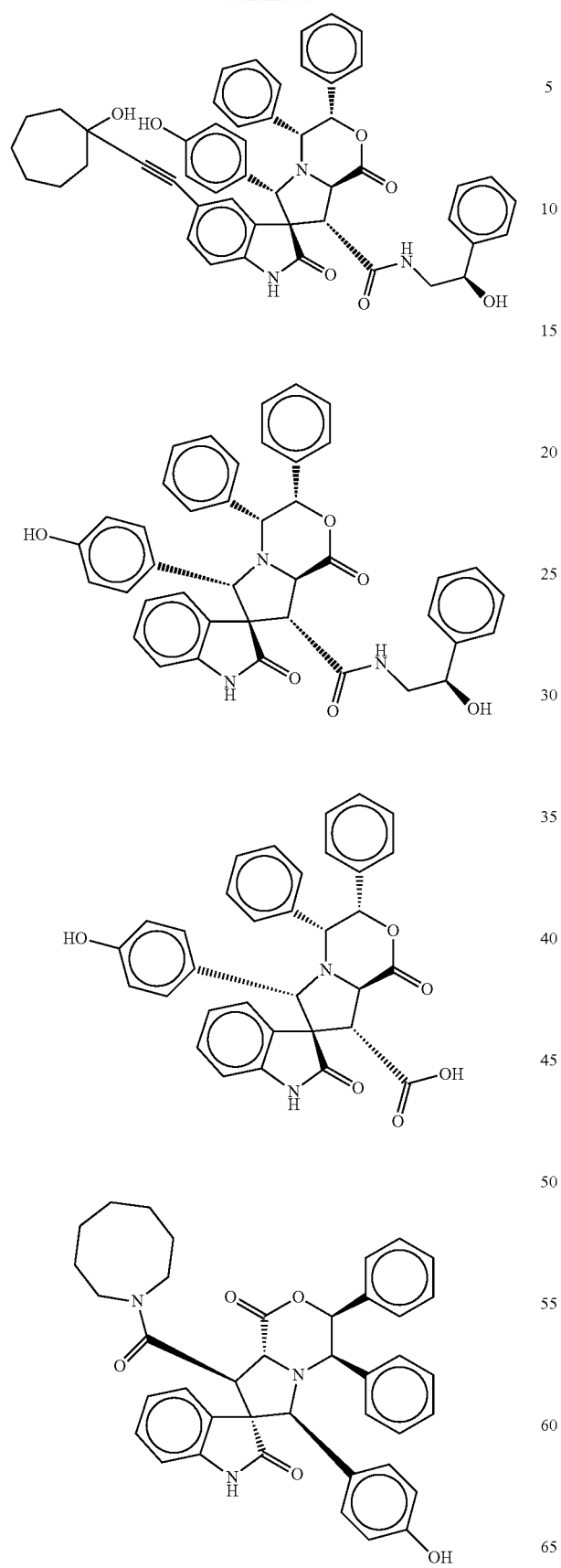
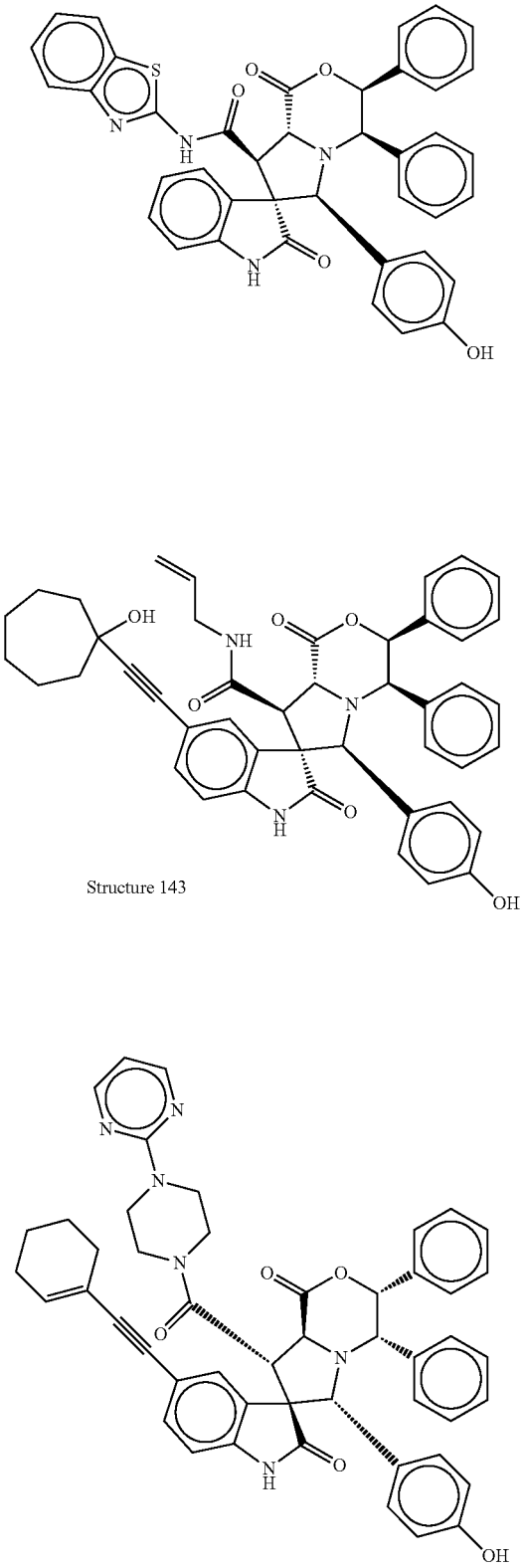
Structure 143

43
-continued
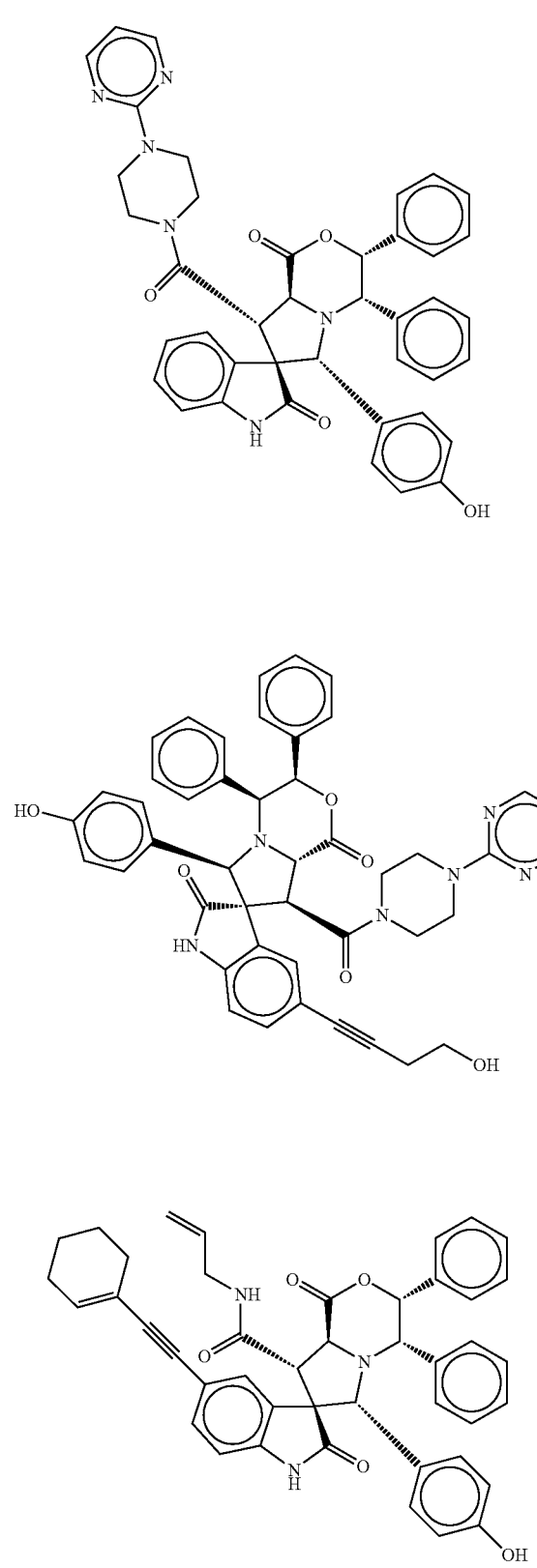
44
-continued
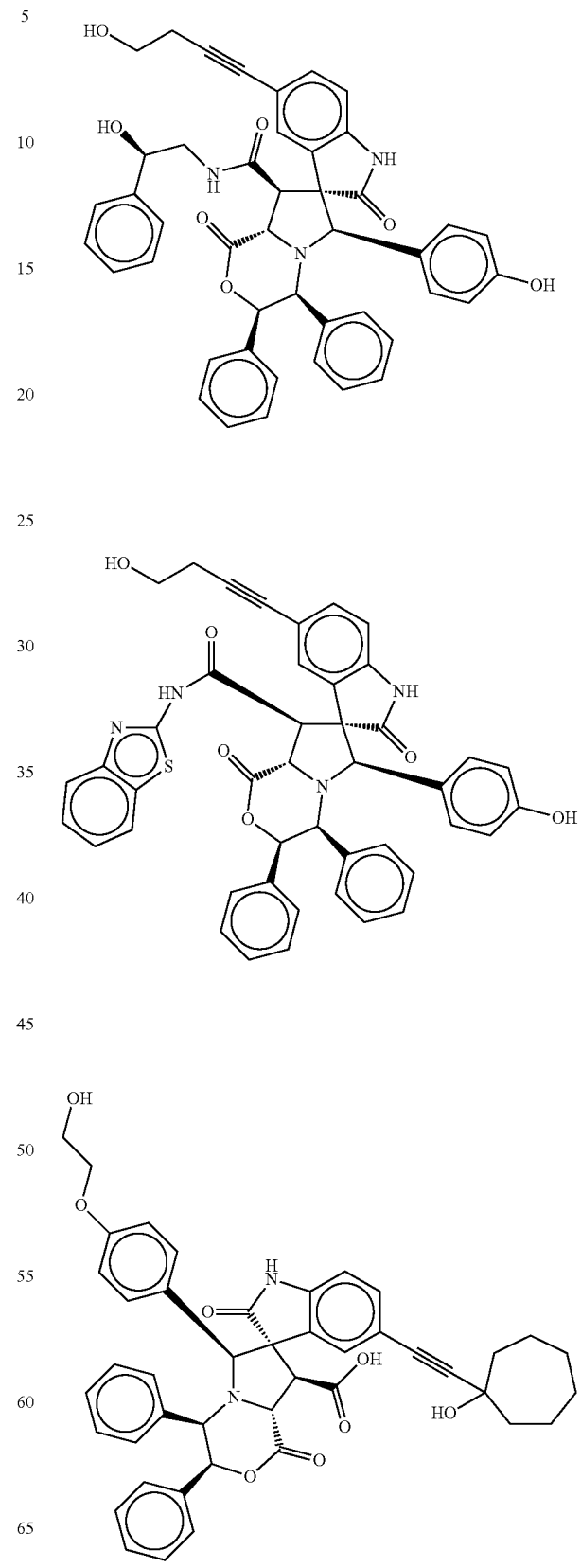

-continued
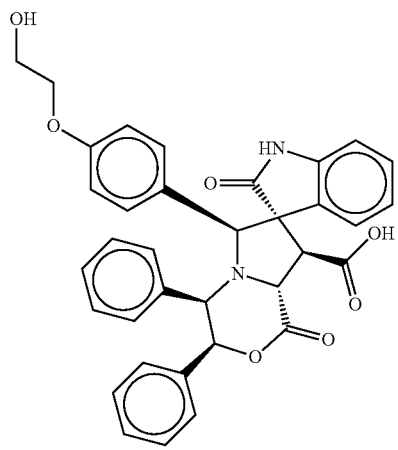
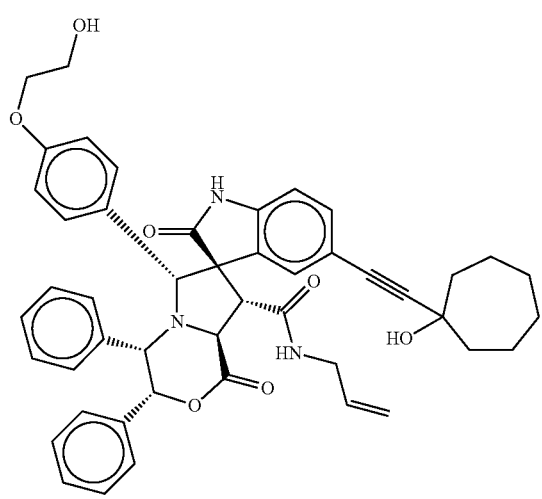
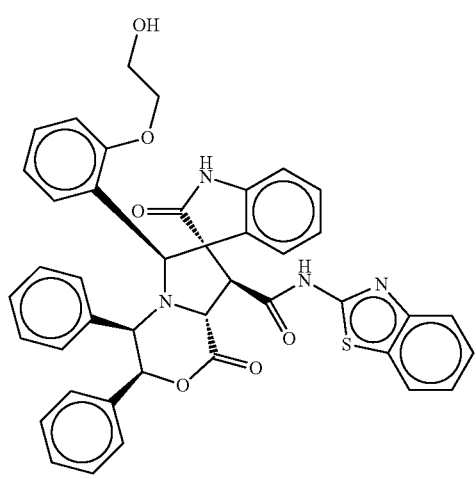
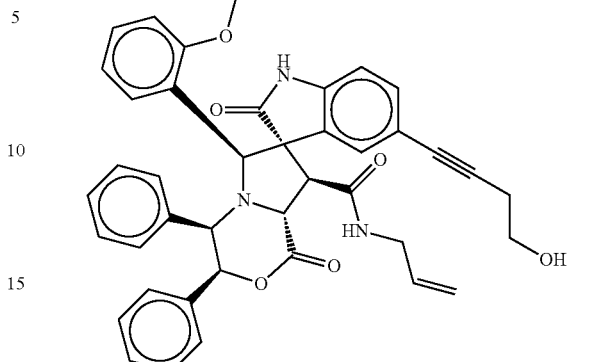
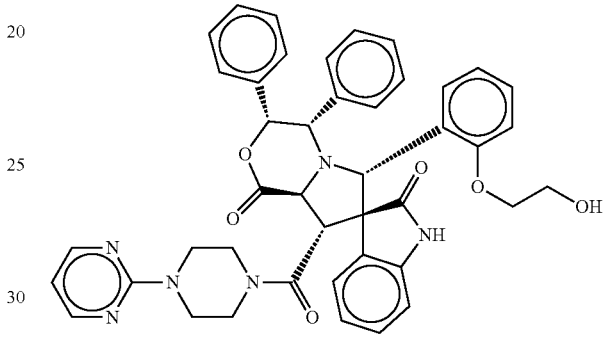
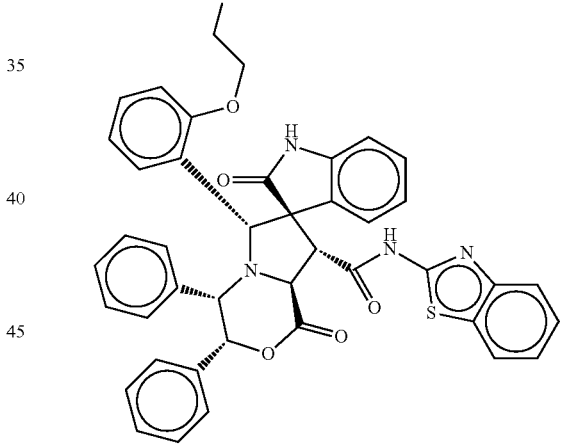
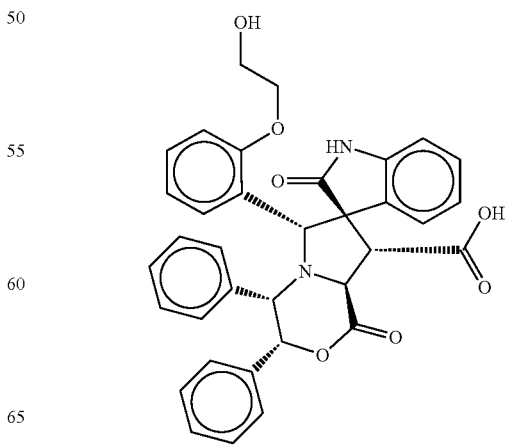

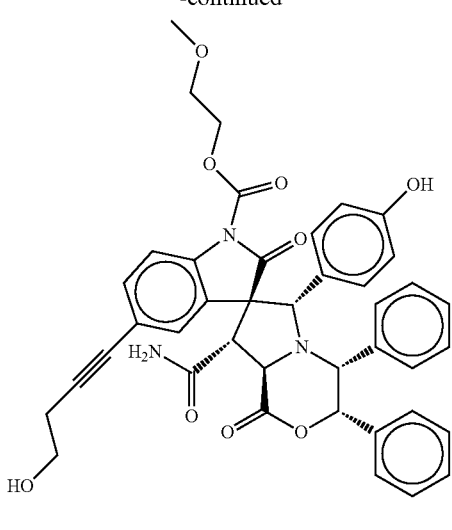

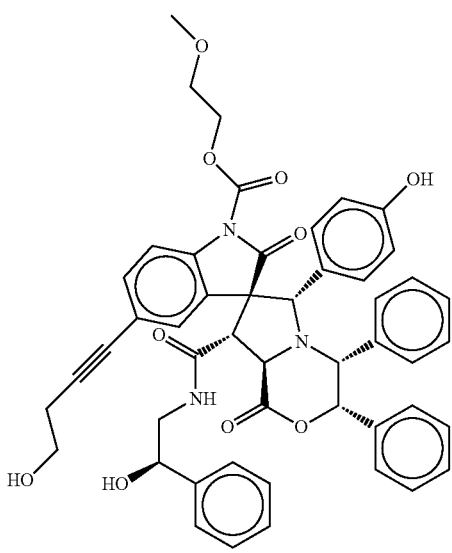

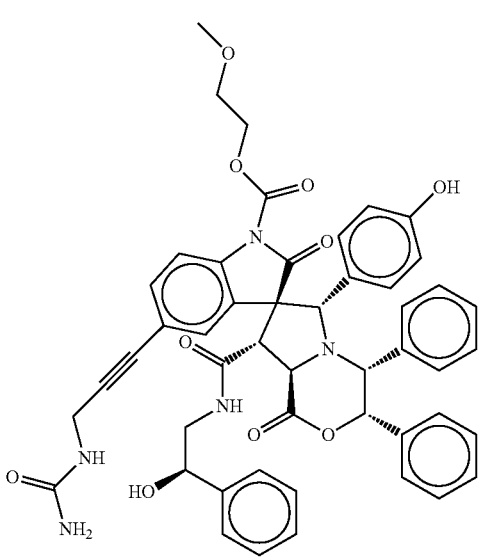

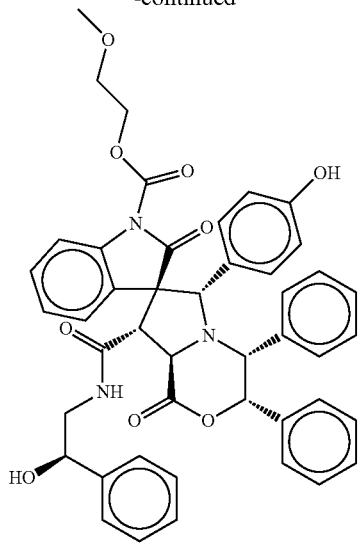

In other embodiments, the compound discovered to bind DISC1 or an isoform or variant thereof is a compound of formula:

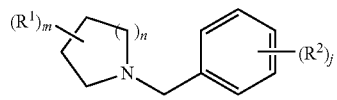

wherein
n is 1 or 2;
m is an integer between 0 and 10, inclusive;
j is an integer between 0 and 5, inclusive;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR^A$; —$C(=O)R^A$; —$CO_2R^A$; —$C(=O)N(R^A)_2$; —CN; —SCN; —$SR^A$; —$SOR^A$; —$SO_2R^A$; —$NO_2$; —$N(R^A)_2$; —$NHC(O)R^A$; or —$C(R^A)_3$; wherein each occurrence of $R^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

each occurrence of $R^2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR^B$; —$C(=O)R^B$; —$CO_2R^B$; —$C(=O)N(R^B)_2$; —CN; —SCN; —$SR^B$; —$SOR^B$; —$SO_2R^B$; —$NO_2$; —$N(R^B)_2$; —NHC(O)$R^B$; or —$C(R^B)_3$; wherein each occurrence of $R^B$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy; and pharmaceutically acceptable salts thereof. In certain embodiments, n is 1. In other embodiments, n is 2. In certain embodiments, m is at least 2. In certain embodiments, j is at least 2. In certain embodiments, the compound is of one of the formulae:

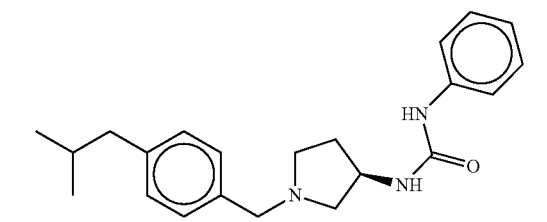

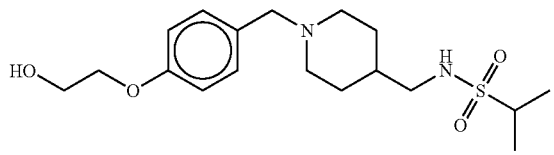

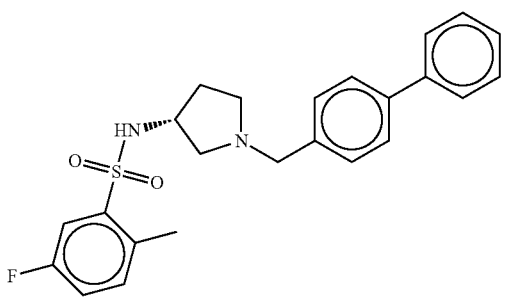

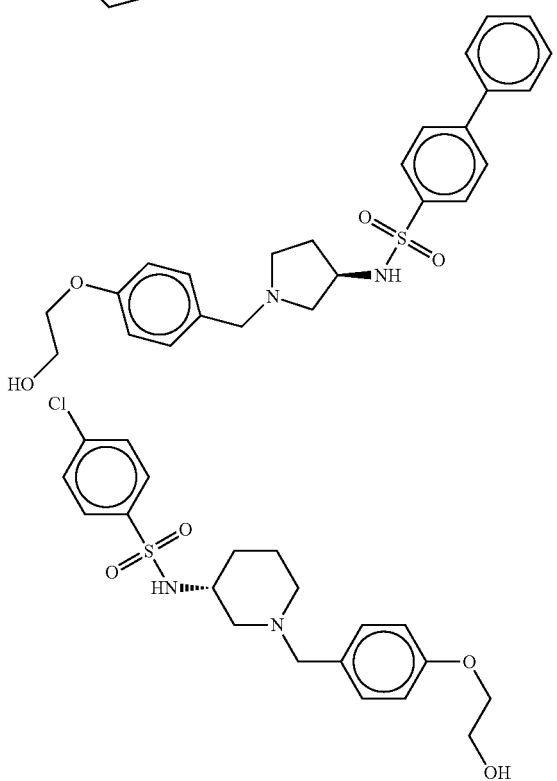

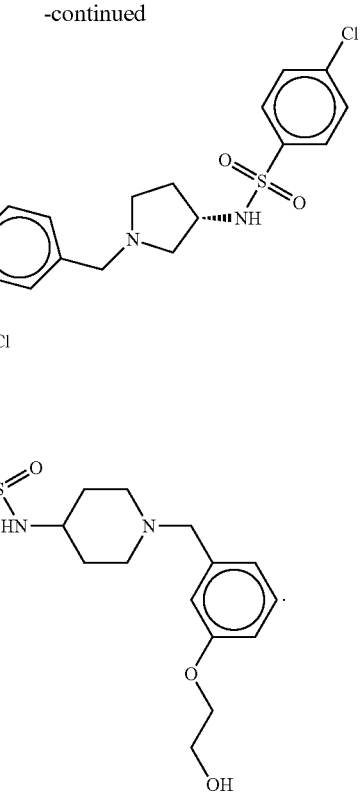

In other embodiments, the compound discovered to bind DISC1 or an isoform or variant thereof is a compound of formula:

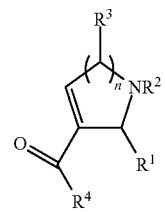

wherein n is 1 or 2;

$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR^A$; —$C(=O)R^A$; —$CO_2R^A$; —$C(=O)N(R^A)_2$; —CN; —SCN; —$SR^A$; —$SOR^A$; —$SO_2R^A$; —$NO_2$; —$N(R^A)_2$; —$NHC(O)R^A$; or —$C(R^A)_3$; wherein each occurrence of $R^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

$R^2$ is hydrogen, $C_{1-6}$ aliphatic, or a protecting group;

each occurrence of $R^3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$^C$; —C(=O)R$^C$; —CO$_2$R$^C$; —C(=O)N(R$^C$)$_2$; —CN; —SCN; —SR$^C$; —SOR$^C$; —SO$_2$R$^C$; —NO$_2$; —N(R$^C$)$_2$; —NHC(O)R$^C$; or —C(R$^C$)$_3$; wherein each occurrence of R$^C$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

R$^4$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$^D$; —C(=O)R$^D$; —CO$_2$R$^D$; —C(=O)N(R$^D$)$_2$; —CN; —SCN; —SR$^D$; —N(R$^D$)$_2$; —NHC(O)R$^D$; or —C(R$^D$)$_3$; wherein each occurrence of R$^D$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy; and pharmaceutically acceptable salts. In certain embodiments, the compound is of formula:

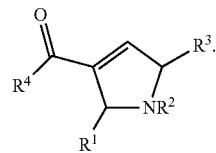

In certain embodiments, the compound is of formula:

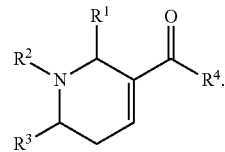

In other embodiments, the compound discovered to bind DISC1 or an isoform or variant thereof is a compound of formula:

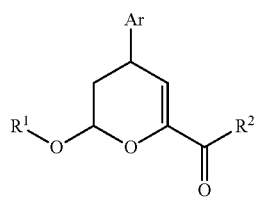

wherein
R$^1$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^A$; —CO$_2$R$^A$; —C(=O)N(R$^A$)$_2$; or —C(R$^A$)$_3$; wherein each occurrence of R$^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

R$^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$^B$; —C(=O)R$^B$; —CO$_2$R$^B$; —C(=O)N(R B)$_2$; —SRB; —N(R$^B$)$_2$; —NHC(O)R$^B$; or —C(R$^B$)$_3$; wherein each occurrence of R$^B$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

Ar is independently substituted or unsubstituted, branched or unbranched aryl; or substituted or unsubstituted, branched or unbranched heteroaryl; and pharmaceutically acceptable salts thereof. In certain embodiments, Ar is a substituted or unsubstituted aryl moiety. In certain embodiments, Ar is a substituted phenyl moiety. In certain embodiments, the compound is of one of the formulae:

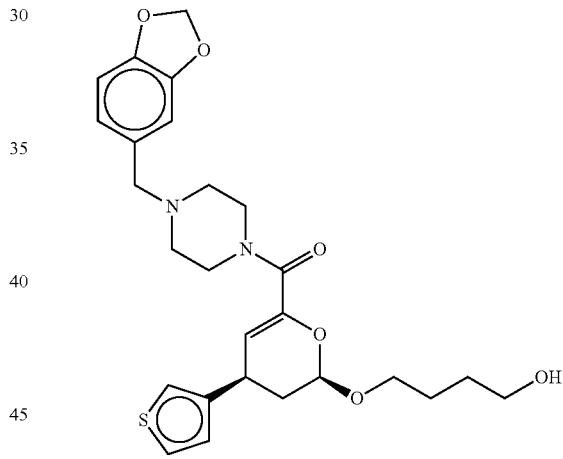

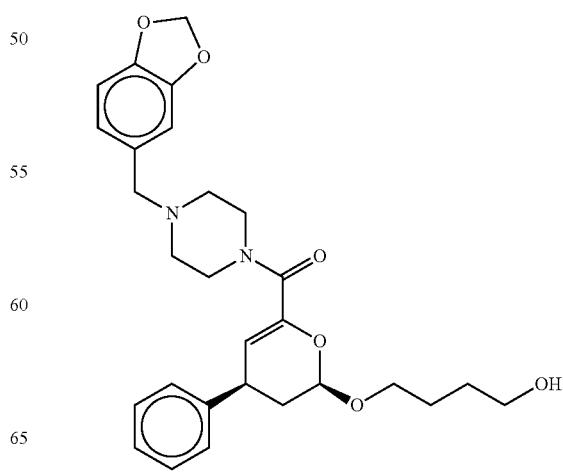

-continued

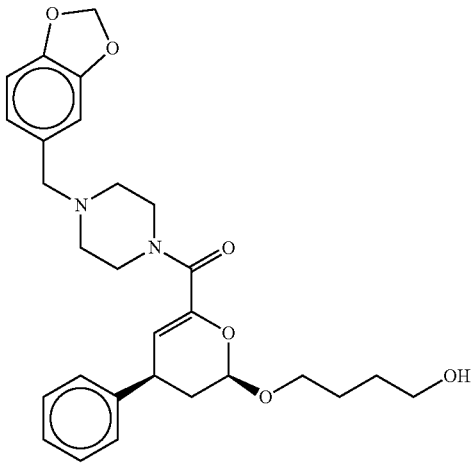

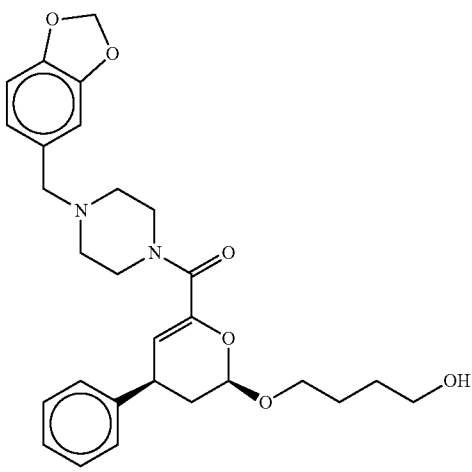

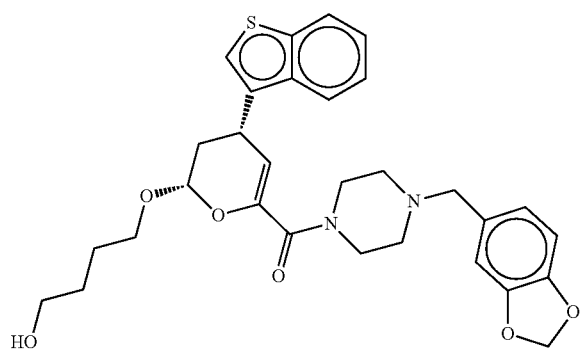

-continued

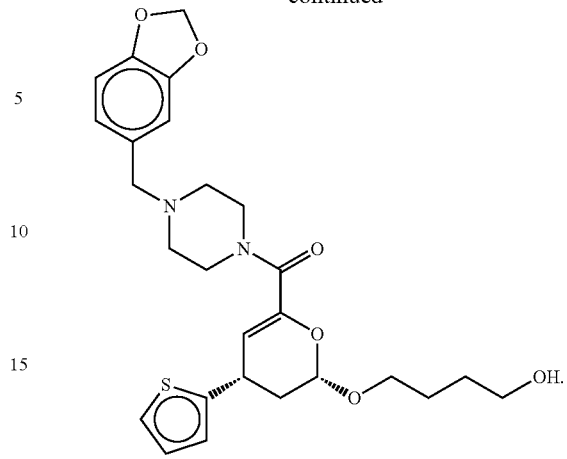

In other embodiments, the compound discovered to bind DISC1 or an isoform or variant thereof is a compound of formula:

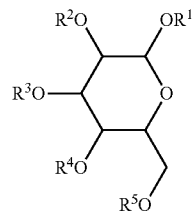

wherein $R^1$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^4$; —CO$_2$$R^4$; —C(=O)N($R^4$)$_2$; or —C($R^4$)$_3$; wherein each occurrence of $R^4$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

$R^2$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^4$; —CO$_2$$R^4$; —C(=O)N($R^4$)$_2$; or —C($R^4$)$_3$; wherein each occurrence of $R^4$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

$R^3$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^4$; —CO$_2$$R^4$; —C(=O)N($R^4$)$_2$; or —C($R^4$)$_3$; wherein each occurrence of $R^4$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

$R^4$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^4$; —CO$_2R^4$; —C(=O)N($R^4$)$_2$; or —C($R^4$)$_3$; wherein each occurrence of $R^4$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

$R^5$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^4$; —CO$_2R^4$; —C(=O)N($R^4$)$_2$; or —C($R^4$)$_3$; wherein each occurrence of $R^4$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy; and pharmaceutically acceptable salts thereof. In certain embodiments, the compound is of the formula:

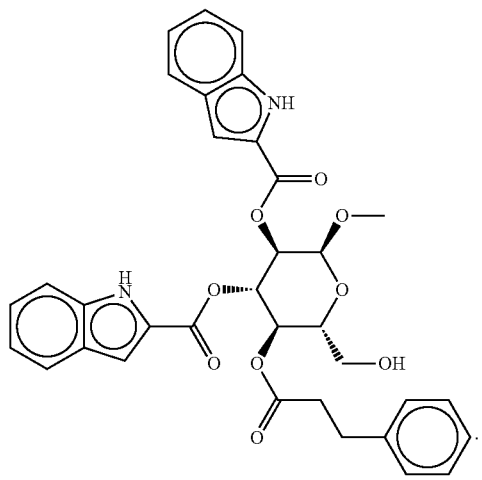

In some aspects the invention relates to compositions of the above-identified molecules with a pharmaceutically acceptable carrier. Optionally the pharmaceutically acceptable carrier may be sterile. It may be formulated for oral delivery, delivery by injection, intravenous delivery or any other known delivery route. In some embodiments the pharmaceutically acceptable carrier includes a sustained release implant.

Exogenous DISC1 nucleic acids or polypeptides are also DISC1 agonists. The DISC1 nucleic acid can be administered to a subject such that a DISC1 polypeptide is produced in vivo. The polypeptide produced from the nucleic acid or the DISC1 polypeptide that is administered directly to the subject can then interact with and inhibit the function of GSK3. Exogenous genetic material includes isolated nucleic acids or oligonucleotides, either natural or synthetic, that are introduced into the subject to express DISC1 or fragments or homologs thereof. The exogenous genetic material may be a copy of that which is naturally present in the cells, or it may not be naturally found in the cells. It typically is at least a portion of a naturally occurring gene which has been placed under operable control of a promoter in a vector construct. DISC1 nucleic acid sequences are known in the art and have been described in, for instance, US Patent Application 2003/0054345.

As used herein the term "isolated nucleic acid molecule" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a small percentage of the material in the cell in which it resides. Such a nucleic acid is isolated, however, as the term is used herein because it is readily manipulable by standard techniques known to those of ordinary skill in the art.

The DISC1 nucleic acid molecules of the invention also encompass homologs and alleles which can be identified by conventional techniques. Identification of human and other organisms' homologs of DISC1 polypeptides will be familiar to those of skill in the art. In general, nucleic acid hybridization is a suitable method for identification of homologous sequences of another species (e.g., human, cow, sheep, dog, rat, mouse), which correspond to a known sequence. Standard nucleic acid hybridization procedures can be used to identify related nucleic acid sequences of selected percent identity. For example, one can construct a library of cDNAs reverse transcribed from the mRNA of a selected tissue and use the DISC1 nucleic acid molecules identified herein to screen the library for related nucleotide sequences. The screening preferably is performed using high-stringency conditions to identify those sequences that are closely related by sequence identity. Nucleic acids so identified can be translated into polypeptides and the polypeptides can be tested for activity.

The term "high stringency" as used herein refers to parameters with which the art is familiar. Nucleic acid hybridization parameters may be found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. More specifically, high-stringency conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM NaH$_2$PO$_4$ (pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5× SSC/0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of the DISC1 nucleic acids of the invention (e.g., by using lower stringency conditions). The skilled artisan also is familiar with the methodology for screening cells and libraries for expression of such molecules, which then are routinely isolated, followed by isolation of the pertinent nucleic acid molecule and sequencing.

In general, homologs and alleles typically will share at least 90% nucleotide identity and/or amino acid identity to the sequences of DISC1 nucleic acids and polypeptides, respectively, in some instances will share at least 95% nucleotide identity and/or amino acid identity, in other instances will share at least 97% nucleotide identity and/or amino acid identity, in other instances will share at least 98% nucleotide identity and/or amino acid identity, and in other instances will share at least 99% nucleotide identity and/or amino acid identity. The homology can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using a number of sequence analysis software programs, such as the MacVector sequence analysis software (Accelrys Software Inc., San Diego, Calif.). Watson-Crick complements of the foregoing nucleic acids also are embraced by the invention.

The invention also includes degenerate nucleic acids that include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating DISC1 polypeptide. Similarly, nucleotide sequence triplets which encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions and deletions of one or more nucleotides (preferably 1-20 nucleotides). In preferred embodiments, these modified nucleic acid molecules and/or the polypeptides they encode retain at least one activity or function of the unmodified nucleic acid molecule and/or the polypeptides, such as the ability to bind to and inhibit GSK3. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules that encode polypeptides having two amino acid changes can be prepared which have, e.g., 2-6 nucleotide changes.

An expression vector comprising the isolated DISC1 nucleic acid molecules of the invention, preferably operably linked to a promoter is used to deliver the nucleic acids to the cells of a subject. As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids, and virus genomes.

A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript.

Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art, e.g., β-galactosidase or alkaline phosphatase, and genes which visibly affect the phenotype of transformed or transfected cells, hosts, colonies or plaques, e.g., green fluorescent protein. Preferred vectors are those capable of autonomous replication and expression of the structural gene products present in the DNA segments to which they are operably joined.

As used herein, a coding sequence and regulatory sequences are said to be "operably joined" when they are covalently linked in such a way as to place the expression or transcription of the coding sequence under the influence or control of the regulatory sequences. As used herein, "operably joined" and "operably linked" are used interchangeably and should be construed to have the same meaning. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region is operably joined to a coding sequence if the promoter region is capable of effecting transcription of that DNA sequence such that the resulting transcript can be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Often, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

DISC1 polypeptides (including whole proteins and partial proteins) such as those encoded by the foregoing DISC1 nucleic acids may also be delivered to a subject as a DISC1 pathway activator. DISC1 polypeptides are useful, for example, alone or as fusion proteins. DISC1 polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Fragments of the DISC1 polypeptides also can be synthesized chemically using well-established methods of peptide synthesis.

The invention embraces the use of variants of the DISC1 polypeptides described above. As used herein, a "variant" of a DISC1 polypeptide is a polypeptide which contains one or more modifications to the primary amino acid sequence of a DISC1 polypeptide. Modifications which create a DISC1 polypeptide variant can be made to a DISC1 polypeptide 1) to reduce or eliminate an activity of a DISC1 polypeptide; 2) to enhance a property of a DISC1 polypeptide, such as protein stability in an expression system or the stability of DISC1-GSK3 binding; 3) to provide a novel activity or property to a DISC1 polypeptide, such as addition of a detectable moiety; or 4) to provide equivalent or better binding to a GSK3 molecule.

Modifications to a DISC1 polypeptide are typically made to the nucleic acid which encodes the DISC1 polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the DISC1 polypeptide amino acid sequence. One of skill in the art will be familiar with methods for predicting the effect on protein conformation of a change in protein sequence, and can thus "design" a variant DISC1 polypeptide according to known methods. One example of such a method is described by Dahiyat and Mayo in Science 278:82-87, 1997, whereby proteins can be designed de novo. The method can be applied to a known protein to vary only a portion of the polypeptide sequence. By applying the computational methods of Dahiyat and Mayo, specific variants of a DISC1 polypeptide can be proposed and tested to determine whether the variant retains a desired conformation.

In general, variants include DISC1 polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a DISC1 polypeptide by eliminating proteolysis by proteases in an expression system (e.g., dibasic amino acid residues in yeast expression systems in which KEX2 protease activity is present).

Mutations of a nucleic acid which encode a DISC1 polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

The skilled artisan will also realize that conservative amino acid substitutions may be made in DISC1 polypeptides to provide functionally equivalent variants, or homologs of the foregoing polypeptides, i.e., the variants retain the functional capabilities of the DISC1 polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Exemplary functionally equivalent variants or homologs of the DISC1 polypeptides include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the DISC1 polypeptides disclosed herein and retain the specific antibody-binding characteristics of the antigens. In some embodiments the DISC1 agonists are used for treating neurodegenerative diseases other than schizophrenia, schizoaffective disorder, bipolar disorder, and autism spectrum disorders.

DISC1 pathway activators also include GSK3 inhibitors. GSK3 inhibitors are known in the art and include SB-216763 and AR-A014418 (Sigma Aldric, St. Louis, Mo.), CT 99021 and CT20026 (Wagman et al., Discovery and developement of GSK4 inhibitors for the treatement of type 2 diabetes. Curr Pharm Des 10, 1105-37 (2004)).

DISC1 pathway activators also include GSK3 expression inhibitors. A GSK3 expression inhibitor as used herein is molecule that knocks down expression of GSK3. Thus, the invention also features the use of small nucleic acid molecules, including antisense nucleic acids and short interfering nucleic acid (siNA), the latter include, for example: microRNA (miRNA), short interfering RNA (siRNA), double-stranded RNA (dsRNA), and short hairpin RNA (shRNA) molecules to knockdown expression of proteins such as GSK3. An siNA of the invention can be unmodified or chemically-modified. An siNA of the instant invention can be chemically synthesized, expressed from a vector or enzymatically synthesized. The instant invention also features various chemically-modified synthetic short interfering nucleic acid (siNA) molecules capable of modulating gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity. The siNA molecules of the instant invention provide useful reagents and methods for a variety of therapeutic applications. In some embodiments the GSK3 expression inhibitors are used for treating neurodegenerative diseases other than Alzheimer's disease, bipolar disorder, manic depression, Huntington's, Parkinson's, AIDS associated dementia, amyotrophic lateral sclerosis (AML) and multiple sclerosis.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al, 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. (All these publications are hereby incorporated by reference herein).

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'amino, 2'-C-allyl, 2'-fluoro, 2'-O-methyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565 568; Pieken et al. Science, 1991, 253, 314317; Usman and Cedergren, Trends in Biochem. Sci., 1992, 17, 334 339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., molecule comprises one or more chemical modifications.

In one embodiment, one of the strands of the double-stranded siNA molecule comprises a nucleotide sequence that is complementary to a nucleotide sequence of a target RNA or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In another embodiment, each strand of the siNA molecule comprises about 19 to about 23 nucleotides, and each strand comprises at least about 19 nucleotides that are complementary to the nucleotides of the other strand.

In some embodiments an siNA is an shRNA, shRNA-mir, or microRNA molecule encoded by and expressed from a genomically integrated transgene or a plasmid-based expression vector. Thus, in some embodiments a molecule capable of inhibiting mRNA expression, or microRNA activity, is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems.

In another embodiment, a small interfering nucleic acid of the invention is expressed in mammalian cells using a mammalian expression vector. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the myosin heavy chain promoter, albumin promoter, lymphoid-specific promoters, neuron specific promoters, pancreas specific promoters, and mammary gland specific promoters. Developmentally-regulated promoters are also encompassed, for example the murine hox promoters and the a-fetoprotein promoter.

Other inhibitor molecules that can be used include sense and antisense nucleic acids (single or double stranded), ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10):2024-8, 1995; Quattrone et al., Cancer Res. 55(1):90-5, 1995; Lewin et al., Nat. Med. 4(8):967-71, 1998). For example, neoplastic reversion was obtained using a ribozyme targeted to an H-Ras mutation in bladder carcinoma cells (Feng et al., Cancer Res. 55(10):2024-8, 1995). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6):643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9,1996). Multitarget ribozymes (connected or shotgun) have been suggested as a means of improving efficiency of ribozymes for gene suppression (Ohkawa et al., Nucleic Acids Symp Ser. (29):121-2, 1993).

Antisense nucleic acids include modified or unmodified RNA, DNA, or mixed polymer nucleic acids, and primarily function by specifically binding to matching sequences resulting in modulation of peptide synthesis (Wu-Pong, November 1994, BioPharm, 20-33). Antisense nucleic acid binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996, Crit. Rev. in Oncogenesis 7, 151-190).

As used herein, the term "antisense nucleic acid" describes a nucleic acid that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence.

Triple helix approaches have also been investigated for sequence-specific gene suppression. Triple helix forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Hanvey et al., Antisense Res. Dev. 1(4):307-17, 1991; Knudsen and Nielson Nucleic Acids Res. 24(3):494-500, 1996; Taylor et al., Arch. Surg. 132(11):1177-83, 1997). Minor-groove binding polyamides can bind in a sequence-specific manner to DNA targets and hence may represent useful small molecules for future suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). In some cases suppression strategies have led to a reduction in RNA levels without a concomitant reduction in proteins, whereas in others, reductions in RNA have been mirrored by reductions in protein.

The diverse array of suppression strategies that can be employed includes the use of DNA and/or RNA aptamers that can be selected to target, for example, a protein of interest such as GSK3.

An agent that promotes DISC1-GSK3 binding is a compound that results in enhanced DISC1-GSK3 binding interaction. The enhanced binding interaction may occur through stabilization of the DISC1-GSK3 interaction by for instance a third compound, such as a peptide or an antibody that binds to DISC1 or GSK3 or both and promotes a conformation consistent with the interaction. Antibodies that bind to DISC1 and GSK3 are known in the art. A number of commercially available antibodies are available including those sold by Abbiotec; Abcam; ABR-Affinity Bioreagents, now sold as Thermo Scientific; Aviva Systems Biology; Everest Biotech; GeneTex; GenWay Biotech, Inc.; IMGENEX; LifeSpan Biosciences; Novus Biologicals; Raybiotech, Inc.; and Santa Cruz Biotechnology, Inc. The skilled artisan could use such commercially available antibodies to develop humanized antibodies or ScFvs, if desirable. The term "antibody" herein is used in the broadest sense and specifically covers intact monoclonal antibodies, polyclonal antibodies, multispecific antibodies (e.g. bispecific antibodies) formed from at least two intact antibodies, antibody fragments, so long as they exhibit the desired biological activity, and antibody like molecules such as scFv.

In some embodiments the DISC1 pathway activator is one that has not previously been indicated for the treatment of a neurological disorder. A "DISC1 pathway activator is one that has not previously been indicated for the treatment of a neurological disorder" as used herein refers to a compound that had not, prior to the invention, been proposed for the treatment of the disease for which it is now, based on the discoveries of the invention, being used. For instance, a drug which had previously been proposed for the treatment of bipolar disorder would not fall within the scope of this particular embodiment even if it is a DISC1 pathway activator. For instance, lithium is an AKT and GSK3 inhibitor but it is not a DISC1 pathway activator of the invention.

Since it has now been shown according to the invention that multiple domains of DISC1 interact with and inhibit GSK3β, it is expected that mutations in multiple regions can affect this interaction. Thus, DISC1 mutations in different domains affect the interaction with a particular binding partner, increasing the risk for the manifestation of mental disorders. However, the subject may or may not have been previously diagnosed as having a DISC1 mutation. The methods can be performed regardless of such a diagnosis. Regardless of the diagnosis, the subject may or may not have a DISC1 mutation. Thus, the methods of the invention are also useful in the instance that the subject does not have a DISC1 mutation.

As used herein, a "subject" is preferably a human, non-human primate, cow, horse, pig, sheep, goat, dog, cat or rodent. In all embodiments, human subjects are preferred. In some embodiments, the subject is suspected of having a neurodegenerative disease or has been diagnosed with neurodegenerative disease. In other embodiments, the subject is suspected of having a GSK3 disorder or has been diagnosed with GSK3 disorder.

As used herein, the term "treating" and "treatment" refers to modulating certain areas of the brain so that the subject has an improvement in the disease, for example, beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

The term "neurological disorder" as used in this invention includes neurological diseases, neurodegenerative diseases and neuropsychiatric disorders. A neurological disorder is a condition having as a component a central or peripheral nervous system malfunction. Neurological disorders may cause a disturbance in the structure or function of the nervous system resulting from developmental abnormalities, disease, genetic defects, injury or toxin. These disorders may affect the central nervous system (e.g., the brain, brainstem and cerebellum), the peripheral nervous system (e.g., the cranial nerves, spinal nerves, and sympathetic and parasympathetic nervous systems) and/or the autonomic nervous system (e.g., the part of the nervous system that regulates involuntary action and that is divided into the sympathetic and parasympathetic nervous systems).

As used herein the term "neurodegenerative disease" implies any disorder that might be reversed, deterred, managed, treated, improved, or eliminated with agents that stimulate the generation of new neurons. Examples of neurodegenerative disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapic, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor). and Wernicke-Korsakoff's related dementia. Neurodegenerative diseases affecting sensory neurons include Friedreich's ataxia, diabetes, peripheral neuropathy, and retinal neuronal degeneration. Other neurodegenerative diseases include nerve injury or trauma associated with spinal cord injury. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder."

Parkinson's disease is a disturbance of voluntary movement in which muscles become stiff and sluggish. Symptoms of the disease include difficult and uncontrollable rhythmic twitching of groups of muscles that produces shaking or tremors. Currently, the disease is caused by degeneration of pre-synaptic dopaminergic neurons in the brain and specifically in the brain stem. As a result of the degeneration, an inadequate release of the chemical transmitter dopamine occurs during neuronal activity.

Amyotrophic lateral sclerosis (ALS), also called Lou Gehrig's disease, is a progressive, fatal neurological disease. ALS occurs when specific nerve cells in the brain and spinal cord that control voluntary movement gradually degenerate and causes the muscles under their control to weaken and waste away, leading to paralysis. Currently there is no cure for ALS; nor is there a proven therapy that will prevent or reverse the course of the disorder.

Currently, Parkinson's disease is treated with several different compounds and combinations. Levodopa (L-dopa), which is converted into dopamine in the brain, is often given to restore muscle control. Perindopril, an ACE inhibitor that crosses the blood-brain barrier, is used to improve patients' motor responses to L-dopa. Carbidopa is administered with L-dopa in order to delay the conversion of L-dopa to dopamine until it reaches the brain, and it also lessens the side effects of L-dopa. Other drugs used in Parkinson's disease treatment include dopamine mimicers Mirapex (pramipexole dihydrochloride) and Requip (ropinirole hydrochloride), and Tasmar (tolcapone), a COMT inhibitor that blocks a key enzyme responsible for breaking down levodopa before it reaches the brain.

Autism (also referred to as Autism Spectrum Disorder, or ASD) is a disorder that seriously impairs the functioning of individuals. It is characterized by self-absorption, a reduced ability to communicate with or respond to the outside world, rituals and compulsive phenomena, and mental retardation. Autistic individuals are also at increased risk of developing seizure disorders, such as epilepsy. While the actual cause of autism is unknown, it appears to include one or more genetic factors, as indicated by the fact that the concordance rate is higher in monozygotic twins than in dizygotic twins, and may also involve immune and environmental factors, such as diet, toxic chemicals and infections.

In some instances the neurological disorder is a neuropsychiatric disorder, which refers to conditions or disorders that relate to the functioning of the brain and the cognitive processes or behavior. Neuropsychiatric disorders may be further classified based on the type of neurological disturbance affecting the mental faculties. The term "neuropsychiatric disorder," considered here as a subset of "neurological disorders," refers to a disorder which may be generally characterized by one or more breakdowns in the adaptation process. Such disorders are therefore expressed primarily in abnormalities of thought, feeling and/or behavior producing either distress or impairment of function (i.e., impairment of mental function such with dementia or senility). Currently, individuals may be evaluated for various neuropsychiatric disorders using criteria set forth in the most recent version of the American Psychiatric Association's Diagnostic and Statistical Manual of Mental Health (DSM-IV).

One group of neuropsychiatric disorders includes disorders of thinking and cognition, such as schizophrenia and delirium. A second group of neuropsychiatric disorders includes disorders of mood, such as affective disorders and anxiety. A third group of neuropsychiatric disorders includes disorders of social behavior, such as character defects and personality disorders. And a fourth group of neuropsychiatric disorders includes disorders of learning, memory, and intelligence, such as mental retardation and dementia. Accordingly, neuropsychiatric disorders encompass schizophrenia, delirium, attention deficit disorder (ADD), schizoaffective disorder Alzheimer's disease, depression, mania, attention deficit disorders, drug addiction, dementia, agitation, apathy, anxiety, psychoses, personality disorders, bipolar disorders, unipolar affective disorder, obsessive-compulsive disorders, eating disorders, post-traumatic stress disorders, irritability, adolescent conduct disorder and disinhibition.

Schizophrenia is a disorder that affects about one percent of the world population. Three general symptoms of schizophrenia are often referred to as positive symptoms, negative symptoms, and disorganized symptoms. Positive symptoms can include delusions (abnormal beliefs), hallucinations (abnormal perceptions), and disorganized thinking. The hallucinations of schizophrenia can be auditory, visual, olfactory, or tactile. Disorganized thinking can manifest itself in schizophrenic patients by disjointed speech and the inability to maintain logical thought processes. Negative symptoms can represent the absence of normal behavior. Negative symptoms include emotional flatness or lack of expression and can be characterized by social withdrawal, reduced energy, reduced motivation, and reduced activity. Catatonia can also be associated with negative symptoms of schizophrenia. The symptoms of schizophrenia should continuously persist for a duration of about six months in order for the patient to be diagnosed as schizophrenic. Based on the types of symptoms a patient reveals, schizophrenia can be categorized into subtypes including catatonic schizophrenia, paranoid schizophrenia, and disorganized schizophrenia.

Examples of antipsychotic drugs that may be used to treat schizophrenic patients include phenothizines, such as chlorpromazine and trifluopromazine; thioxanthenes, such as chlorprothixene; fluphenazine; butyropenones, such as haloperidol; loxapine; mesoridazine; molindone; quetiapine; thiothixene; trifluoperazine; perphenazine; thioridazine; risperidone; dibenzodiazepines, such as clozapine; and olanzapine. Although these agents may relieve the symptoms of schizophrenia, their administration can result in undesirable side effects including Parkinson's disease-like symptoms (tremor, muscle rigidity, loss of facial expression); dystonia; restlessness; tardive dyskinesia; weight gain; skin problems; dry mouth; constipation; blurred vision; drowsiness; slurred speech and agranulocytosis.

Mania is a sustained form of euphoria that affects millions of people in the United States who suffer from depression. Manic episodes can be characterized by an elevated, expansive, or irritable mood lasting several days, and is often accompanied by other symptoms, such as, over-activity, over-talkativeness, social intrusiveness, increased energy, pressure of ideas, grandiosity, distractibility, decreased need for sleep, and recklessness. Manic patients can also experience delusions and hallucinations.

Depressive disorders can involve serotonergic and noradrenergic neuronal systems based on current therapeutic regimes that target serotonin and noradrenalin receptors. Mania may results from an imbalance in certain chemical messengers within the brain. Administering phosphotidyl choline has been reported to alleviate the symptoms of mania.

Anxiety disorders are characterized by frequent occurrence of symptoms of fear including arousal, restlessness, heightened responsiveness, sweating, racing heart, increased blood pressure, dry mouth, a desire to run or escape, and avoidance behavior. Generalized anxiety persists for several months, and is associated with motor tension (trembling, twitching, muscle aches, restlessness); autonomic hyperactivity (shortness of breath, palpitations, increased heart rate, sweating, cold hands), and vigilance and scanning (feeling on edge, exaggerated startle response, difficult in concentrating). Benzodiazepines, which enhance the inhibitory effects of the gamma aminobutyric acid (GABA) type A receptor, are frequently used to treat anxiety. Buspirone is another effective anxiety treatment.

Alzheimer's disease is a degenerative brain disorder characterized by cognitive and noncognitive neuropsychiatric symptoms. Psychiatric symptoms are common in Alzheimer's disease, with psychosis (hallucinations and delusions) present in approximately fifty percent of affected patients. Similar to schizophrenia, positive psychotic symptoms are common in Alzheimer's disease. Delusions typically occur more frequently than hallucinations. Alzheimer's patients may also exhibit negative symptoms, such as disengagement, apathy, diminished emotional responsiveness, loss of volition, and decreased initiative. Indeed, antipsychotic agents that are used to relieve psychosis of schizophrenia are also useful in alleviating psychosis in Alzheimer's patients. As used herein, the term "dementia" refers to the loss, of cognitive and intellectual functions without impairment of perception or consciousness. Dementia is typically characterized by disorientation, impaired memory, judgment, and intellect, and a shallow labile affect.

Schizo-affective disorder describes a condition where both the symptoms of a mood disorder and schizophrenia are present. A person may manifest impairments in the perception or expression of reality, most commonly in the form of auditory hallucinations, paranoid or bizarre delusions or disorganized speech and thinking, as well as discrete manic and/or depressive episodes in the context of significant social or occupational dysfunction.

Mood disorders are typically characterized by pervasive, prolonged, and disabling exaggerations of mood and affect that are associated with behavioral, physiologic, cognitive, neurochemical and psychomotor dysfunctions. The major mood disorders include, but are not limited to major depressive disorder (also known as unipolar disorder), bipolar disorder (also known as manic depressive illness or bipolar depression), dysthymic disorder.

The term "depression" refers to a morbid sadness, dejection, or melancholy.

The methods of the invention also include methods of enhancing neural progenitor proliferation and differentiation using DISC1 pathway activators. As used herein, the term "neural" refers to a neuron which is a morphologic and functional unit of the brain, spinal column, and peripheral nerves. Neural progenitor cells, also called neuronal precursor cells, are cells found in the central nervous system. They are able to differentiate into neurons, astrocytes and oligodendrocytes.

The terms "progenitor cell" and "stem cell" are often used interchangeably herein. Stem cells or progenitor cells that can be stimulated in vivo to proliferate, migrate and/or differentiate include adult stem cells and precursor cells. Such stem cells and precursor cells include, for example, cells of hematopoietic tissue, neuronal tissue, perivascular tissue and endothelial cells.

Neurogenesis is a vital process in the brains of animals and humans, whereby new nerve cells are continuously generated throughout the life span of the organism. The newly born cells are able to differentiate into functional cells of the central nervous system and integrate into existing neural circuits in the brain. Neurogenesis is known to persist throughout adulthood in two regions of the mammalian brain: the subventricular zone (SVZ) of the lateral ventricles and the dentate gyrus of the hippocampus. In these regions, multipotent neural progenitor cells (NPCs) continue to divide and give rise to new functional neurons and glial cells. "Neurogenesis" is defined herein as proliferation, differentiation, migration and/or survival of a neural cell in vivo or in vitro. In some embodiments, the neural cell is an adult, fetal, or embryonic neural stem cell or population of cells. The cells may be located in the central nervous system or elsewhere in an animal or human being. The cells may also be in a tissue, such as neural tissue. In some embodiments, the neural cell is an adult, fetal, or embryonic progenitor cell or population of cells, or a population of cells comprising a mixture of stem cells and progenitor cells. Neural cells include all brain stem cells, all brain progenitor cells, and all brain precursor cells. Except where otherwise required, the invention can be practiced using stem cells of any vertebrate species. Included are stem cells from humans; as well as non-human primates, domestic animals, livestock, and other non-human mammals.

Stem cells are characterized by the ability to renew themselves through numerous cycles of cell division and the capacity to differentiate into specialized cell types in response to specific cell signals. Due to these characteristics, the stem cells can be used to restore otherwise unregeneratable nerve cells and treat intractable CNS diseases.

The activators of the invention are useful in differentiating neural stem cells. In this context a "differentiated cell" is a cell that has progressed further down the developmental pathway than the cell it is being compared with. Thus, pluripotent embryonic stem cells can differentiate to lineage-restricted precursor cells, such as hematopoetic cells, which are pluripotent for blood cell types; hepatocyte progenitors, which are pluripotent for hepatocytes; and various types of neural progenitors listed above. These in turn can be differentiated further to other types of precursor cells further down the pathway, or to an end-stage differentiated cell, which plays a characteristic role in a certain tissue type, and may or may not retain the capacity to proliferate further. Neurons, astrocytes, and oligodendrocytes are all examples of terminally differentiated cells.

The neural stem cells may be cultured in the presence of the activator of the invention in order to induce proliferation and differentiation. Typically, the differentiation takes place in a culture environment comprising a suitable substrate, and a nutrient medium to which the differentiation agents are added. Suitable substrates include solid surfaces coated with a positive charge, such as a basic amino acid, exemplified by poly-L-lysine and polyomithine. Substrates can be coated with extracellular matrix components, exemplified by fibronectin. Other permissive extracellular matrixes include Matrigel® (extracellular matrix from Engelbreth-Holm-Swarm tumor cells) and laminin. Also suitable are combination substrates, such as poly-L-lysine combined with fibronectin, laminin, or both. Conditions for such culture vary but optionally may include culture at 37° C. in an atmosphere of 5% $CO^2$ for 4 to 14 days while conducting medium replacement of total amount or partial amount every few days. Any medium as long as it does not prevent the promotion of neuropoiesis may be used in the culture of the neural stem cells? In some embodiments a DMEM/F12 medium (Invitrogen. Corporation) containing a 1% N2 supplement or the like is used. An example of a concentration suitable for promoting neurogenesis is 100 nmol/l to 100 mmol/l per neural stem cell densities of approximately $1.8 \times 10^5$ cells/cm2. A more limited concentration range of the activator is 100 µmol/l to 10 mmol/l.

The invention also includes isolated neurons, astrocytes, and oligodendrocytes, obtained by using the neurogenesis methods of the invention. In some embodiments it is a cell population that proliferates in an in vitro culture, obtained by differentiating neural stem cells, wherein at least about 30% of the cells in the population are committed to form neuronal cells, glial cells, or both. The characterization of various types of nerve cells, markers, and related soluble factors, are described for instance, in CNS Regeneration: Basic Science and Clinical Advances, M. H. Tuszynski & J. H. Kordower, eds., Academic Press, 1999.

Cells can be characterized according to a number of phenotypic criteria. The criteria include but are not limited to microscopic observation of morphological features, detection or quantitation of expressed cell markers, enzymatic activity, or neurotransmitters and their receptors, and electrophysiological function. The cells may have morphological features characteristic of neuronal cells or glial cells. The features are readily appreciated by those skilled in evaluating the presence of such cells. For example, characteristic of neurons are small cell bodies, and multiple processes reminiscent of axons and dendrites. The cells may also express phenotypic markers characteristic of neural cells of various kinds.

Markers of interest include but are not limited to .beta.-tubulin III, microtubule-associated protein 2 (MAP-2), or neurofilament, characteristic of neurons; glial fibrillary acidic protein (GFAP), present in astrocytes; galactocerebroside (GalC) or myelin basic protein (MBP), characteristic of oligodendrocytes; Oct-4, characteristic of undifferentiated hES cells; Nestin, characteristic of neural precursors and other cells. Tissue-specific markers can be detected using any suitable immunological technique, such as, for example, flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods.

Also characteristic of neural cells, particularly terminally differentiated cells, are receptors and enzymes involved in the biosynthesis, release, and reuptake of neurotransmitters, and ion channels involved in the depolarization and repolarization events that relate to synaptic transmission. Evidence of synapse formation can be obtained by staining for synaptophysin. Evidence for receptivity to certain neurotransmitters can be obtained by detecting receptors for γ-amino butyric acid (GABA), glutamate, dopamine, 3,4-dihydroxyphenylalanine (DOPA), noradrenaline, acetylcholine, and serotonin.

The methods described herein can be used to produce large numbers of neural precursor cells and mature neuronal and glial cells, which can be used for a number of research, development, and commercial purposes. For instance, the cells of this invention can be used to prepare a cDNA library relatively uncontaminated with cDNA preferentially expressed in cells from other lineages. The differentiated cells can also be used to prepare antibodies that are specific for markers of multipotent neural progenitors, cells committed to the neuronal or glial cell lineage, and mature neurons, astrocytes, and oligodendrocytes.

The neural cells generated according to the invention can also be used therapeutically to restore central nervous system (CNS) function to a subject needing such therapy, perhaps due to an inborn error in function, the effect of a disease condition, or the result of an injury. To determine the suitability of neural precursor cells for therapeutic administration, the cells can first be tested in a suitable animal model. Various animal models for testing restoration of nervous system function are described in "CNS Regeneration: Basic Science and Clinical Advances", M. H. Tuszynski & J. H. Kordower, eds., Academic Press, 1999. The cells may be assessed in the animal models for their ability to survive and maintain their phenotype in vivo. The cells can be assessed by including a detectable label (such as green fluorescent protein, or .beta.-galactosidase) or by subsequent detection of a constitutive cell marker (for example, using human-specific antibody).

Differentiated cells of this invention can also be used for tissue reconstitution or regeneration in a human patient in need thereof. The cells are administered in a manner that permits them to graft or migrate to the intended tissue site and reconstitute or regenerate the functionally deficient area. Alternatively the activators of the invention can be used to increase an intracerebral neuron by promoting neuropoiesis through directly acting on an intracerebral neural stem cell of a human or an animal. The cells can be used to treat acute or chronic damage to the nervous system. For example, excitotoxicity has been implicated in a variety of conditions including epilepsy, stroke, ischemia, Huntington's disease, Parkinson's disease and Alzheimers disease. The cells may also be appropriate for treating dysmyelinating disorders, such as Pelizaeus-Merzbacher disease, multiple sclerosis, leukodystrophies, neuritis and neuropathies. Appropriate for these purposes are cell cultures enriched in oligodendrocytes or oligodendrocyte precursors to promote remyelination. For example the treated cells may be transplanted directly into parenchymal or intrathecal sites of the central nervous system, according to the disease being treated. Grafts are done using single cell suspension or small aggregates at a density of 25,000-500,000 cells per PL (U.S. Pat. No. 5,968,829).

The neural progenitor cells (to be treated with activators of the invention) and terminally differentiated cells (already treated) can be supplied in the form of a pharmaceutical composition comprising an isotonic excipient prepared under sufficiently sterile conditions for human administration. See Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

A method of treating a GSK3 disorder is also included in the invention. The method involves the administration of a DISC1 pathway activator to a subject wherein the DISC1 pathway activator has not previously been indicated for the treatment of the GSK3 disorder. A "DISC1 pathway activator is one that has not previously been indicated for the treatment of a GSK3 disorder" as used herein refers to a compound that had not, prior to the invention, been proposed for the treatment of the disease for which it is now, based on the discoveries of the invention, being used. For instance, a drug which had previously been proposed for the treatment of diabetes would not fall within the scope of this particular embodiment even if it is a DISC1 pathway activator.

A GSK3 disorder is a disorder in which GSK3 contributes to physiological process resulting in one or more conditions contributing to a disease. Inhibition of GSK3 activity in a GSK3 disorder interrupts the physiological process and helps to improve one or more conditions or symptoms of the disease. GSK3 disorders include but are not limited to diabetes, prostate cancer, autoimmune disease, inflammatory disease, metaboic disorder, angiongenic disorder, glaucoma, baldness, and cardiovascular disease.

Diabetes is a chronic metabolic disorder which includes a severe form of childhood diabetes (also called juvenile, Type I or insulin-dependent diabetes). Type II Diabetes (DM II) is generally found in adults. Patients with diabetes of all types have considerable morbidity and mortality from microvascular (retinopathy, neuropathy, nephropathy) and macrovascular (heart attacks, stroke, peripheral vascular disease) pathology. Non-insulin dependent diabetes mellitus develops especially in subjects with insulin resistance and a cluster of cardiovascular risk factors such as obesity, hypertension and dyslipidemia, a syndrome which first recently has been recognized and is named "The metabolic syndrome".

Antidiabetic agents, include insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1 B (PTP-1 B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as LAF237;b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (framesoid X receptor) and LXR (liver X receptor) ligands; cholestyramine; fibrates; nicotinic acid and aspirin;c) anti-obesity agents such as orlistat; and) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; .beta.-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

Prostate cancer is one of the most common tumors diagnosed among men. Despite advances in screening and early detection, approximately 30% of patients undergoing definitive prostatectomy or ablative radiation therapy will have recurrent disease at 10 years. The term "prostate cancer" as used herein includes both hormone responsive, as well as hormone refractory prostate cancer, as well as benign prostate hypertrophic conditions.

Inflammatory diseases are triggered by cellular or non-cellular mediators of the immune system or tissues causing the inflammation of body tissues and subsequently producing an acute or chronic inflammatory condition. Inflammatory diseases include but are not limited to hypersensitivity reactions of type I-IV, for example hypersensitivity diseases of the lung including asthma, atopic diseases, allergic rhinitis or conjunctivitis, and angioedema.

"Autoimmune Disease" refers to those diseases which are commonly associated with the nonanaphylactic hypersensitivity reactions (Type II, Type III and/or Type IV hypersensitivity reactions) that generally result as a consequence of the subject's own humoral and/or cell-mediated immune response to one or more immunogenic substances of endogenous and/or exogenous origin. Such autoimmune diseases are distinguished from diseases associated with the anaphylactic (Type I or IgE-mediated) hypersensitivity reactions. Autoimmune diseases include Hashimoto's thyroiditis, systemic lupus erythematosus, Goodpasture's syndrome, pemphigus, myasthenia gravis, Grave's and Raynaud's disease, type B insulin-resistant diabetes, rheumatoid arthritis, psoriasis, Crohn's disease, scleroderma, mixed connective tissue disease, polymyositis, sarcoidosis, glomerulonephritis, acute or chronic host versus graft reactions.

Metabolic diseases are conditions which result from an abnormality in any of the chemical or biochemical transformations and their regulating systems essential to producing energy, to regenerating cellular constituents, to eliminating unneeded products arising from these processes, and to regulate and maintain homeostasis in a mammal regardless of whether acquired or the result of a genetic transformation. These diseases often are caused by single defects in particular biochemical pathways, defects that are due to the deficient activity of individual enzymes or molecular receptors leading to the regulation of such enzymes. They include, but are not limited to, hyperaminoacidemia, hyperaminoaciduria, disturbances of the metabolism of urea, hyperammonemia, mucopolysaccharidoses e.g. Maroteaux-Lamy syndrome, storage diseases like glycogen storage diseases and lipid storage diseases, glycogenosis diseases like Cori's disease, malabsorption diseases like intestinal carbohydrate malabsorption, oligosaccharidase deficiency like maltase-, lactase-, sucrase-insufficiency, disorders of the metabolism of fructose, disorders of the metabolism of galactose, galactosaemia, disturbances of carbohydrate utilization like diabetes, hypoglycemia, disturbances of pyruvate metabolism, hypolipidemia, hypolipoproteinemia, hyperlipidemia, hyperlipoproteinemia, carnitine or camitine acyltransferase deficiency, disturbances of the porphyrin metabolism, porphyrias, disturbances of the purine metabolism, lysosomal diseases, metabolic diseases of nerves and nervous systems like gangliosidoses, sphingolipidoses, sulfatidoses, leucodystrophies, Lesch-Nyhan syndrome.

Cardiovascular disorders include but are not limited to disorders of the heart and the vascular system like congestive heart failure, myocardial infarction, ischemic diseases of the heart, all kinds of atrial and ventricular arrhythmias, hypertensive vascular diseases, peripheral vascular diseases, and atherosclerosis. Heart failure is a pathophysiological state in which an abnormality of cardiac function is responsible for the failure of the heart to pump blood at a rate commensurate with the requirement of the metabolizing tissue. It includes all forms of pumping failures such as high-output and low-output, acute and chronic, right-sided or left-sided, systolic or diastolic, independent of the underlying cause. Myocardial infarction (MI) is generally caused by an abrupt decrease in coronary blood flow that follows a thrombotic occlusion of a coronary artery previously narrowed by arteriosclerosis. MI prophylaxis (primary and secondary prevention) is included as well as the acute treatment of MI and the prevention of complications. Ischemic disease is a condition in which the coronary flow is restricted resulting in a perfusion which is inadequate to meet the myocardial requirement for oxygen, such as stable angina, unstable angina and asymptomatic ischemia. Arrhythmias include atrial and ventricular tachyarrhythmias, atrial tachycardia, atrial flutter, atrial fibrillation, atrio-ventricular reentrant tachycardia, preexitation syndrome, ventricular tachycardia, ventricular flutter, ventricular fibrillation, as well as bradycardic forms of arrhythmias. Hypertensive vascular diseases include primary as well as all kinds of secondary arterial hypertension, renal, endocrine, neurogenic, others. Peripheral vascular diseases are vascular diseases in which arterial and/or venous flow is reduced resulting in an imbalance between blood supply and tissue oxygen demand and include chronic peripheral arterial occlusive disease (PAOD), acute arterial thrombosis and embolism, inflammatory vascular disorders, Raynaud's phenomenon and venous disorders. Atherosclerosis is a cardiovascular disease in which the vessel wall is remodeled, compromising the lumen of the vessel.

The active agents of the invention are administered to the subject in an effective amount for treating disorders such as neurological disorders and GSK3 disorders. An "effective amount", for instance, is an amount necessary or sufficient to realize a desired biologic effect. An "effective amount for treating Alzheimer's disease", for instance, could be that amount necessary to (i) prevent further memory loss and/or (ii) arresting or slowing memory loss with respect to memory loss in the absence of the therapy. According to some aspects of the invention, an effective amount is that amount of a compound of the invention alone or in combination with another medicament, which when combined or co-administered or administered alone, results in a therapeutic response to the disease, either in the prevention or the treatment of the disease. The biological effect may be the amelioration and or absolute elimination of symptoms resulting from the disease. In another embodiment, the biological effect is the complete abrogation of the disease, as evidenced for example, by the absence of a symptom of the disease.

The effective amount of a compound of the invention in the treatment of a disease described herein may vary depending upon the specific compound used, the mode of delivery of the compound, and whether it is used alone or in combination. The effective amount for any particular application can also vary depending on such factors as the disease being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The agent may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference). In a particular embodiment, intraperitoneal injection is contemplated.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the molecules of the invention are also contemplated. In some instances, when the molecules of the invention are administered with another medicament, such as an anti-neurological agent, a sub-therapeutic dosage of either the molecules or the anti-neurological agent, or a sub-therapeutic dosage of both, is used in the treatment of a subject having, or at risk of developing a neurological disorder. When the two classes of drugs are used together, the anti-neurological agent may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of an anti-neurological agent is one which would not produce the desired therapeutic result in the subject in the absence of the administration of the molecules of the invention. Therapeutic doses of anti-neurological agents are well known in the field of medicine. These dosages have been extensively described in references such as Remington's Pharmaceutical Sciences, 18th ed., 1990; as well as many other medical references relied upon by the medical profession as guidance for the treatment of neurological disorders.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

A variety of administration routes are available. The particular mode selected will depend, of course, upon the particular active agents selected, the particular condition being treated and the dosage required for therapeutic efficacy. The methods of this invention, generally speaking, may be practiced using any mode of administration that is medically acceptable, meaning any mode that produces effective levels of protection without causing clinically unacceptable adverse effects. Preferred modes of administration are parenteral routes. The term "parenteral" includes subcutaneous, intravenous, intramuscular, intraperitoneal, and intrasternal injection, or infusion techniques. Other routes include but are not limited to oral, nasal, dermal, sublingual, and local.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The compounds of the invention can be administered by any ordinary route for administering medications. Depending upon the type of cancer to be treated, compounds of the invention may be inhaled, ingested or administered by systemic routes. Systemic routes include oral and parenteral. Inhaled medications are preferred in some embodiments because of the direct delivery to the lung, particularly in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Preferred routes of administration include but are not limited to oral, parenteral, intramuscular, intranasal, intratracheal, intrathecal, intravenous, inhalation, ocular, vaginal, and rectal. For use in therapy, an effective amount of the compounds of the invention can be administered to a subject by any mode that delivers the nucleic acid to the affected organ or tissue. "Administering" the pharmaceutical composition of the present invention may be accomplished by any means known to the skilled artisan.

According to the methods of the invention, the compound may be administered in a pharmaceutical composition. In general, a pharmaceutical composition comprises the compound of the invention and a pharmaceutically-acceptable carrier. Pharmaceutically-acceptable carriers for peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

When the compounds described herein (including peptide and non-peptide varieties) are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the peptides (see, for example, Sciarra and Cutie, "Aerosols," in *Remington's Pharmaceutical Sciences*, 18th edition, 1990, pp 1694-1712; incorporated by reference). Those of skill in the art can readily determine the various parameters and conditions for producing aerosols without resort to undue experimentation.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application serial no. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include nonpolymer systems that are: lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic diseases. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Therapeutic formulations useful in the invention may be prepared for storage by mixing a peptide or other molecule having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to a patient, such as a syringe, topical application devices, or iv needle tubing and bag.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The invention further provides efficient methods of identifying pharmacological agents or lead compounds for agents and molecules that activate the DISC1 pathway, for instance by inhibiting GSK3 activity or increasing DISC1 activity. Generally, the screening methods involve assaying for compounds which modulate the amount of activity of DISC1 and or GSK3. As will be understood by one of ordinary skill in the art, the screening methods may measure the amount of activity directly, by using methods well known in the art. In addition, screening methods may be utilized that measure a secondary effect of DISC1 and or GSK3, for example detecting bound DISC1-GSJK3 or measuring GSK3 catalyzed phosphorylation.

A wide variety of assays for pharmacological agents can be used in accordance with this aspect of the invention, including, labeled in vitro protein-protein binding assays, electrophoretic mobility shift assays, immunoassays, kinase assays, cell-based assays such as two- or three-hybrid screens, expression assays, etc. Some exemplary assays are provided in the Examples below. The assay mixture comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents useful in accordance with the invention encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with proteins and/or nucleic acid molecules, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid molecule, the agent typically is a DNA or RNA molecule, although modified nucleic acid molecules as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the activity of DISC1 and or GSK3 is detected by any convenient method available to the user. For cell-free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost. For kinase assays, phosphorylation may be detected using antibodies or radiography.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens, such as reporter gene transcription as described in the Examples below. For cell-free binding assays, at least one of the components usually comprises, or is coupled to, a detectable label. A wide variety of labels can be used, such as those that provide direct detection (e.g., radioactivity, luminescence, optical or electron density, energy transfer, etc.) or indirect detection (e.g., epitope tag such as the FLAG or myc epitopes, enzyme tag such as horseradish peroxidase, etc.). A variety of methods may be used to detect the label, depending on the nature of the label and other assay components. For example, the label may be detected while bound to the solid substrate or subsequent to any separation from the solid substrate. Labels may be directly detected through optical or electron density, radioactive emissions, nonradiative energy transfers, etc. or indirectly detected with antibody conjugates, strepavidin-biotin conjugates, etc. A variety of methods for detecting the labels are well known in the art.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods

Mice. Swiss Webster pregnant female mice were purchased from Taconic (Hudson, N.Y.).

Cell culture. AHPs were kindly provided by Dr. Gage (Lie, D. C. et al. Wnt signaling regulates adult hippocampal neurogenesis. Nature 437, 1370-5 (2005)) and cultured under conditions described previously (Palmer, T. D., Takahashi, J. & Gage, F. H. The adult rat hippocampus contains primordial neural stem cells. Mol Cell Neurosci 8, 389-404 (1997)). Primary neural progenitors were isolated from E14 mouse embryos and cultured as described previously (Sanada, K. & Tsai, L. H. G protein betagamma subunits and AGS3 control spindle orientation and asymmetric cell fate of cerebral cortical progenitors. Cell 122, 119-31 (2005)). N2a and 293T cells were cultured in DMEM medium containing 10% FBS, L-glutamine, and penicillin/streptomycin. Wnt3a expressing L cells and untransfected L cells were obtained from ATCC (Manassas, Va.). Wnt3a conditional medium was produced according to the ATCC protocol. To induce AHP differentiation, FGF2 was removed from the culture medium and 1 µM retinoic acid/1% FBS was added to the medium for 4 days.

Reagents. Recombinant Wnt3a protein was obtained from Chemicon (Rosemont, Ill.). FGF2 was obtained from Pepro-Tech (Rocky Hill, N.J.). Recombinant GST-GSK3β was obtained from Active Motif (Carlsbad, Calif.). Recombinant GST-β-catenin and GST-axin were obtained from Millipore (Billerica, Mass.). The GSK3β inhibitor, SB-216763, AR-A104418 and His-GSK3β, were obtained from Sigma-Aldrich (Sigma-Aldrich, St. Louis, Mo.). L803-MTS was obtained from Calbiochem (San Diego, Calif.). GST-AKT1 was obtained from Cell Signaling (Beverly, Mass.). GST-CASK-1 (CASK fragment from 316-415aa), GST-CASK-2 (CASK fragment from 777-974aa), and GST-p25 proteins were kindly provided by Dr. B.A. Samuels. Mouse DISC1 peptide1 (40-78aa: GYMRSTAGSG IGFLSPAVG-MPHPSSAG LTGQQSQHSQS; SEQ ID NO: 1) and Mouse DISC1 peptide 2 (195-238aa, PADIASLPGFQDTFTSSFS-FIQLSLGAA GERGEAEGCLPSREAE; SEQ ID NO: 2) were synthesized by Chi Scientific (Maynard, Mass.).

Antibodies. The primary antibodies used in this study were the following: rabbit anti-DISC 1 C-terminal antibody, mouse and rabbit anti-GFP antibodies (Invitrogen, Carlsbad, Calif.); affinity purified rabbit anti-DISC1 antibody (Novus, Littleton, Colo.) for immunohistochemistry; mouse anti-FLAG and mouse anti-Actin antibody; mouse anti-GSK3β antibody, mouse anti-β-catenin antibody, mouse anti-pY216 GSK3β antibody, and mouse anti-nestin antibody (BD Biosciences, San Diego, Calif.); rabbit anti-p93/97/T41 β-catenin antibody, rabbit anti-pS9 GSK3β antibody, and mouse anti-cyclin D1 antibody (Cell Signaling); mouse anti-Dvl2 antibody, mouse anti-HA antibody, mouse anti-GST antibody, mouse anti-ubiquitin antibody, and rabbit anti-3-catenin antibody (Santa Cruz, Santa Cruz, Calif.); mouse Tuj-1 antibody (BABCO, Harrisburg, Pa.); mouse anti-BrdU antibody (DakoCytomation, Glostrup, Denmark); guinea pig anti-doublecortin antibody (Chemicon, Rosemont, Ill.); chicken anti-GFP antibody (Aves Labs, Tigard, Oreg.); rabbit anti-pS10 Histone H3 antibody (Upstate, Lake Placid, N.Y.).

Constructs. The sequences for shRNAs targeting DISC1 are as follows: control shRNA: 5'-CGGCTGAAACAAGAGT-TGG-3' (SEQ ID NO:3); DISC1 shRNA-1: 5'-GGCAAA-CACTGTGA AGT GC-3' (SEQ ID NO:4); DISC1 shRNA-2: 5'-GCAGGAGGTCAGCAAGGCCTTG-3' (SEQ ID NO:5) (Kamiya A. et al. A schizophrenia-associated mutation of DISC1 perturbs cerebral cortex development. Nat. Cell Biol 7, 1167-78 (2005)). DISC1 shRNA-1 recognizes both rat and mouse DISC1. DISC1 shRNA-2 targets human, rat, and mouse DISC1. shRNA oligoribonucleotides were cloned into the pLentiLox 3.7 vector (Rubinson, D. A. et al. A lentivirus-based system to functionally silence genes in primary mammalian cells, stem cells and transgenic mice by RNA interference. Nat Genet. 33, 401-6 (2003)). β-catenin shRNAs were obtained from the Broad Institute RNA interference platform (Cambridge, Mass.) and the sequences are as follows: β-catenin shRNA-1: 5'-CTGATATTGACGGGCAG-TAT-3' (SEQ ID NO:6), β-catenin shRNA-2: 5'-CCCAAGC-CTTAGTAAACATAA-3' (SEQ ID NO:7). The full length mouse DISC1 cDNA was generously provided by Dr. Cris Brag. Four different fragments (1-220aa, 221-355aa, 356-595aa, and 596-852aa) from mouse DISC1 cDNA were amplified by PCR and subcloned into pGEX-4T2 to generate GST fusion constructs. The full length human DISC1 cDNA was generously provided by Dr. A. Sawa (John Hopkins University, Baltimore, Md.). The full length human DISC1 was amplified by PCR and subcloned into the pOZ-N retroviral vector to generate a HA-FLAG-tagged WT-DISC1 expressing vector. HA-FLAG-tagged WT-DISC1 was subcloned upstream of the IRES and GFP in the lentiviral vector, FUGW (Scott, B. B. & Lois, C. Generation of tissue-specific transgenic birds with lentiviral vectors. Proc Natl Acad Sci USA 102, 16443-7 (2005)), provided by Dr. C. Lois (MIT, Cambridge, Mass.). Concentrated lentivirus was produced as previously described (Millar, J. K. et al. DISC1 and PDE4B are interacting genetic factors in schizophrenia that regulate cAMP signaling. Science 310, 1187-91 (2005)). Viral titers, as determined by GFP expression in 293T cells, were $5 \times 10^8$-$1 \times 10^9$ transducing units per ml. Super 8× TOPFLASH (which contains 8 copies of the TCF/LEF binding site), a gift from Dr. R. Moon (University of Washington, Seattle, Wash.) and a Renilla-Luc-TK reporter (pRL-TK, Promega, Madison, Wis.) was used for testing TCF transcriptional activity. FLAG-Dvl2 and FLAG-β-catenin (WT and 93A) were provided by Dr. X. He (Harvard Medical School, Boston, Mass.). HA-GSK3β was provided by Dr. X. He. pCAGIG-Venus was provided by Dr. Zhigang Xie (Boston University, Boston, Mass.).

Cell proliferation analysis. N2a and AHP cells were transduced with lentivirus expressing DISC1 shRNA-1, DISC1 shRNA-2 or WT-DISC1 for 2 days. The transduced cells were sorted by FACS based on GFP expression. $2 \times 10^4$ cells were seeded into 12 well plates with medium and cell number was counted each day for 2 days (AHP) or 3 days (N2a cells). In the AHP proliferation assay, recombinant Wnt3a protein (200 ng/ml) or vehicle was added to the medium to determine the proliferation in response to Wnt3a stimulation.

In utero electroporation. E13 mice were used for in utero electroporation as described previously (Sanada, K. & Tsai, L. H. G protein betagamma subunits and AGS3 control spindle orientation and asymmetric cell fate of cerebral cortical progenitors. Cell 122, 119-31 (2005)). Detailed procedures are provided in the supplemental methods. For cell cycle exit and rescue experiments, mice were intraperitoneally (i.p.) injected with BrdU (100 mg/kg) 2 days after electroporation and sacrificed 24 hours later.

Immunohistochemistry and immunocytochemistry. Immunohistochemistry and immunocytochemistry were performed as described previously (Sanada, K. & Tsai, L. H. G protein betagamma subunits and AGS3 control spindle orientation and asymmetric cell fate of cerebral cortical progenitors. Cell 122, 119-31 (2005)). Transduced AHPs were seeded onto polyornithine and fibronectin coated coverslips.

BrdU (10 µM) was added to the culture medium for 2 hours. Cells were fixed in 4% paraformaldehyde and stained with anti-BrdU or pH3 antibodies. Five random fields from each experiment were obtained and over 500 cells were counted for each experiment.

Luciferase assays. $5\times10^5$ transduced AHPs, embryonic progenitors, or 293T cells were seeded into 24-well plates and transfected with 0.8 µg of Super8×TOPFLASH or Super8× FOPFLASH and 0.1 µg of pRL-TK using Lipofectamine 2000 (Invitrogen). 24 hours after transfection, transfected cells were stimulated with Wnt3a-conditioned medium (Wnt3a CM) for 14 hours and TCF reporter activity was measured using the Dual-Luciferase Assay System (Promega). For the rescue experiment, 1.6 µg of vector, Dvl2, WT-β-catenin, or SA-β-catenin was cotransfected with 0.4 µg of Super8×TOPFLASH and 0.1 µg of pRL-TK using Lipofectamine 2000, and transfected cells were treated with Wnt3a (200 ng/ml). For the in utero TCF reporter assay, expression vector: Super 8×TOPFLASH: pRL-TK constructs was electroporated into embryonic brains at a 5:1:0.3 ratio. For the knockdown experiments, we used E13 mice for electroporation and measured TCF activity at E15. For overexpression experiments, we electroporated at E14 and measured TCF activity at E15. All firefly luciferase activities were normalized with renilla luciferase activity.

Immunoblot and immunoprecipitation. Immunoblots and immunoprecipitations were performed as described previously (Mao, Y. & Lee, A. W. A novel role for Gab2 in bFGF-mediated cell survival during retinoic acid-induced neuronal differentiation. J Cell Biol 170, 305-16 (2005)).

Image acquisition and statistical analysis. All images were acquired using a confocal Zeiss LSM 510 microscope. Images were further analyzed by Adobe Photoshop and ImageJ v1.37. Statistical analysis was performed using the student t-test. All bar graphs are plotted as the mean±s.d.

FACS cell cycle analysis. N2a cells were transfected with control or DISC1 shRNAs. 48 hours after transfection, cells were fixed with 2% paraformaldehyde and permeabalized with 75% ethanol. FACS analysis was conducted as described previously (Beaulieu, J. M. et al. Lithium antagonizes dopamine-dependent behaviors mediated by an AKT/glycogen synthase kinase 3 signaling cascade. Proc Natl Acad Sci USA 101, 5099-104 (2004)).

In vitro binding and kinase assay. GST pull-down assays were conducted as described previously (Mao, Y. W., Liu, J. P., Xiang, H. & Li, D. W. Human alphaA- and alphaB-crystallins bind to Bax and Bcl-X(S) to sequester their translocation during staurosporine-induced apoptosis. Cell Death Differ 11, 512-26 (2004)). Briefly, 5 µg of purified GST-DISC1 fragments were incubated with glutathione-Sepharose beads (GE) for one hour. Beads were then washed with 1×PBS, 1% Triton X-100, 5 mM EDTA, 1 mM DTT, and 0.1 mM PMSF four times. 5 µg of recombinant His-GSK3β protein was then incubated with beads for one hour and nonspecific proteins were washed off 4 times with RIPA buffer and twice with lysis buffer (150 mM NaCl, 0.1% NP40, 50 mM Tris, pH7.5, 5 mM EDTA). Associated proteins were assessed by Western blot with an anti-GSK3β antibody. For the GSK3β in vitro kinase assay, 1 µM of purified DISC1 protein was incubated with 5 ng/l GST-GSK3β in kinase buffer (2 mM MOPS, pH7.4, 0.05 mM EDTA, 2.5 mM MgAcetate, 100 µM ATP, 10 µCi of $^{32}$P-ATP, 10 mM $MgCl_2$) and 18.75 ng/µl GST-axin or GST-β-catenin for 15 minutes at 30° C. Kinase activity was measured using the anti-pY216 GSK3β antibody (BD) or radiography. For AKT kinase assay, 5 µM of purified DISC1 protein was incubated with 10 ng/µl GST-AKT1 (Cell Signaling) in kinase buffer (5 mM MOPS, pH 7.2, 2.5 mM β-glycerophosphate, 1 mM EGTA, 0.4 mM EDTA, 5 mM $MgCl_2$, 0.05 mM DTT, 50 µM ATP, 1 µCi $^{32}$P-ATP) at room temperature for 30 min. Autophosphorylation of AKT1 was detected by radiography.

Stereotaxic injection. 1 µl of high titer lentivirus ($\sim2\times10^9$ transducing units/ml) was injected into the dentate gyrus of 8 week old mice bilaterally (AP −2, ML±1.5, DV −1.8 from Bregma, n=15 per group). Following 4 weeks of recovery, mice i.p. injected with SB216763 (2 mg/kg) every other day for another two weeks. BrdU (100 mg/kg) was injected daily for the last week. The mice were then perfused with 4% paraformaldehyde and the brains were processed for staining with an anti-BrdU antibody.

In utero BrdU labeling. Control or DISC1 shRNA constructs were injected into E13 embryonic brains with an enhanced GFP (EGFP)-expressing plasmid (final concentration, 2 µg/µl; pCAGIG-Venus) at 2:1 ratio. In the rescue experiments, the concentration of human WT-DISC1 or SA-β-catenin plasmid was 2 fold higher than shRNA constructs. 48 hours after electroporation, BrdU (100 mg/kg) was i.p. injected into mice. After 2 hours, brains were processed and sections (20-µm thick) were co-stained with anti-GFP and anti-BrdU or anti-pH3 antibodies. In the rescue experiments, brains were harvested 24 hours after BrdU injection. Brain sections were then co-stained with anti-GFP and anti-BrdU antibodies. The distribution of GFP positive cells was determined by dividing the number of GFP positive cells in each layer by the total number of GFP-positive cells in the entire section.

Example 1

DISC1 Expression

Figure 7D:
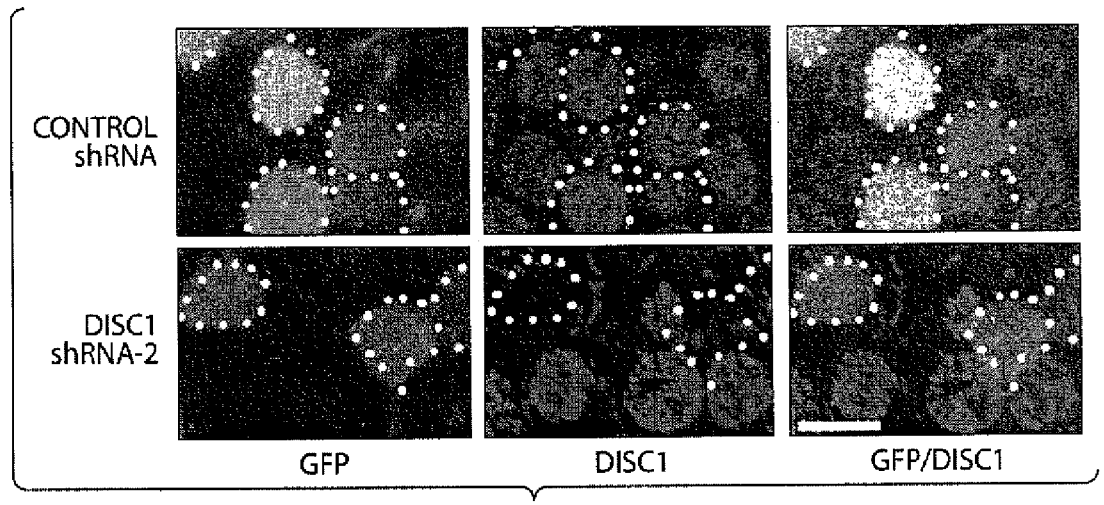

Accumulating evidence supports a neurodevelopmental basis for schizophrenia (Ross, C. A., Margolis, R. L., Reading, S. A., Pletnikov, M. & Coyle, J. T. Neurobiology of schizophrenia. Neuron 52, 139-53 (2006); Chubb, J. E., Bradshaw, N.J., Soares, D. C., Porteous, D. J. & Millar, J. K. The DISC locus in psychiatric illness. Mol Psychiatry 13, 36-64 (2008); Arnold, S. E. Neurodevelopmental abnormalities in schizophrenia: insights from neuropathology. Dev Psychopathol 11, 439-56 (1999)). Expression of DISC1 peaks at E14-E15 in mouse embryonic brains, a period of active neurogenesis in the cortex, and gradually declines as development proceeds (data not shown) (Schurov, I. L., Handford, E. J., Brandon, N.J. & Whiting, P. J. Expression of disrupted in schizophrenia 1 (DISC1) protein in the adult and developing mouse brain indicates its role in neurodevelopment. Mol Psychiatry 9, 1100-10 (2004)). In adult mice, DISC1 is robustly expressed in the dentate gyrus (DG) and olfactory bulb, two regions displaying active neurogenesis (Ma, L. et al. Cloning and characterization of Disc1, the mouse ortholog of DISC1 (Disrupted-in-Schizophrenia 1). Genomics 80, 662-72 (2002)) in adult brains. We also performed immunohistochemistry to determine the distribution pattern of DISC1 in the developing cerebral cortex. DISC1 is highly expressed in the ventricular zone (VZ)/subventricular zone (SVZ), where nestin-positive neural progenitors and Sox2-positive neural progenitors reside (FIGS. 1a, b) and the cortical plate (CP), where postmitotic neurons reside (FIG. 1a), but is reduced in double-cortin (DCX) positive neurons. Furthermore, we found that DISC1 is expressed in cells labeled by a 2 hour BrdU pulse (FIGS. 7a and b), and positive for the mitotic marker, phospho-histone H3 (pH3) (FIG. 7c), further confirming that DISC1 is expressed in neural progenitors. The specificity of DISC1 staining was verified using embryonic mouse brains electroporated with a DISC1 short hairpin RNA sequence (shRNA), where diminished DISC1 signal was observed in transfected (GFP+) progenitor cells (FIG. 7d). This result indicates that DISC1 may function in the proliferating cortical progenitors during embryonic cortical development.

Example 2

Role for DISC1 in Progenitor Proliferation

Figure 1C:
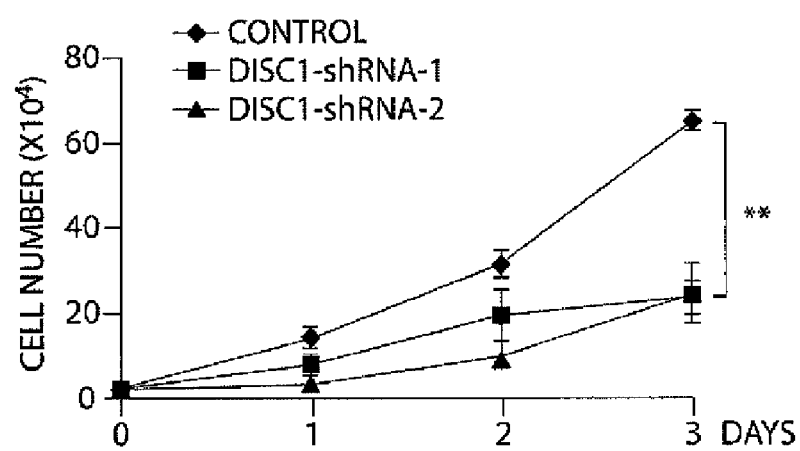
Figure 1D:
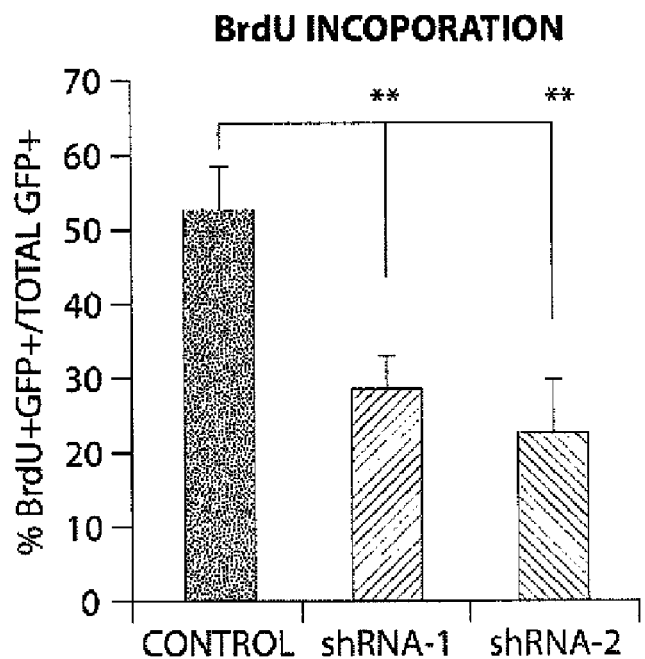
Figure 1E:
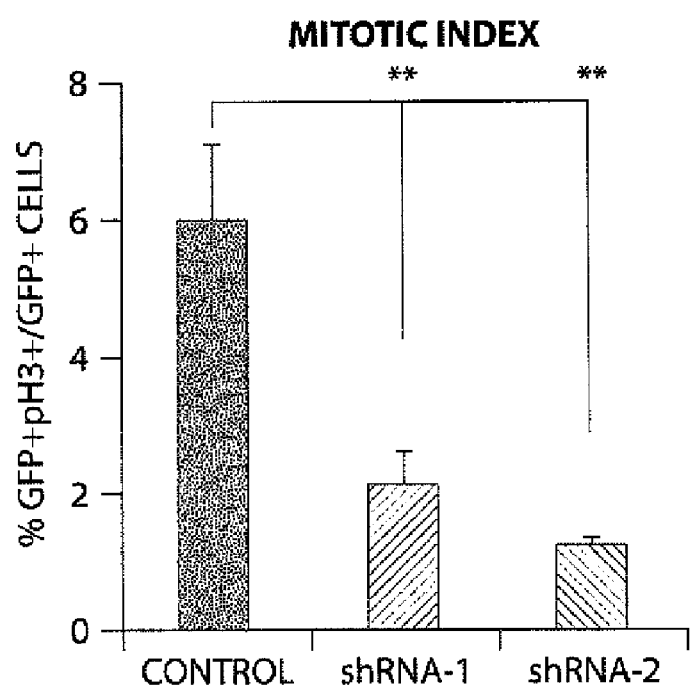
Figure 1F:
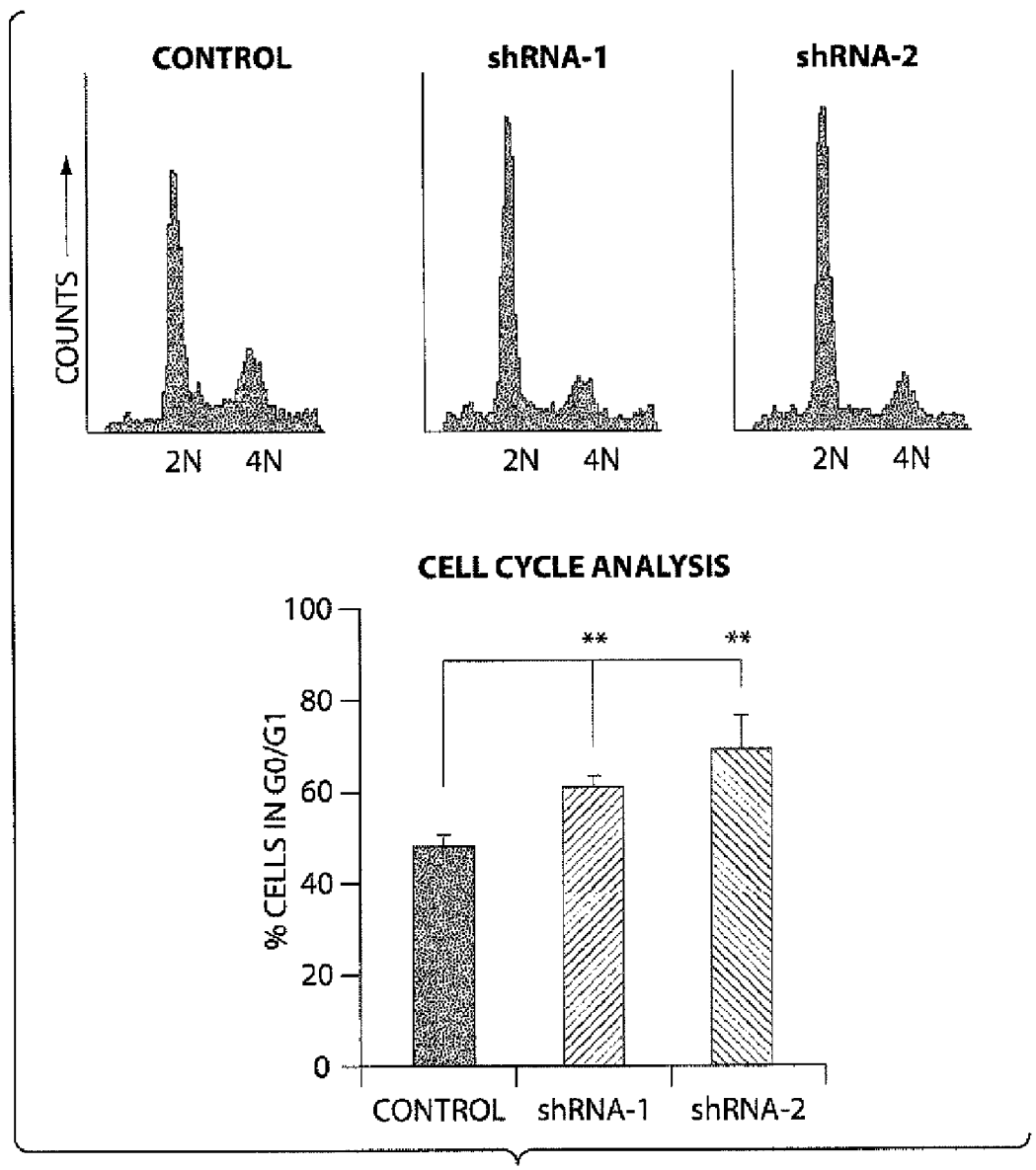
Figure 1G:
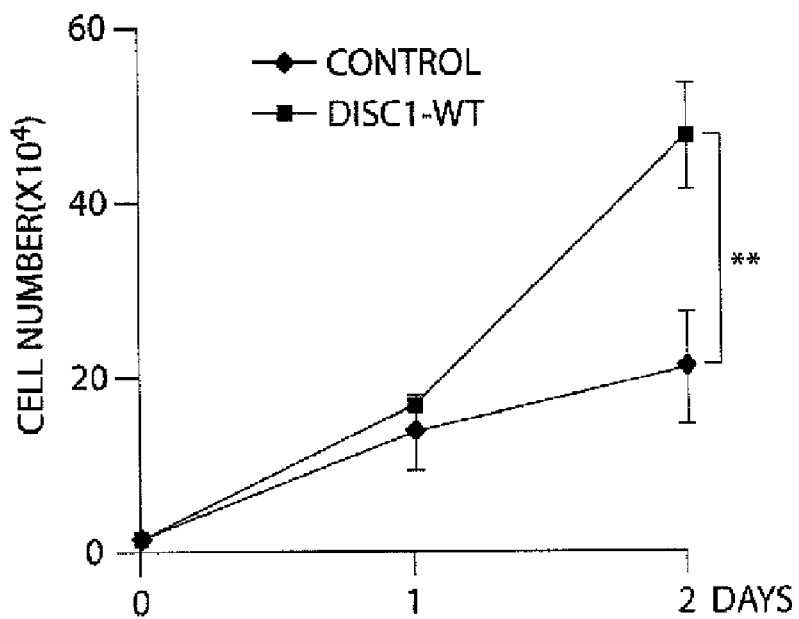
Figure 1H:
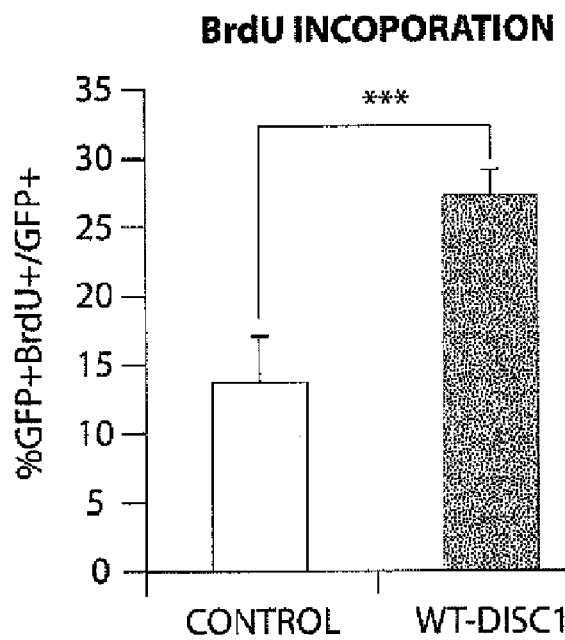
Figure 1I:
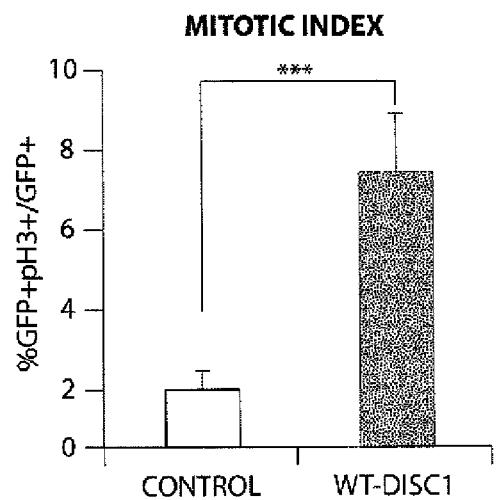
Figure 8A:
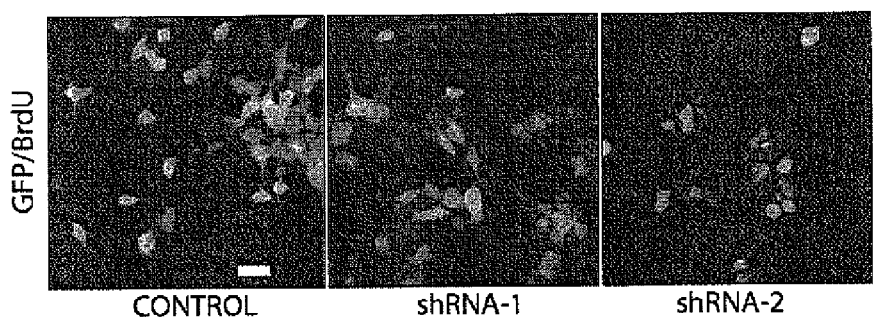
Figure 8B:
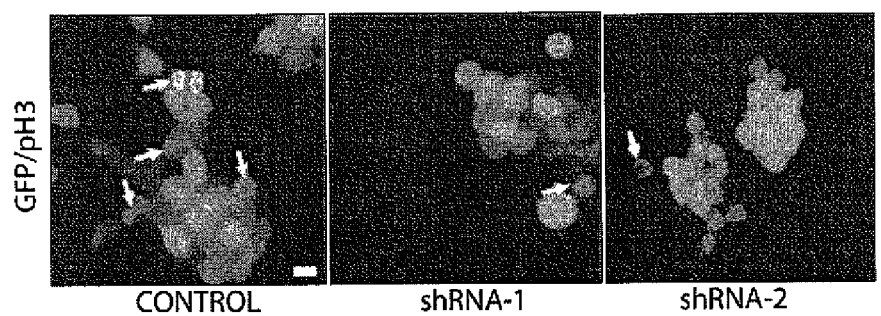
Figure 8C:
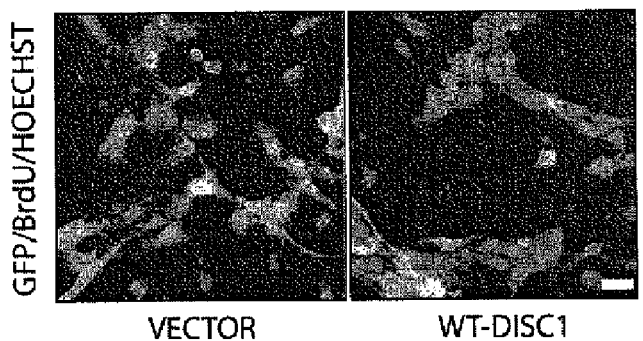
Figure 8D:
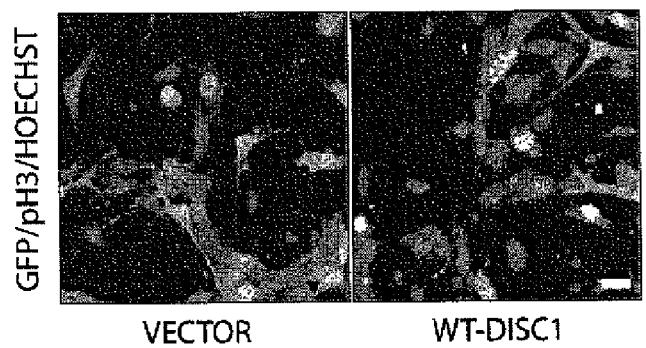

Based on its expression in neural progenitors, we looked into a potential role for DISC1 in progenitor proliferation. To approach this, we generated two specific shRNAs that silenced endogenous DISC1 expression (shRNA1 and shRNA2; FIG. 2). Upon transduction of adult hippocampal progenitor (AHP) cells with lentivirus expressing control or DISC1 shRNAs, we observed that DISC1 knockdown significantly decreased the total number of cells compared to cells expressing the control shRNA (FIG. 1c). Moreover, cells receiving DISC1 shRNA displayed a 2 fold decrease in BrdU labeling (2 hr pulse) (FIG. 1d, FIG. 8a) and a 3 fold decrease in mitotic index (FIG. 1e, FIG. 8b). FACS analysis revealed that DISC1 knockdown significantly increased the portion of cells in G0/G1, and decreased cells in S phase and mitosis (FIG. 1f). The reduction of proliferation by suppression of DISC1 expression prompted us to pursue the reciprocal DISC1 gain-of-function experiment. Interestingly, overexpression of full length human DISC1 resulted in a roughly 2 fold increase in cell number (FIG. 1g). This was accompanied by a 2 fold increase in BrdU labeling (FIG. 1h, FIG. 8c) and a 3 fold increase in mitotic index (FIG. 1i, FIG. 8d). Thus, in addition to its requirement in normal proliferation, DISC1 overexpression has the capacity to promote proliferation. Similar results were obtained with primary embryonic neural progenitors (data not shown).

Example 3

Role for DISC1 in Neural Progenitor Proliferation In Vivo

We next investigated whether DISC1 regulates neural progenitor proliferation in vivo. Control or DISC1 shRNA constructs were electroporated together with a GFP-expressing vector into E13 mouse brains, and analyzed 3 days later. During embryonic brain development, neural progenitors actively divide in the ventricular zone (VZ) and subventricular zone (SVZ). Upon evaluation of the positioning of GFP positive cells, we found that DISC1 knockdown caused a substantial reduction of cells in the VZ/SVZ (FIG. 2a, 30% GFP positive cells with control shRNA versus 13% in DISC1 shRNA-1 and 10% in shRNA-2 electroporated brains). There was a corresponding increase in GFP positive cells in the cortical plate (40.2% in control versus 59.6% in shRNA-1 and 62% in shRNA-2 electroporated brains). Therefore, DISC1 loss-of-function causes a depletion of cells from the proliferative VZ/SVZ.

To decipher the mechanism behind the observed difference in cell positioning caused by DISC1 knockdown, we repeated the in utero electroporation, but injected BrdU into the pregnant dams 2 hours prior to collection of the transfected brains. We observed a marked reduction in BrdU labeling (FIG. 9a, 33.3±5.6% in control shRNA, 18.2±2.2% in shRNA-1, 15.9±2.2% in shRNA-2) and mitotic index (FIG. 2b, 10.4±1.2% in control shRNA, 3.8±0.8% in DISC1 shRNA-1, 3.5±0.8% in shRNA-2) in DISC1 shRNA electroporated brains. To confirm the specificity of the shRNA experiments, we performed RNAi rescue experiments by co-electroporating DISC1 shRNA-1 with human DISC1 cDNA (not targeted by shRNA-1) into E13 mouse brains. Expression of human DISC1 rescued the cell positioning and proliferation defects caused by DISC1 shRNA knockdown (FIGS. 5a, b), demonstrating that DISC1 is required to maintain the proliferative potential of cortical progenitors in vivo.

Figure 2A:
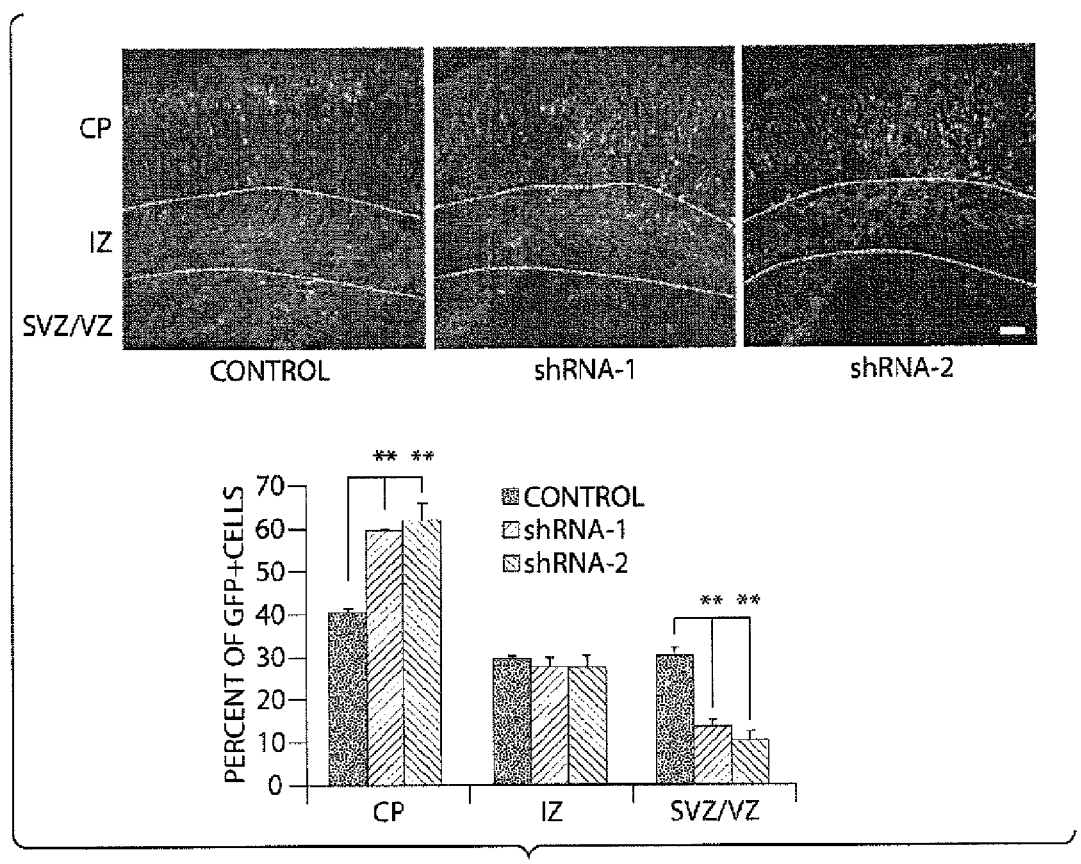
FIG. 2 shows that DISC1 regulates progenitor cell proliferation in utero. a. DISC1 knockdown cells exhibit cell positioning defects in utero. Control or DISC1 shRNA constructs were electroporated into E13 embryonic mouse brains and the mice were sacrificed at E16. Brain sections were stained with anti-GFP antibody. The percentage of GFP cells in each region is shown (n=4, p<0.01). Scale bar=50 µm. CP, cortical plate; IZ, intermediate zone; VZ/SVZ, ventricular zone/subventricular zone. b. Mitotic index of DISC1 silenced cells is reduced in utero. Control or DISC1 shRNA constructs were electroporated into E13 embryonic brains and mice were sacrificed at E15. Brain sections were costained with GFP and pH3 antibodies. The percentage of GFP positive cells that are also pH3 positive in the ventricular zone is shown (n=4, p<0.01). Scale bar=20 µm. Arrowheads indicate GFP and pH3 double positive cells. c. DISC1 knockdown in progenitor cells causes premature cell cycle exit in utero. Control or DISC1 shRNA constructs were electroporated into E13 embryonic brains and BrdU was injected at E15. Mice were sacrificed at E16. The cell cycle exit index is measured as the percentage of the GFP-positive cells that exited the cell cycle (GFP+BrdU+Ki67-) divided by total GFP and BrdU double positive (GFP+BrdU+) cells (n=5, p<0.001). Scale bar=20 µm. White arrows indicate GFP+BrdU+Ki67+ cell. Arrowheads indicate GFP+BrdU+Ki67− cells. d. DISC1 knockdown cells undergo premature neuronal differentiation in utero. Control or DISC1 shRNA constructs were electroporated into E13 embryonic brains and mice were sacrificed at E16. Brain sections were co-stained with anti-GFP and anti-DCX antibodies. The percentage of GFP and DCX double positive cells in the SVZ is shown (n=3, p<0.01). Scale bar=20 µm. e. BrdU labeling is increased in DISC1 overexpressing cells in utero. Control or WT-DISC1 plasmids were electroporated into embryonic brains at E14 and BrdU was injected 2 hours before sacrificing at E15. Brain sections were stained with anti-GFP antibody and anti-BrdU antibody. The percentage of GFP positive cells in each region and the percentage of GFP positive cells that are also BrdU positive cells in the SVZ is shown (n=3, * p<0.05, ***p<0.005). Scale bar=20 µm.
Figure 2B:
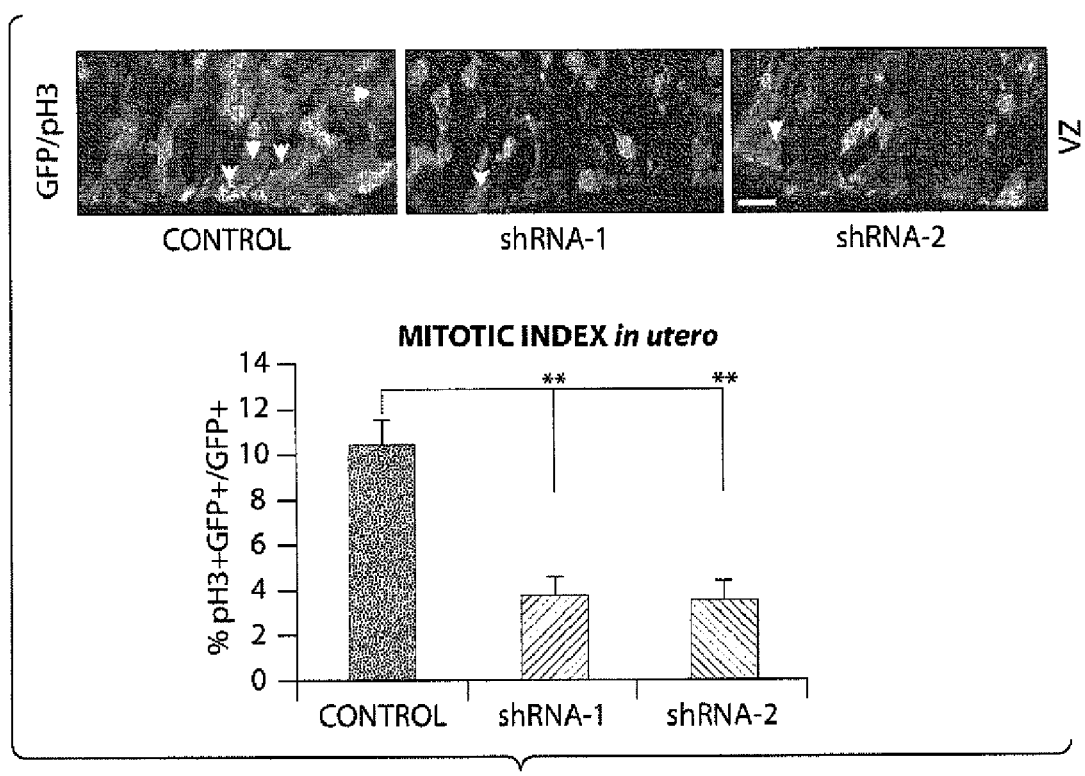
Figure 2C:
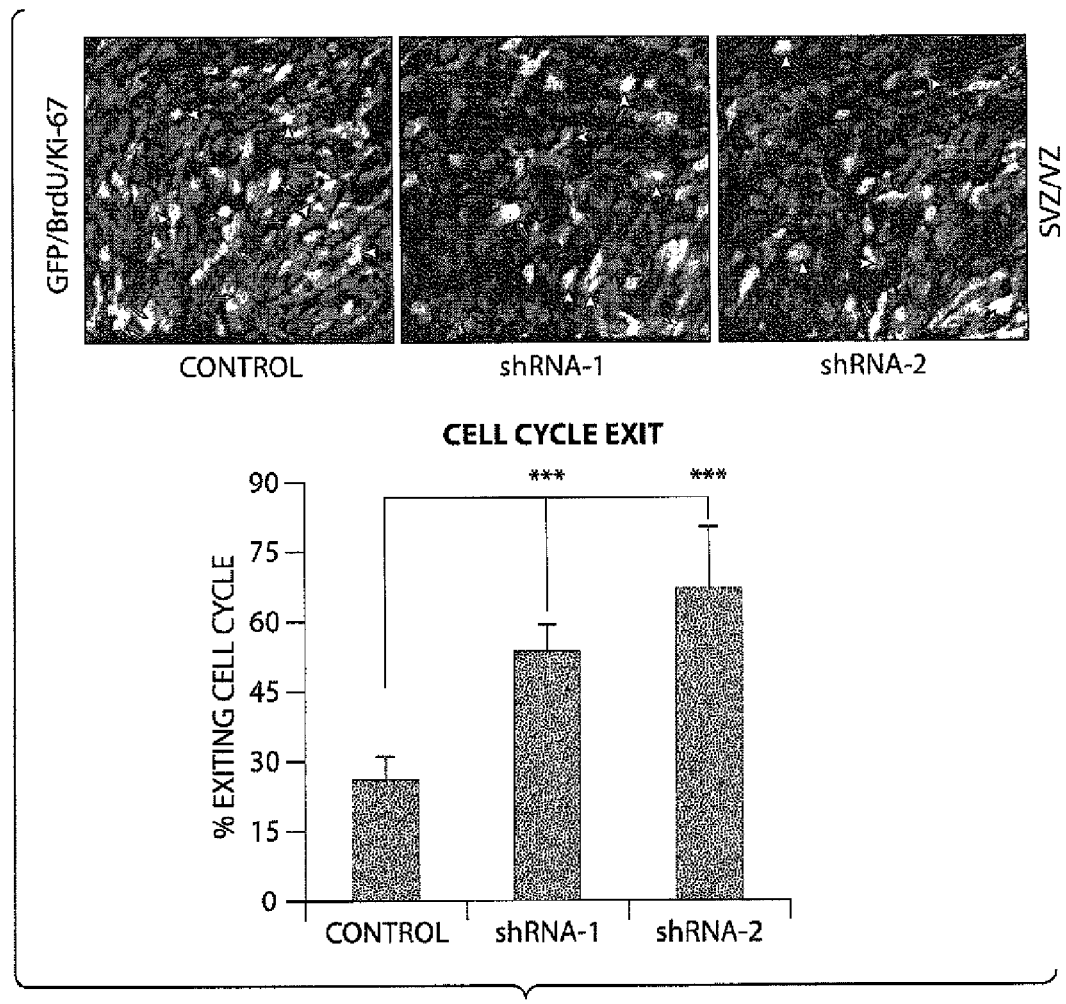
Figure 2D:
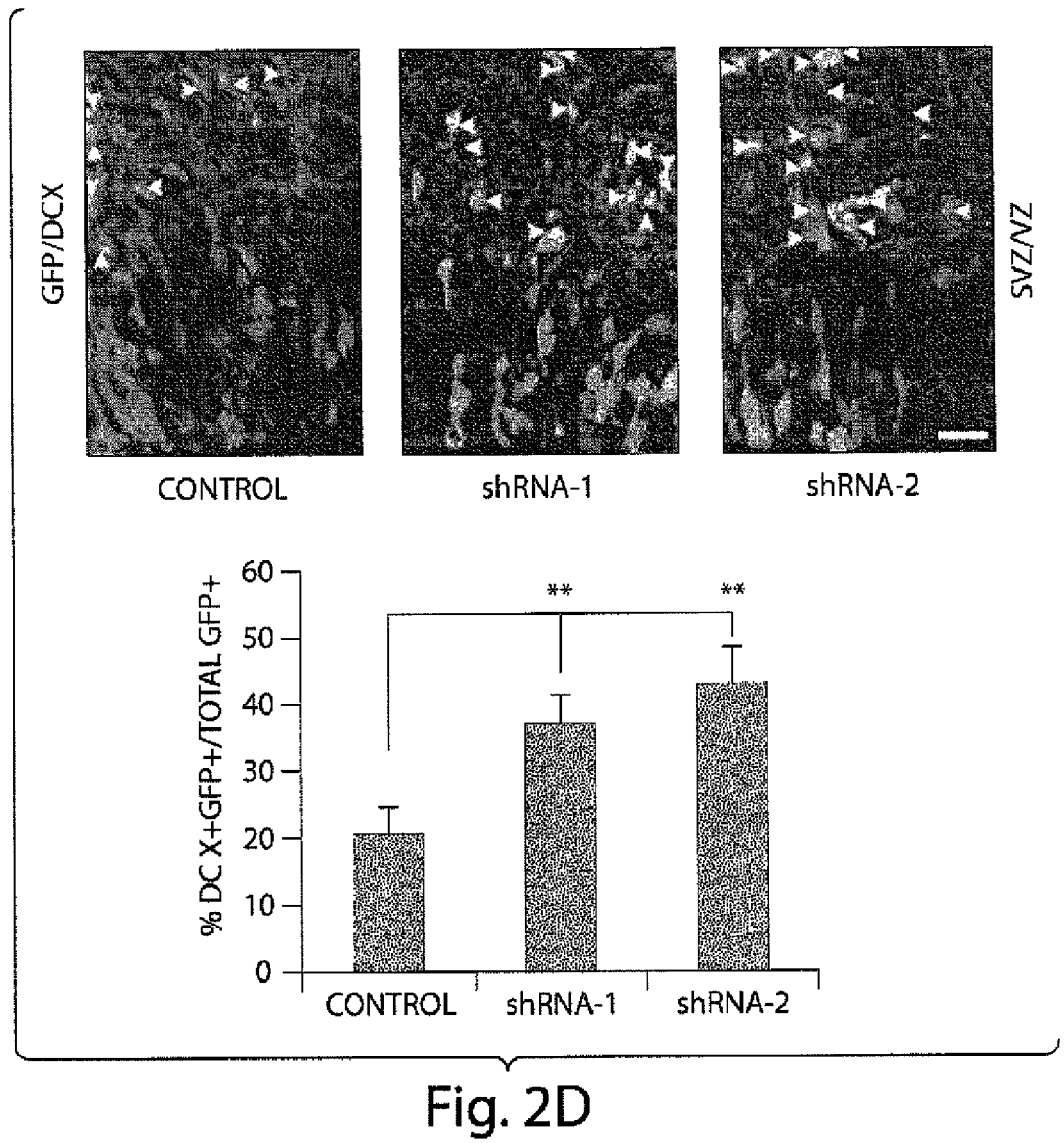
Figure 2E:
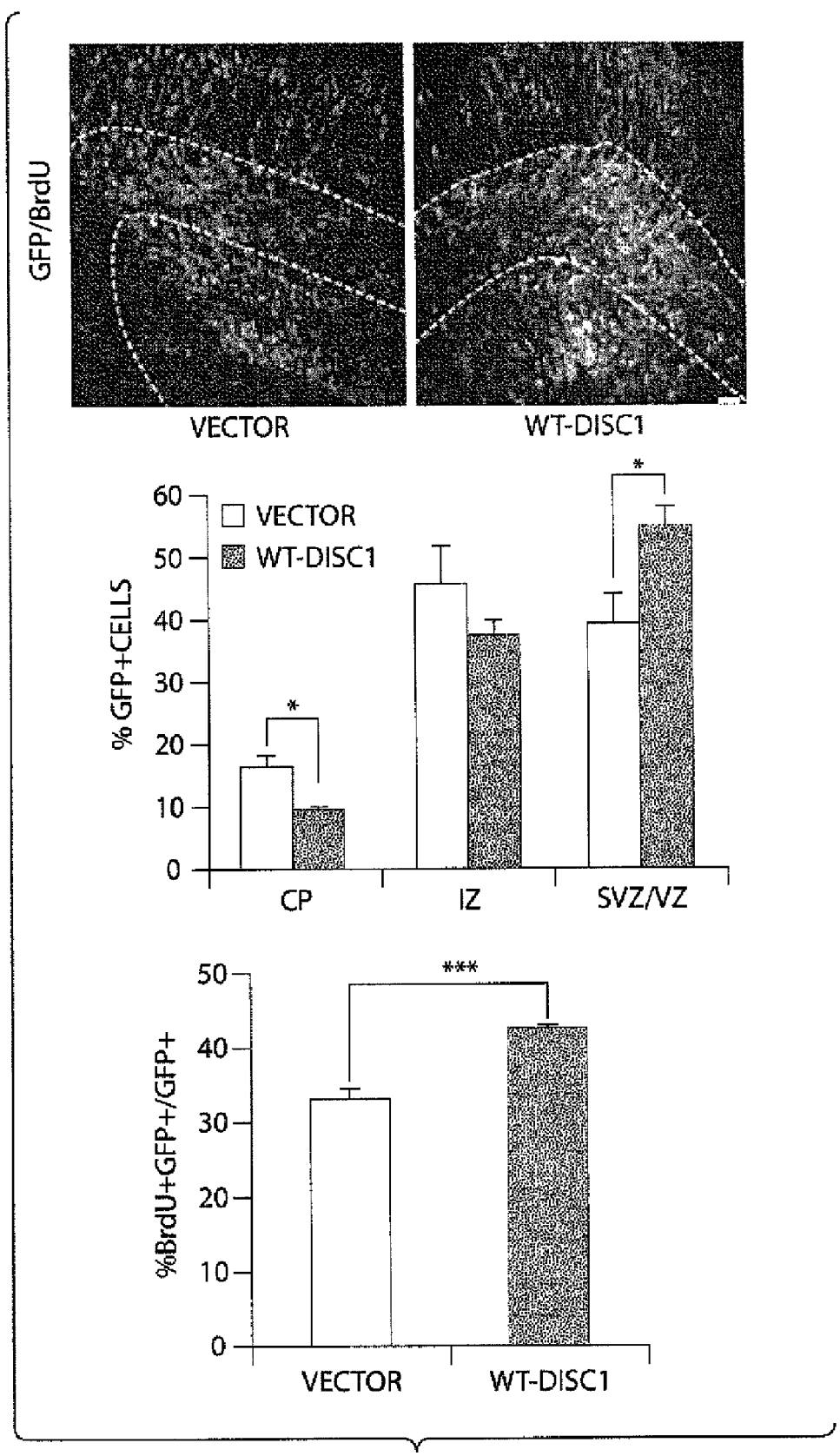

Our observations that DISC1 knockdown reduces neural progenitor proliferation and decreases the percentage of cells positioned in the VZ/SVZ implied that cells may be prematurely differentiating into neurons. To test this possibility, we measured the cell cycle exit index. E13 mouse brains were electroporated with DISC1 shRNA constructs and BrdU was injected 2 days later at E15 into pregnant dams. At E16, brains were collected and analyzed by immunohistochemistry using anti-GFP, -BrdU, and -Ki67 (a proliferation marker for cells in late G1, S, G2 and M phases) antibodies. GFP+/BrdU+/Ki67+ cells (arrows) were in S phase at E15 and remain cycling at E16 (FIG. 2c). GFP+/BrdU+/Ki67-cells were in S phase at E15, but exited the cell cycle by E16 (arrowheads). The cell cycle exit index represents the ratio of GFP+/BrdU+/Ki67-to total GFP+/BrdU+ cells. In embryonic brains transfected with DISC1 shRNA constructs, a 2-3 fold increase in cell cycle exit index was observed compared to control shRNA construct transfected brains (25.8±5.5% in control, 53.2±6.1% in shRNA-1, 66.5±13.2% in shRNA-2). These data indicate that reduction of proliferating progenitors in DISC1 shRNA treated brains is likely the consequence of increased cell cycle exit. To further evaluate the fate of the cells that exited the cell cycle, we immunostained the brain sections for doublecortin (Dcx), a marker for newly generated neurons (FIG. 2d). A significant increase in Dcx positive cells and decrease in Sox2-postitive cells was observed with DISC1 shRNA transfected cells (36.7±4.2% GFP+Dcx+ cells for shRNA-1 and 42.3±5.8% for shRNA-2) compared to control shRNA transfected cells (20.1±4.3%) (FIG. 2d). Supporting the premature neuronal differentiation, we found that DISC1 knockdown in E15 brains resulted in a significantly higher proportion of Cux2 (layer 2 and 3 marker) positive cells at postnatal day 7 compared to the control. Taken together, these results indicate that loss of DISC1 expression causes premature neuronal differentiation at the expense of the progenitor pool. Conversely, overexpression of DISC1 increased both the percentage of cells remaining in the VZ/SVZ (38.76±4.35% GFP positive cells in the SVZ/VZ of control brains versus 54.09±2.80% GFP positive cells in DISC1 overexpressing brains) and the BrdU labeling index (FIG. 2e). These observations further support a role for DISC1 in the proliferation of neural progenitors during cortical development.

Example 4

Figure 3A:
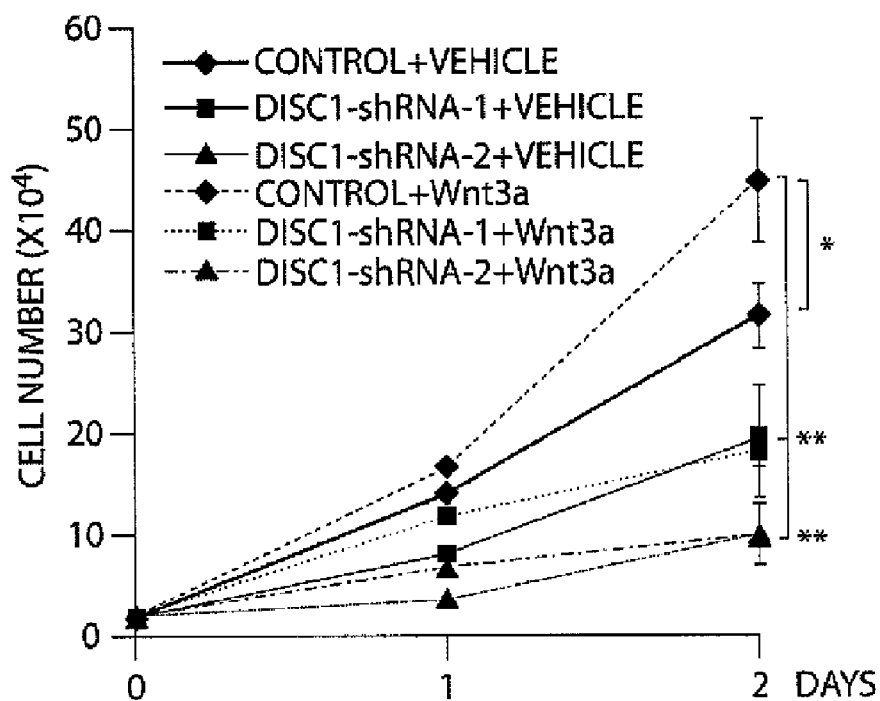
FIG. 3 indicates that DISC1 regulates the β-catenin pathway. a. DISC1 knockdown cells exhibit proliferation defects in response to Wnt3a. Transduced AHPs were grown in medium with or without Wnt3a (200 ng/ml) and cell numbers were counted for 2 days (n=3, *p<0.05, **p<0.01). b. TOPFLASH activity is decreased in DISC1-silenced primary neural progenitors. FOPFLASH activity is not affected by DISC1 shRNAs. The relative firefly luciferase activity normalized to renilla luciferase activity is shown (n=6, p<0.01). c. TOPFLASH activity is rescued by human WT-DISC1 expression in DISC1-silenced primary neural progenitors (n=3, p<0.01). d. In utero TCF luciferase assay in DISC1 knockdown brains. Control or DISC1 shRNAs were coelectroporated with 8× SuperTOPFLASH and pRL-TK plasmids into E13 brains. Embryonic brains were harvested and subjected to luciferase assays 48 hours later. The relative TCF luciferase activity normalized to renilla luciferase activity is shown (p<0.001). e. Proliferation is stimulated in DISC1 overexpressing AHPs in response to Wnt3a (n=3, p<0.01). f. TOPFLASH activity is increased in primary neural progenitors overexpressing DISC1. Shown is the relative firefly luciferase activity normalized to renilla luciferase activity (n=3, p<0.01). g. In utero TCF luciferase activity is increased with DISC1 overexpression. Luciferase activity is measured 24 hours after in utero electroporation (p<0.001).
Figure 3B:
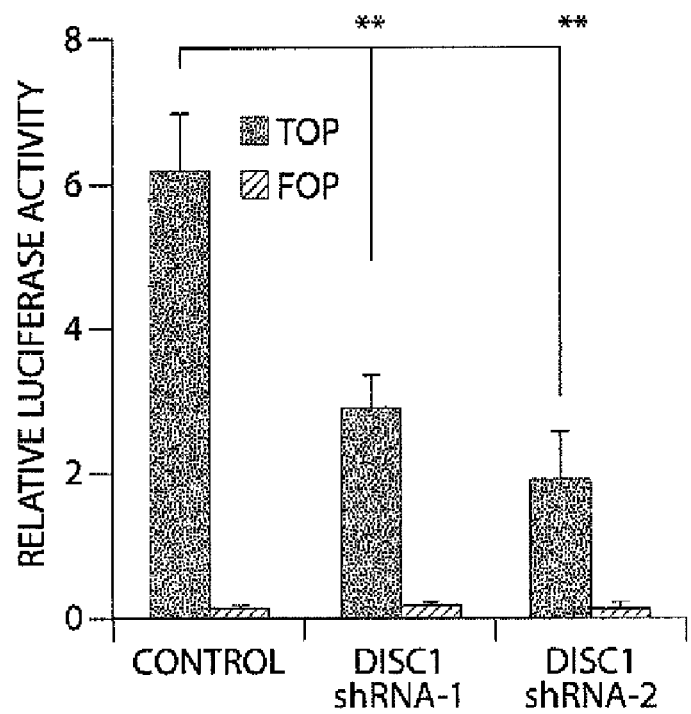
Figure 3C:
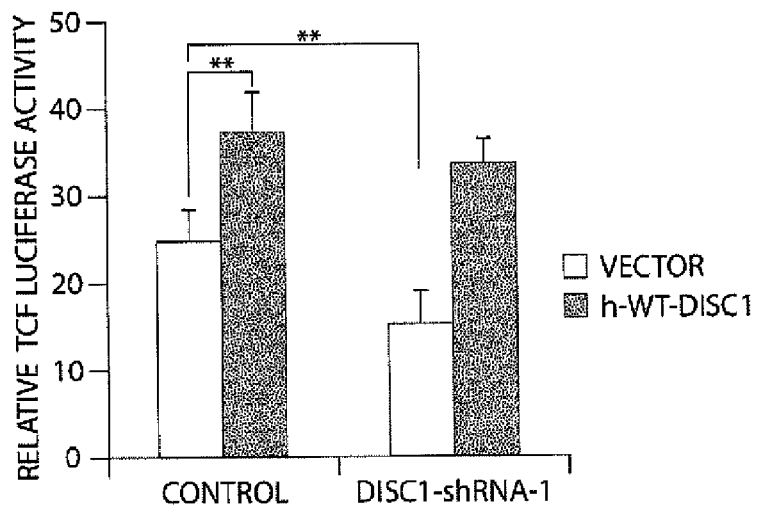
Figure 3D:
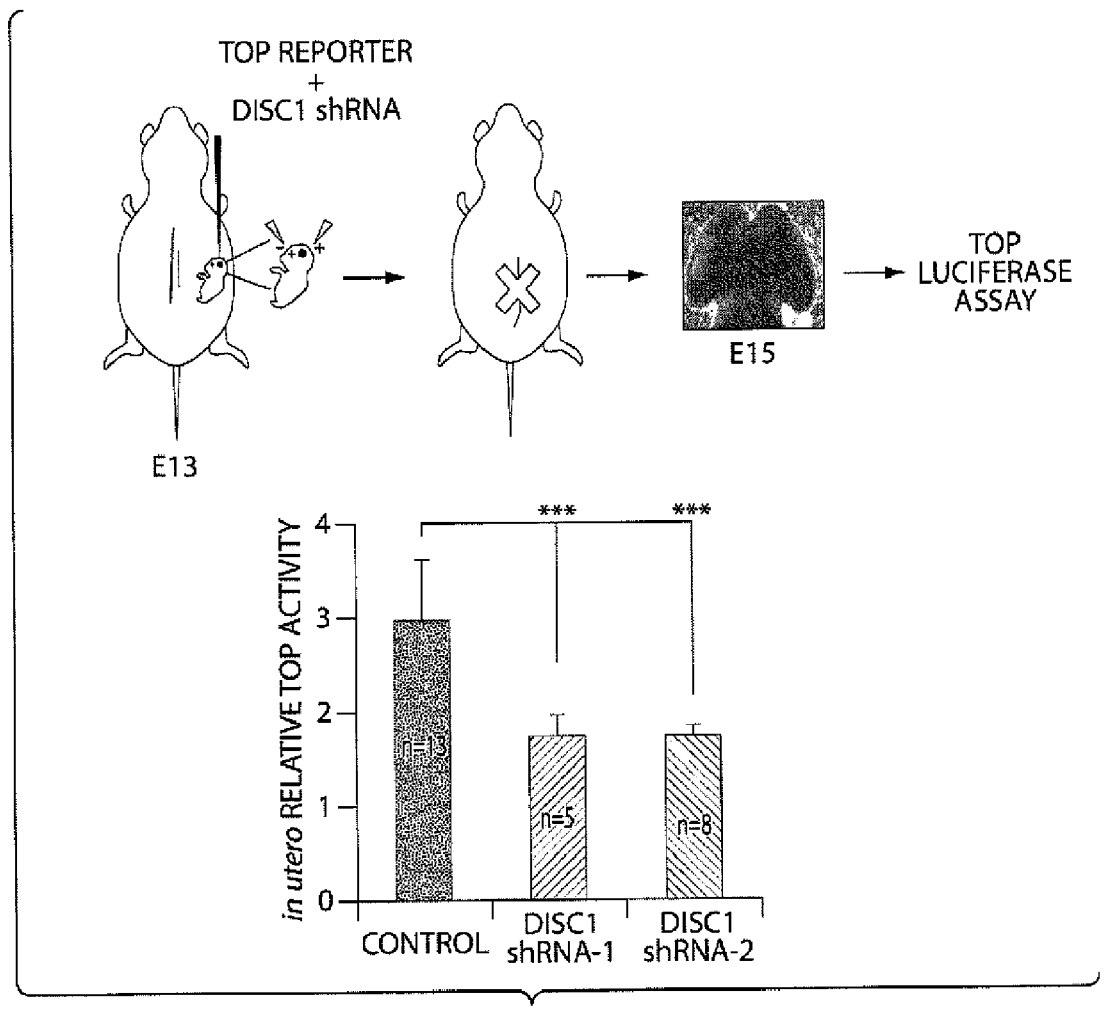
Figure 9A:
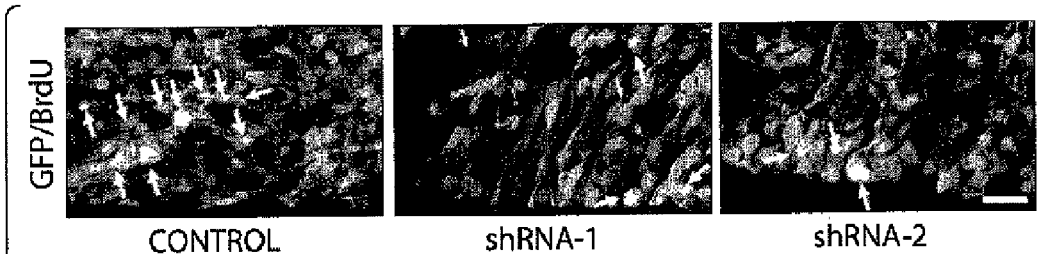
Figure 9A:
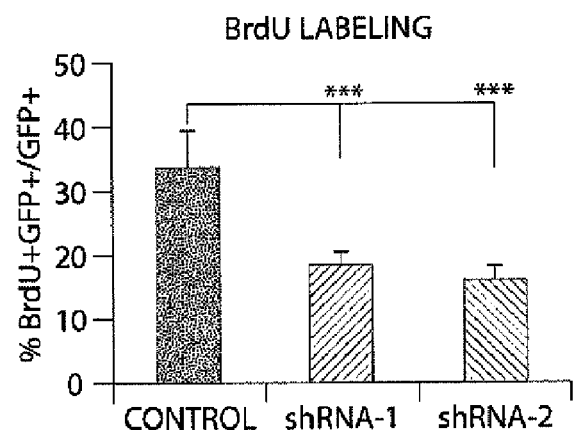
Figure 9B:
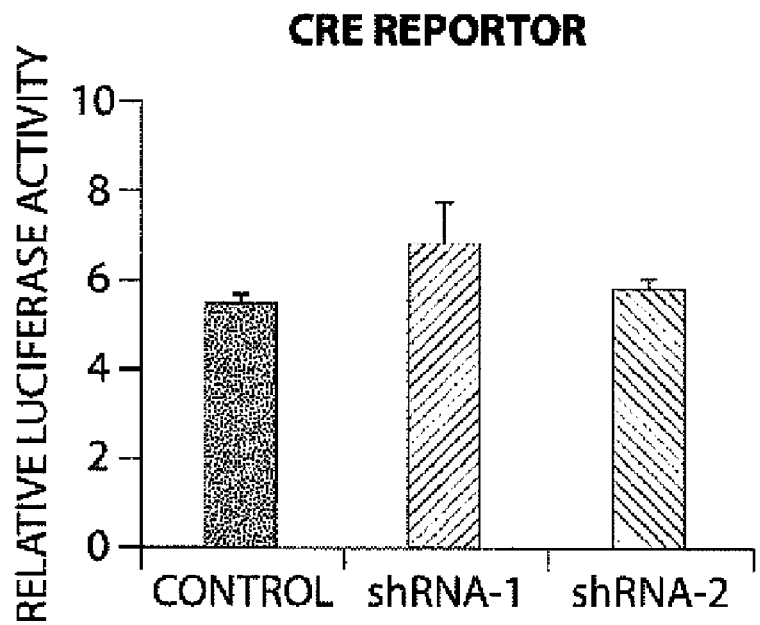
Figure 9C:
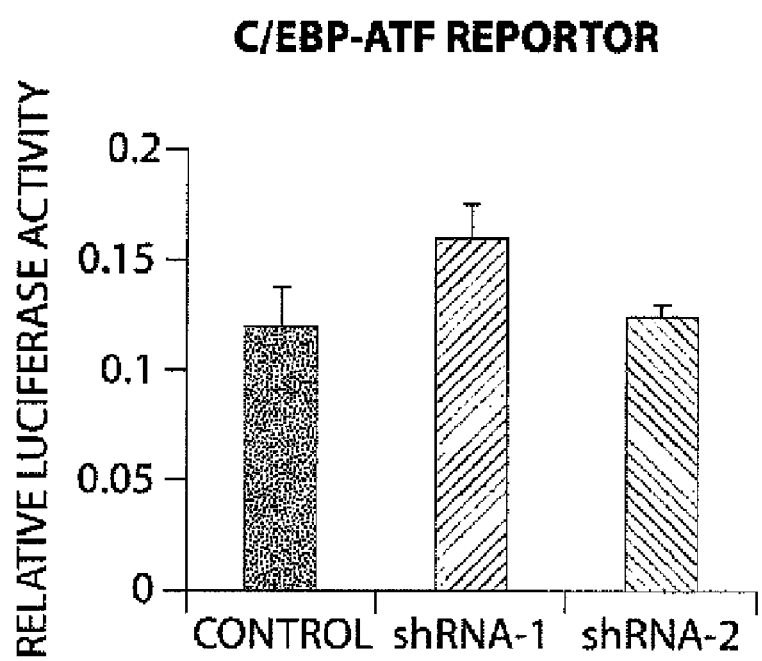

DISC1 and Wnt Signaling

β-catenin signaling is a conserved pathway implicated in maintenance of the stem cell pool (Lie, D. C. et al. Wnt signaling regulates adult hippocampal neurogenesis. Nature 437, 1370-5 (2005); Zechner, D. et al. beta-Catenin signals regulate cell growth and the balance between progenitor cell expansion and differentiation in the nervous system. Dev Biol 258, 406-18 (2003); Lei, Q. et al. Wnt signaling inhibitors regulate the transcriptional response to morphogenetic Shh-Gli signaling in the neural tube. Dev Cell 11, 325-37 (2006)), neuronal differentiation (Hirabayashi, Y. et al. The Wntibeta-catenin pathway directs neuronal differentiation of cortical neural precursor cells. Development 131, 2791-801 (2004)), and development of the central nervous system (Schuller, U. & Rowitch, D. H. Beta-catenin function is required for cerebellar morphogenesis. Brain Res 1140, 161-9 (2007)). Both DISC1 and β-catenin (Hirabayashi, Y. et al. The Wnt/beta-catenin pathway directs neuronal differentiation of cortical neural precursor cells. Development 131, 2791-801 (2004)) are highly enriched in neural progenitors in the VZ. Previous reports demonstrated that ablation of β-catenin expression in the developing brain resulted in the depletion of nestin positive neural progenitors, whereas transgenic mice expressing stabilized β-catenin exhibited a drastically expanded progenitor pool in embryonic brains (Zechner, D. et al. beta-Catenin signals regulate cell growth and the balance between progenitor cell expansion and differentiation in the nervous system. Dev Biol 258, 406-18 (2003); Chenn, A. & Walsh, C. A. Regulation of cerebral cortical size by control of cell cycle exit in neural precursors. Science 297, 365-9 (2002)). Thus, β-catenin and DISC1 share similar properties in regulating neural progenitors. Since β-catenin is a central downstream effector of canonical Wnt signaling, we investigated the possibility that DISC1 may also modulate Wnt-mediated proliferation. The addition of Wnt3a (200 ng/ml) significantly stimulated proliferation of AHPs (FIG. 3a), a result consistent with the observation that expression of β-catenin promotes proliferation of neural stem cells in the presence of bFGF (Israsena, N., Hu, M., Fu, W., Kan, L. & Kessler, J. A. The presence of FGF2 signaling determines whether beta-catenin exerts effects on proliferation or neuronal differentiation of neural stem cells. Dev Biol 268, 220-31 (2004)). Strikingly, the Wnt3a-dependent increase in proliferation was abolished by DISC1 knockdown (FIG. 3a). These data imply that DISC1 function converges with downstream mediators of Wnt-dependent proliferation.

β-catenin exerts its function in part through nuclear translocation to stimulate transcription of genes containing binding sites for the lymphoid enhancer factor-T cell factor (LEF/TCF) family (Gregorieff, A. & Clevers, H. Wnt signaling in the intestinal epithelium: from endoderm to cancer. Genes Dev 19, 877-90 (2005)). The transcription complex containing nuclear β-catenin activates the expression of target genes such as cyclin D1 (Tetsu, O. & McCormick, F. Beta-catenin regulates expression of cyclin D1 in colon carcinoma cells. Nature 398, 422-6 (1999)) and c-myc (He, T. C. et al. Identification of c-MYC as a target of the APC pathway. Science 281, 1509-12 (1998)), and stimulates cell proliferation (Adachi, K. et al. Beta-catenin signaling promotes proliferation of progenitor cells in the adult mouse subventricular zone. Stem Cells 25, 2827-36 (2007)). Since DISC1 knockdown abrogated Wnt-dependent proliferation, we determined whether DISC1 is required for LEF/TCF activation using a luciferase reporter construct containing 8 copies of the LEF/TCF binding site (8×SuperTOPFLASH) or mutated LEF/TCF binding sites (8×SuperFOPFLASH) (Veeman, M. T., Slusarski, D.C., Kaykas, A., Louie, S. H. & Moon, R. T. Zebrafish prickle, a modulator of noncanonical Wnt/Fz signaling, regulates gastrulation movements. Curr Biol 13, 680-5 (2003)). Neural progenitor cultures were infected with lentivirus expressing control or DISC1 shRNAs. Three days later, the cultures were transfected with the 8×SuperTOPFLASH or 8×SuperFOPFLASH reporter 24 hours prior to analysis. LEF/TCF reporter activity was significantly reduced by DISC1 knockdown in cultures treated with Wnt3a (FIG. 3b), and this effect was specific to the LEF/TCF binding sites because DISC1 shRNAs did not affect FOPFLASH reporter activity. As a key control, we showed that the reduction in LEF/TCF reporter activity caused by DISC1 knockdown could be rescued by co-expressing human DISC1 cDNA with DISC1 shRNA-1 (FIG. 3c). The reduction in LEF/TCF activity by DISC1 knockdown could also be recapitulated in the developing brain by co-electroporating control or DISC1 shRNA with the LEF/TCF reporter (FIG. 3d). To exclude off-target effects of DISC1 shRNAs on general luciferase activity, we tested whether DISC1 knockdown also affected the irrelevant CRE and C/EBP-ATF reporters (FIGS. 9b, c). Neither DISC1 shRNAs altered CRE or C/EBP-ATF reporter activity, supporting the specificity of DISC1-mediated repression of LEF/TCF transcriptional activity. Thus, these data imply that DISC1 regulates LEF/TCF transcriptional activity, a common readout of canonical Wnt signaling.

Figure 3E:
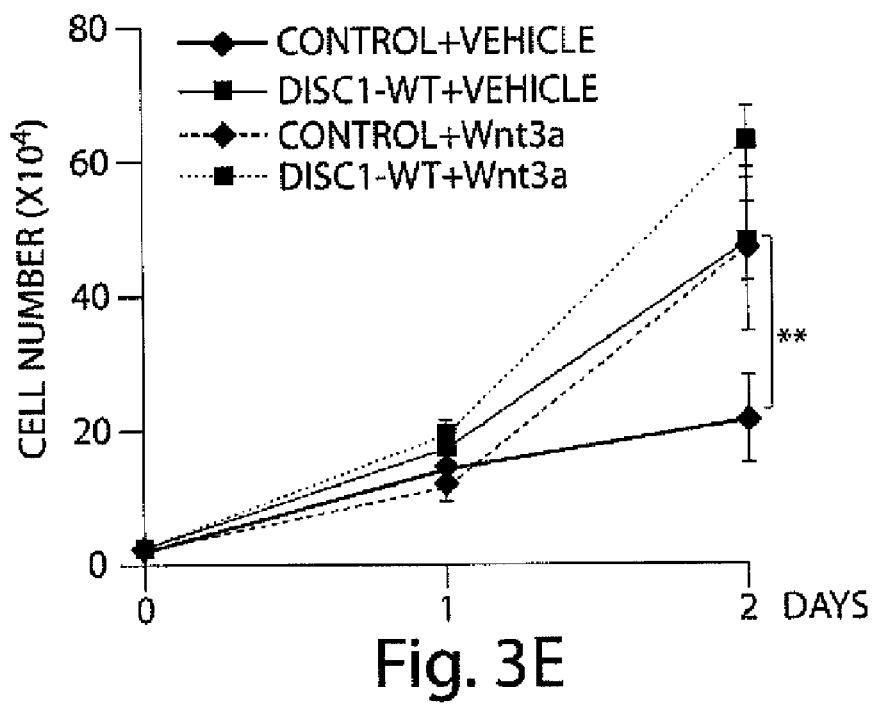
Figure 3F:
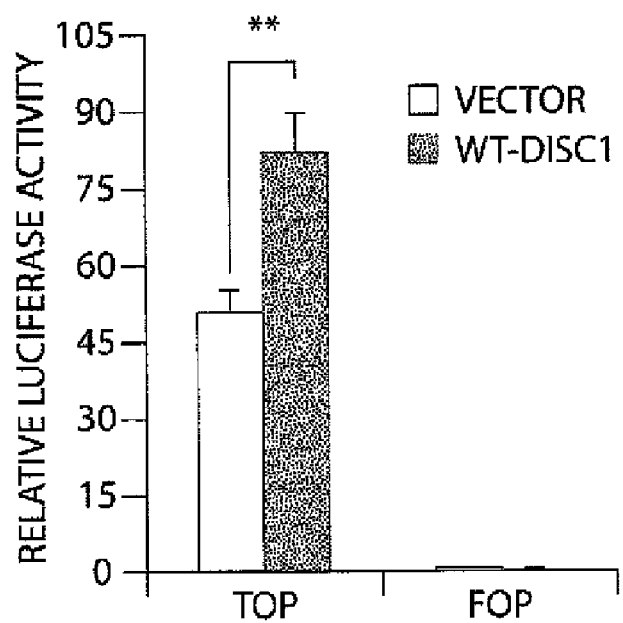
Figure 3G:
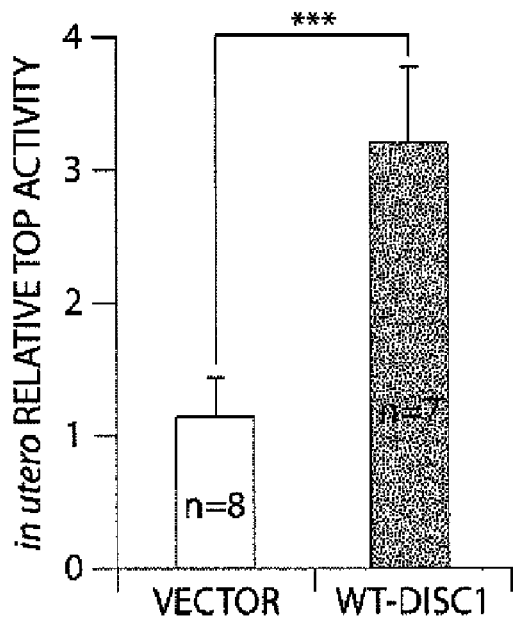

If DISC1 loss-of-function attenuates Wnt signaling, then DISC1 gain-of-function should potentiate this signaling pathway. Consistent with this, we found that DISC1 overexpression in AHP cells potentiated proliferation to a similar extent as was observed with Wnt3a addition (FIG. 3e). Interestingly, Wnt3a had a modest effect on DISC1 overexpressing cells compared to cells expressing the control construct. These data confirm that DISC1 functions as a positive regulator of proliferation. Finally, DISC1 overexpression increased TOP-FLASH, but not FOPFLASH, reporter activity in primary neural progenitor cultures (FIG. 3f) and in embryonic brains by more than 2 fold (FIG. 3g). Together, these results indicate that DISC1 participates in the Wnt signaling pathway and in Wnt-mediated cell proliferation.

Figure 4A:
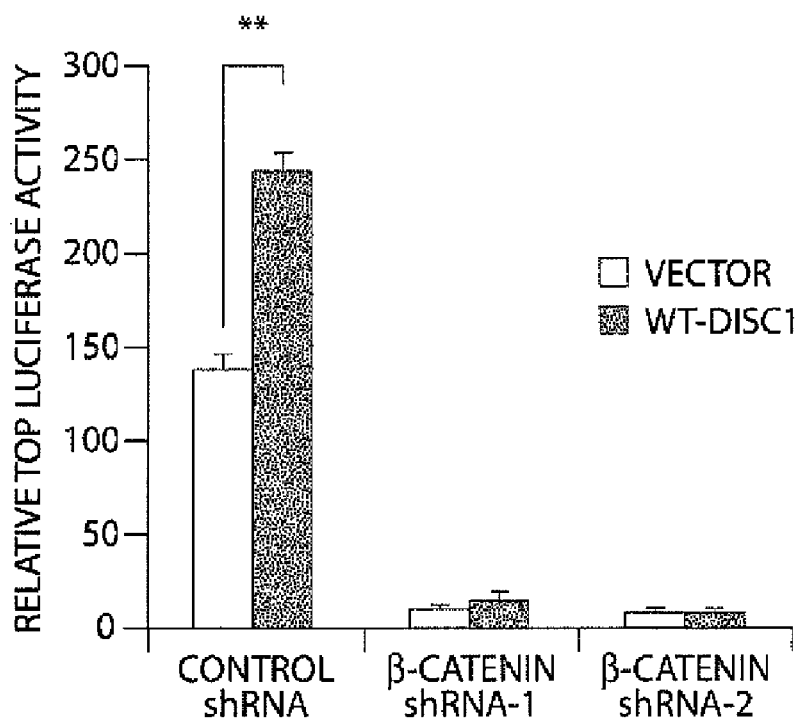
FIG. 4 indicates that DISC1 regulates the GSK3β signaling pathway. a. Enhancement of TOPFLASH activity by DISC1 overexpression is abolished by β-catenin shRNAs in embryonic primary progenitors (n=6, p<0.01). b. Vector, Dvl2, WT-β-catenin or SA-β-catenin was cotransfected with the TOP reporter into embryonic progenitors transduced with lentiviruses expressing DISC1 shRNAs. Only SA-β-catenin rescued the TCF activation defect in DISC1 knockdown cells (n=4, *p<0.05, p<0.01). c. Phosphorylation of β-catenin is increased in DISC1 silenced AHPs. Numbers in the panel indicate the relative intensity of the band compared to control (n=3). d. GSK3β activity increases in DISC1 knockdown cells. Lysates from transduced AHPs were immunoblotted with the anti-pY216-GSK3β antibody. Numbers in the panel indicate the relative intensity of the band compared to control (n=3). e. DISC1 interacts with endogenous GSK3β. E14 brain lysate was subjected to immunoprecipitation with anti-HA (negative control) or anti-DISC1 antibody and immunoblotted with anti-GSK3β or DISC1 antibody. f. GSK3β directly binds to DISC1 in vitro. Purified His-GSK3β interacts directly with DISC1 fragments 1-220aa and 356-595aa. Stars indicate the intact GST fusion proteins. g. GSK3β activity is reduced by DISC1 fragments in vitro. Numbers in the panel indicate the relative intensity of the band compared to the no protein lane (n=3). Stars indicate the different intact GST fusion proteins. h. Reduction of Y216 phosphorylation on GSK3β by DISC1 fragment 1-220 is dose-dependent. Stars indicate the different intact GST fusion proteins. Numbers in the panel indicate the relative intensity of the band compared to GST (n=3). i. Inhibition of GSK3β activity by DISC1 peptide 1(195-238aa) is dose-dependent. The dose-response curve is shown (n=3, *, p<0.005). j. Overexpression of DISC1 suppresses GSK3β activity. Numbers in the panel indicate the relative intensity of the band compared to control (n=3). k. Phosphorylated β-catenin is reduced by DISC1 overexpression in AHPs. Numbers in the panel indicate the relative intensity of the band compared to vector (n=3).
Figure 4B:
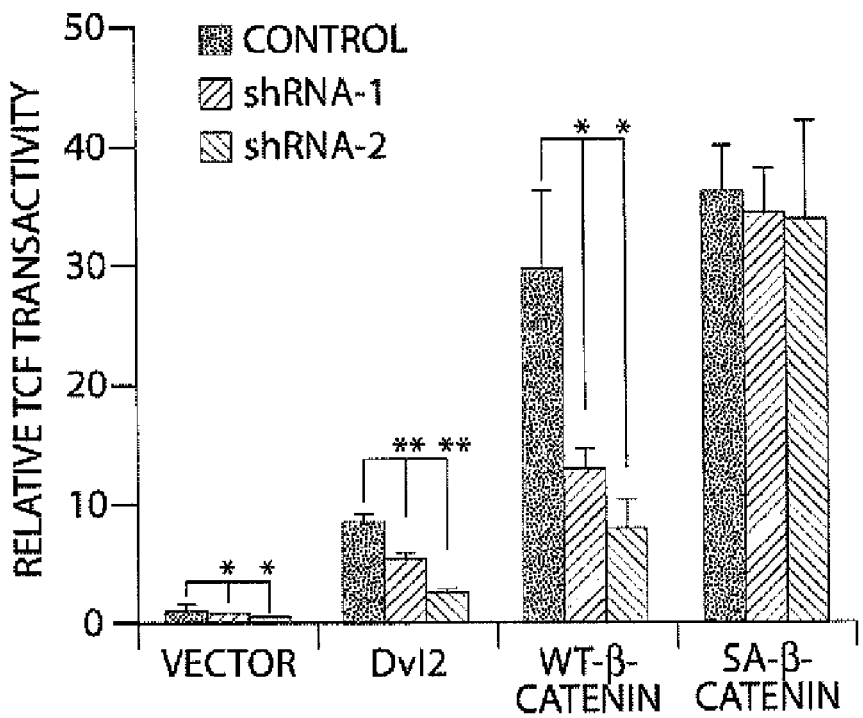
Figure 4C:
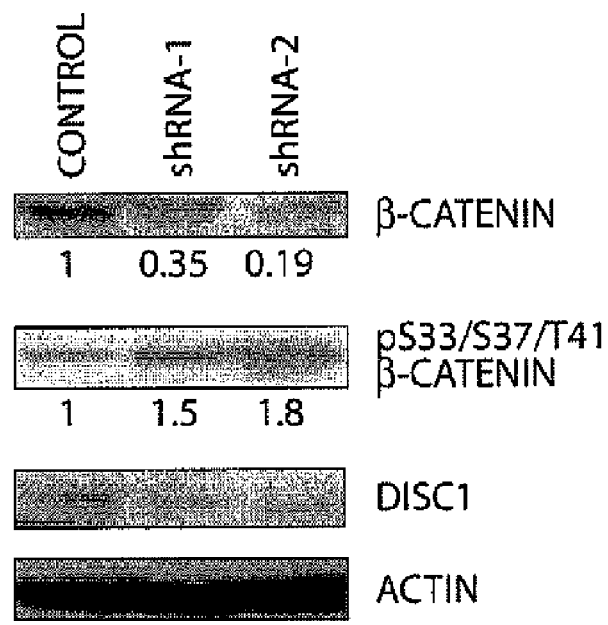

To further decipher the mechanism by which DISC1 influences the Wnt signaling pathway, we created two independent β-catenin shRNAs that efficiently silenced endogenous β-catenin expression (FIG. 10a). We found that the enhancement of LEF/TCF reporter activity by DISC1 overexpression was completely abolished when the expression of endogenous β-catenin was silenced (FIG. 4a), indicating that the effects of DISC1 on LEF/TCF reporter activity require β-catenin. To further determine the epistatic relationship of DISC1 with known components of Wnt signaling, we evaluated the effects of co-expressing Dvl2, wild type-β-catenin, or a degradation-resistant mutant of β-catenin-93A (SA-β-catenin) with control or DISC1 shRNAs on LEF/TCF reporter activity. Expression of Dvl2, WT and mutant β-catenin all potentiated Super(8×)TOPFLASH reporter activity (FIG. 4b). However, while DISC1 knockdown significantly down-regulated the reporter activity in Dvl2 and WT-β-catenin expressing cells, it had no effect on SA-β-catenin-mediated reporter activation (FIG. 4b). This implies that DISC1 either acts at or downstream of Dvl2 and upstream of β-catenin, and may regulate the abundance of β-catenin. Indeed, we found that DISC1 shRNA-1 and -2 significantly decreased β-catenin levels (35% and 19% to control, respectively) in AHPs (FIG. 4c). It is well established that GSK3β regulates β-catenin stability by phosphorylating serine and threonine residues that target β-catenin for ubiquitin-dependent degradation (Aberle, H., Bauer, A., Stappert, J., Kispert, A. & Kemler, R. beta-catenin is a target for the ubiquitin-proteasome pathway. Embo J 16, 3797-804 (1997); Winston, J. T. et al. The SCFbeta-TRCP-ubiquitin ligase complex associates specifically with phosphorylated destruction motifs in Ikappa-Balpha and beta-catenin and stimulates Ikappa-Balpha ubiquitination in vitro. Genes Dev 13, 270-83 (1999)). Notably, we observed that the reduction in β-catenin levels caused by DISC1 knockdown was accompanied by increases in Ser33/37, Thr41 phosphorylation, sites phosphorylated by GSK3β (FIG. 4c), and increases in ubiquitination (FIG. 10b). Thus, DISC1 loss-of-function upregulates phosphorylation of β-catenin by GSK3β and subsequently reduces β-catenin abundance.

Example 5

DISC1 and GSK3β Activity

Figure 4D:
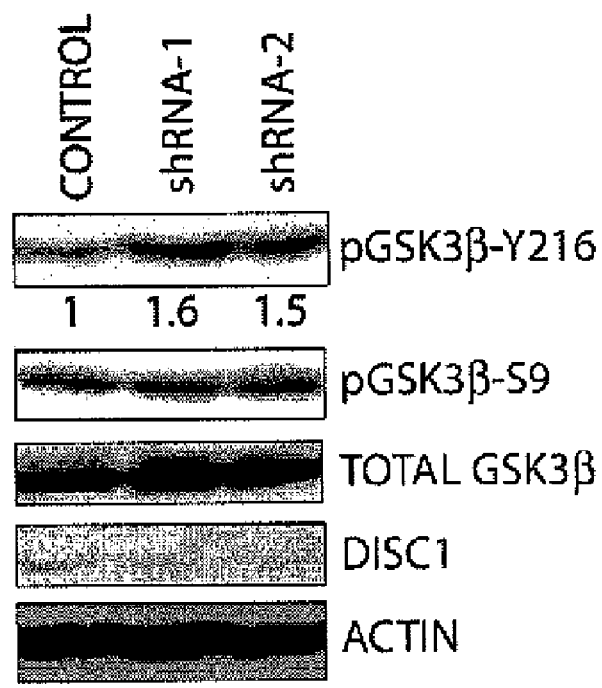
Figure 4E:
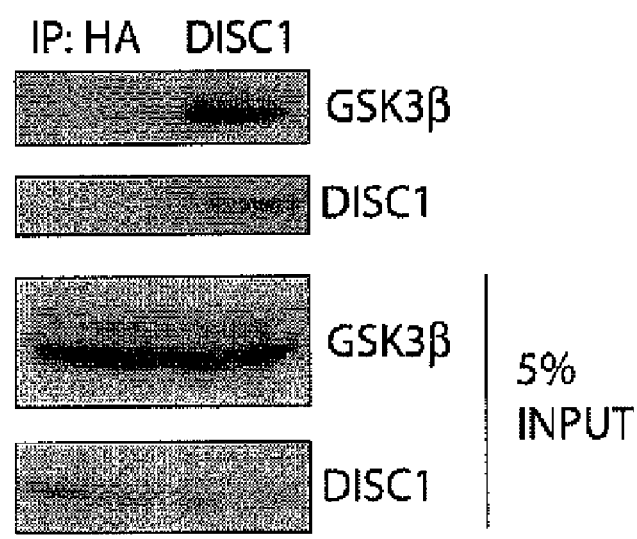
Figure 4F:
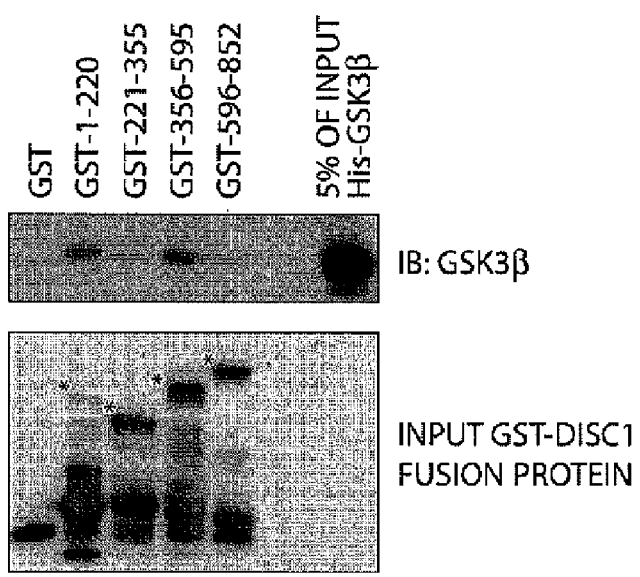

The increased serine and threonine phosphorylation of β-catenin caused by DISC1 knockdown raised the possibility that GSK3β activity is directly or indirectly influenced by DISC1. Growth factors such as insulin activate AKT, which in turn phosphorylates GSK3β at Ser9, an inhibitory phosphorylation site (Cross, D. A., Alessi, D. R., Cohen, P., Andjelkovich, M. & Hemmings, B. A. Inhibition of glycogen synthase kinase-3 by insulin mediated by protein kinase B. Nature 378, 785-9 (1995)). Furthermore, GSK3β autophosphorylates itself at Tyr216 (Kim, L., Harwood, A. & Kimmel, A. R. Receptor-dependent and tyrosine phosphatase-mediated inhibition of GSK3 regulates cell fate choice. Dev Cell 3, 523-32 (2002); Lochhead, P. A. et al. A chaperone-dependent GSK3beta transitional intermediate mediates activation-loop autophosphorylation. Mol Cell 24, 627-33 (2006)), which is required for its activity. Upon transfection of AHPs with DISC1 shRNAs, we observed a significant increase in Y216 phosphorylation, implying that DISC1 negatively impacts GSK3β activity (FIG. 4d). In contrast, Ser9 phosphorylation was not affected by DISC1 knockdown (FIG. 4d), implying that DISC1 specifically inhibits GSK3β activity by preventing its autophosphorylation. Notably, phosphorylation of other known GSK3β substrates, Ngn2 (Ma et al., 2008) and C/EBPα (Ross et al., 1999) was not affected by DISC1 shRNAs or overexpression. Consistent with its ability to regulate GSK3β activation, co-immunoprecipitation (IP) experiments revealed that DISC1 associates with GSK3β in E15 mouse embryonic brains (FIG. 4e). To determine whether DISC1 and GSK3β directly bind each other and to map the region(s) of DISC1 required for the interaction, we generated four GST-tagged DISC1 protein fragments (1-220aa, 221-355aa, 356-595aa, and 596-852aa) and performed an in vitro association assay with purified His-tagged GSK3β (FIG. 4f). We adjusted the amounts of intact fragments (indicated by stars) used in the reactions due to significant degradation of the GST-DISC1 fusion proteins, especially for fragment 1-220. DISC1 fragments spanning residues 1-220 and 356-595 exhibited strong interactions with GSK3β, whereas the other two fragments showed negligible interaction. Collectively, these results indicate that DISC1 directly interacts with and negatively regulates GSK3β activity.

To determine whether DISC1 inhibits GSK3β through direct association, we have taken efforts to optimize the GSK3β kinase assay using β-catenin as a substrate. At molar ratios (β-catenin:GSK3β) of 0.5 and 1, the phosphorylation of β-catenin reached saturation after 15 minutes. Based on this, we performed kinase assays at a ratio 2 (0.14 μM:0.07 μM). Second, the length of reaction was varied from 10 to 30 minutes. At a ratio of 2, phosphorylation of β-catenin reached saturation at 30 minutes. Therefore, we performed kinase assays in the linear range with a ratio of 2 and a duration of 15 minutes (data not shown).

Figure 4G:
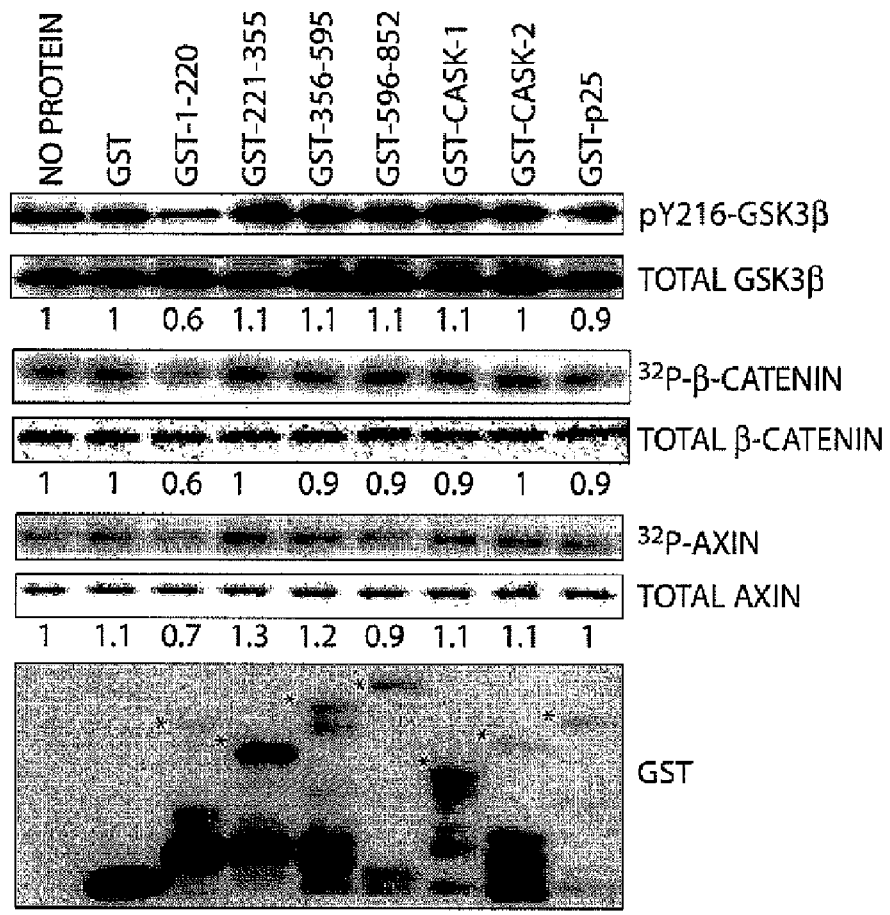
Figure 4H:
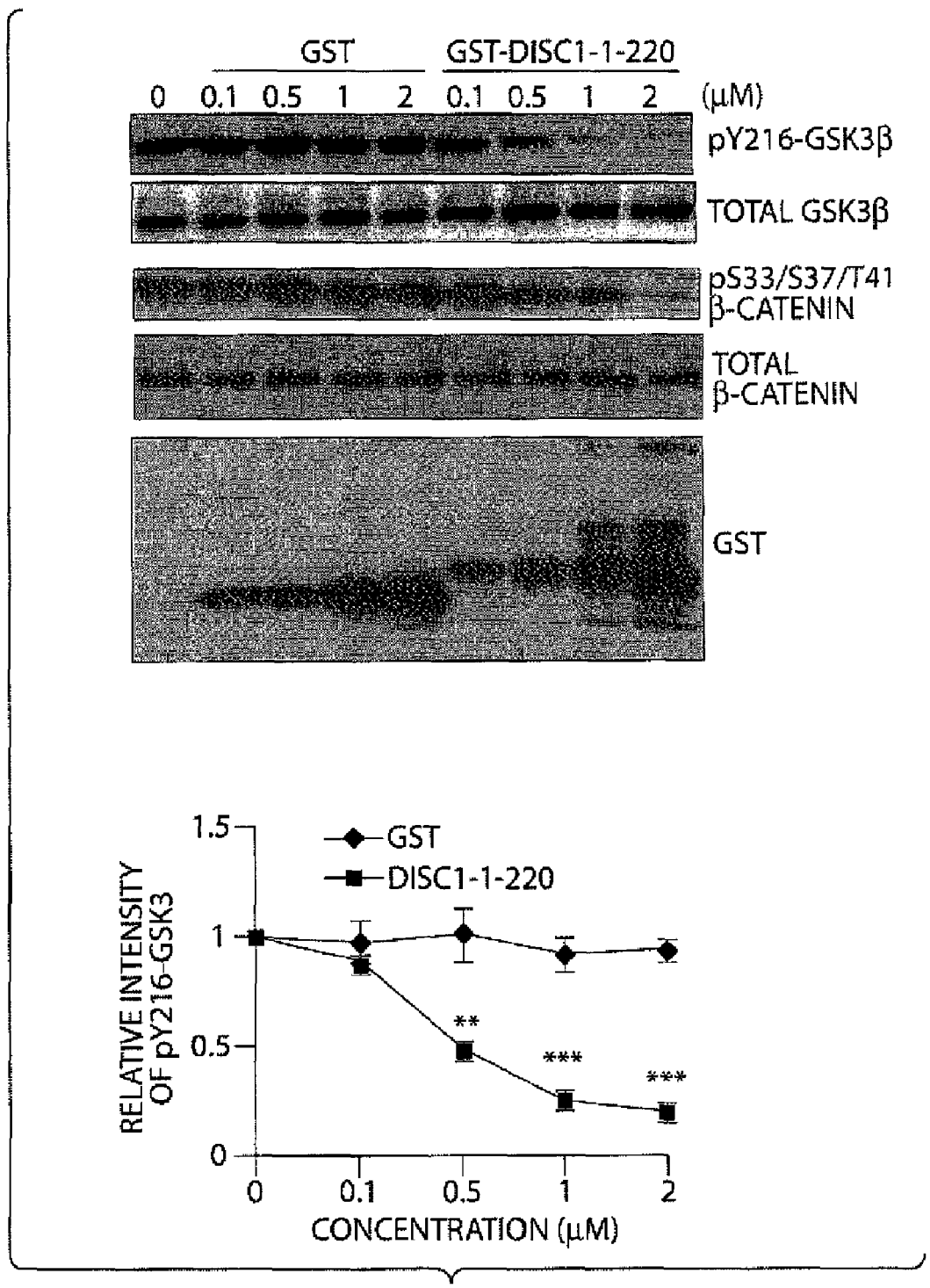
Figure 4I:
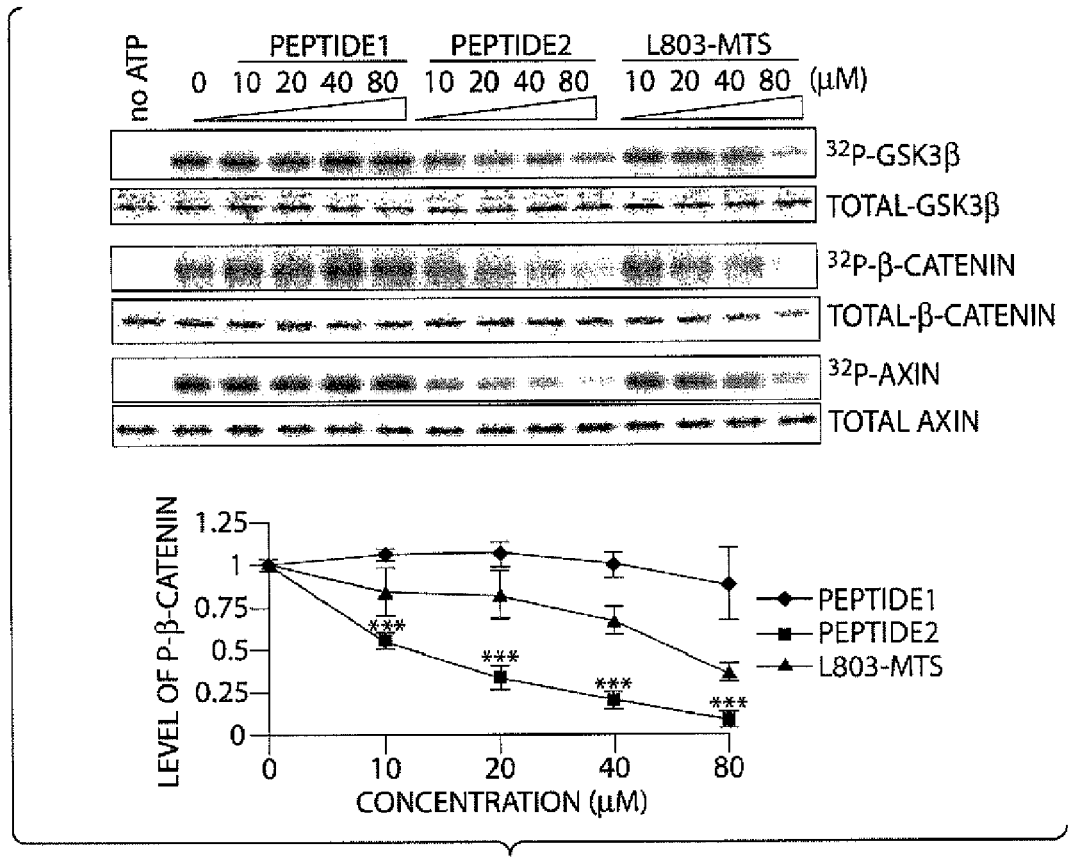

To examine the effect of DISC1 fragments on GSK3β activity, 0.5 μM of the GST-DISC1 fragments, GST-CASK fragments, or GST-p25 were incubated with purified active GSK3β in the presence of the GSK3β substrates β-catenin and axin (Thomas, G. M. et al. A GSK3-binding peptide from FRAT1 selectively inhibits the GSK3-catalysed phosphorylation of axin and beta-catenin. FEBS Lett 458, 247-51 (1999)) in vitro. We then analyzed the extent of GST-β-catenin phosphorylation, GST-axin phosphorylation, and GSK3β autophosphorylation at Y216. Consistent with its ability to bind GSK3β, the DISC1 fragment spanning residues 1-220 potently inhibited β-catenin, axin and GSK3β phosphorylation at 0.5 μM, whereas none of the other 3 DISC1 fragments, GST-p25, or GST-CASK proteins inhibited GSK3β activity at this concentration (FIG. 4g). However, at higher concentrations (2 μM), DISC1 fragments spanning 221-355 and 356-595 started to inhibit GSK3β autophosphorylation (FIG. 10c). This implies that the inhibitory activity of DISC1 on GSK3β may reside on multiple domains, but that fragment 1 (1-220) possesses the most potent inhibitory activity on GSK3β. Furthermore, a dose response curve was established for DISC1 1-220 whereby no inhibition of GSK3β Y216 phosphorylation was observed at 0.1 μM and the inhibition of phosphorylation plateaued at 1 μM (FIG. 4h). None of the GST-DISC1 fragments inhibited AKT autophosphorylation (data not shown) indicating that DISC1 is not a general kinase inhibitor. To narrow down the inhibitory domain of DISC1 to GSK3β, we synthesized two peptides from mouse DISC1 which are highly conserved between human and mouse (FIG. 11). Peptide 1 spanned amino acids 40-78 and peptide 2 spanned amino acids 195 to 238. In vitro kinase assays demonstrated that peptide 1 did not inhibit GSK3β at 80 μM, whereas peptide 2 inhibited GSK3β at 10 μM, and inhibited GSK3β more potently than the commercial GSK3β peptide inhibitor, L803-MTS (FIG. 4i).

Surface plasmon resonance (SPR) was used to determine whether peptide 2 directly binds to GSK3β. GSK3β SPR binding assays were carried out with peptide 1, peptide 2, the GSK3β inhibitor L803-MTS, and as a negative control, a peptide from the N-type calcium channel, CACNA1B (FIG. 6A). We found that both peptide 2 and L803-MTS bound to GSK3β (percent theoretical maximal response 197% and 259% respectively) at a concentration of 25 μM (FIG. 6A), while both peptide 1 and the calcium channel peptide showed much lower binding (percent theoretical maximal response 62% and 29% respectively). Interestingly, the super-stoichiometric binding exhibited by both L803-MTS and peptide 2 (197% and 259% respectively) suggests that both bound to GSK3β in these assays at a peptide-protein ratio of 2:1. To identify the peptide 2 sequences that mediate this interaction with GSK3β, we designed overlapping 15-mer peptides that covered peptide 2 and tested their binding to GSK3β SPR (FIG. 16B). One 15-mer peptide that encompasses mDISC1 amino acids 211 to 225, number 43 (peptide 3, also referred to as DISCtide2), bound to GSK3β, while other peptide 2 15-mers showed background levels of binding (FIG. 16B). Similar to peptide 2, peptide 3 showed super stoichiometric binding to GSK3β in these assays with a peptide-protein ratio of 2:1 (percent maximal binding 238%). Further characterization of peptide 3 is shown in FIG. 18. Importantly, a reversed peptide 3 sequence displayed a negligible binding to GSK3β, demonstrating that the binding of peptide 3 to GSK3β is specific. Despite this specific binding to GSK3β, peptide 3 failed to inhibit GSK3β kinase activity, suggesting that other regions of peptide 2 are also important for the inhibition.

Figures 4J, 4K:
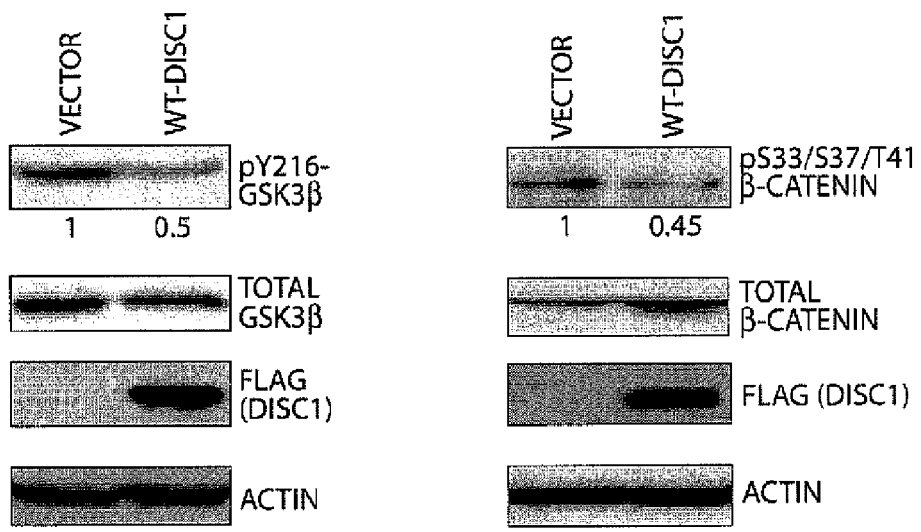

We further evaluated the effect of DISC1 gain-of-function on GSK3β activity and β-catenin levels. Overexpression of WT-DISC1 reduced Y216 phosphorylation (FIG. 4j), decreased total β-catenin 93/37/T41 phosphorylation, and increased total β-catenin levels in progenitors (FIG. 4k). Collectively, these results indicate that DISC1 inhibits GSK3β catalytic activity through direct interaction.

If DISC1 is crucial for stabilizing β-catenin, one might predict that β-catenin transcriptional targets is elevated by DISC1 gain-of-function. Cyclin D1 (Tetsu, O. & McCormick, F. Beta-catenin regulates expression of cyclin D1 in colon carcinoma cells. Nature 398, 422-6 (1999)) and axin2 (Leung, J. Y. et al. Activation of AXIN2 expression by beta-catenin-T cell factor. A feedback repressor pathway regulating Wnt signaling. J Biol Chem 277, 21657-65 (2002)) are well-established target of β-catenin, and cyclin D1 functions to promote G1 progression during the cell cycle (Quelle, D. E. et al. Overexpression of mouse D-type cyclins accelerates G1 phase in rodent fibroblasts. Genes Dev 7, 1559-71 (1993)). We found that in AHPs, Cyclin D1 levels were reduced by 50% in DISC1 shRNA-1 expressing cells and by 70% in shRNA-2 expressing cells (FIG. 10d). A similar decrease was also observed with Axin2 expression. Expression of Dvl2, which is not a β-catenin target, did not change. Consistent with the higher proliferative potential of WT-DISC1 overexpressing cells, β-catenin ubiquitination was reduced (FIG. 10e), and cyclin D1 or axin2 expression was markedly upregulated (FIG. 10f, FIG. 3e). These data support the notion that DISC1 controls cell proliferation by modulating GSK3β activity and β-catenin abundance, thereby fine-tuning cell cycle progression.

Figure 12A:
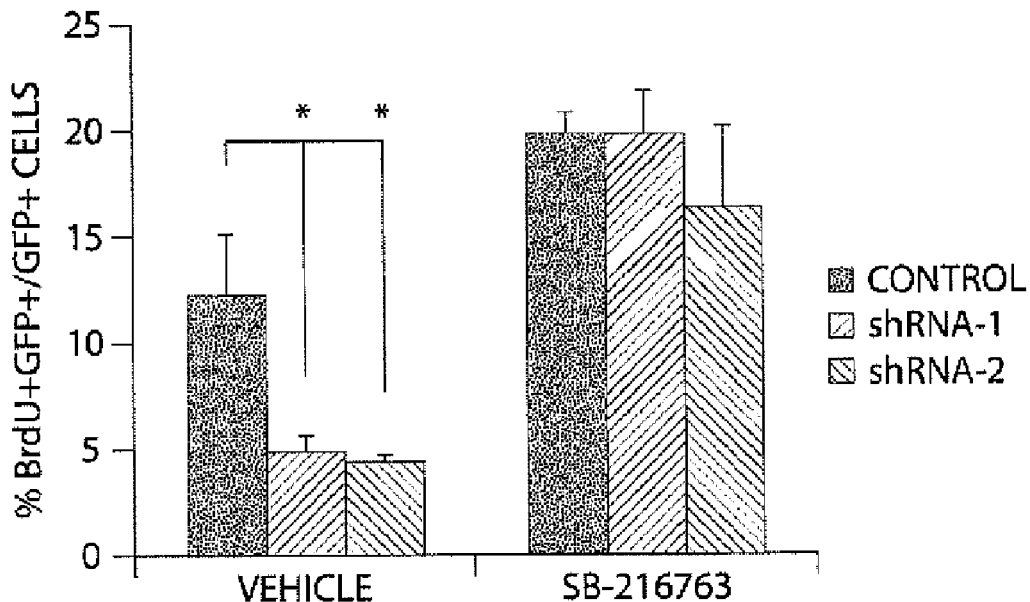
Figure 12B:
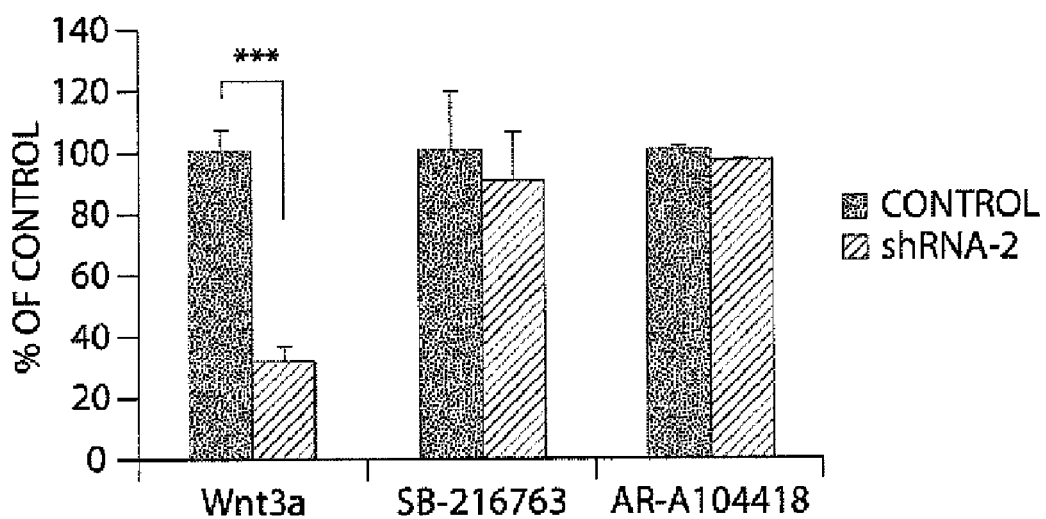

If DISC1 functions to inhibit GSK3β activity, the negative effects of DISC1 silencing on proliferation should be alleviated by GSK3β loss-of-function. We examined the consequence of treating DISC1 knockdown AHP cells with SB-216763, a specific chemical inhibitor of GSK3β. SB-216763 restored the cell proliferation impaired by DISC1 knockdown as evaluated by BrdU incorporation (FIG. 12a). Consistent with this result, the GSK3β inhibitors, SB-216763 and AR-A014418, rescued TCF activity in DISC1 knockdown cells to control levels (FIG. 12b). These experiments further support a role of DISC1 in controlling cell proliferation via modulation of GSK3β.

Example 6

DISC1, WNT Pathway and Brain Development

Figure 5A:
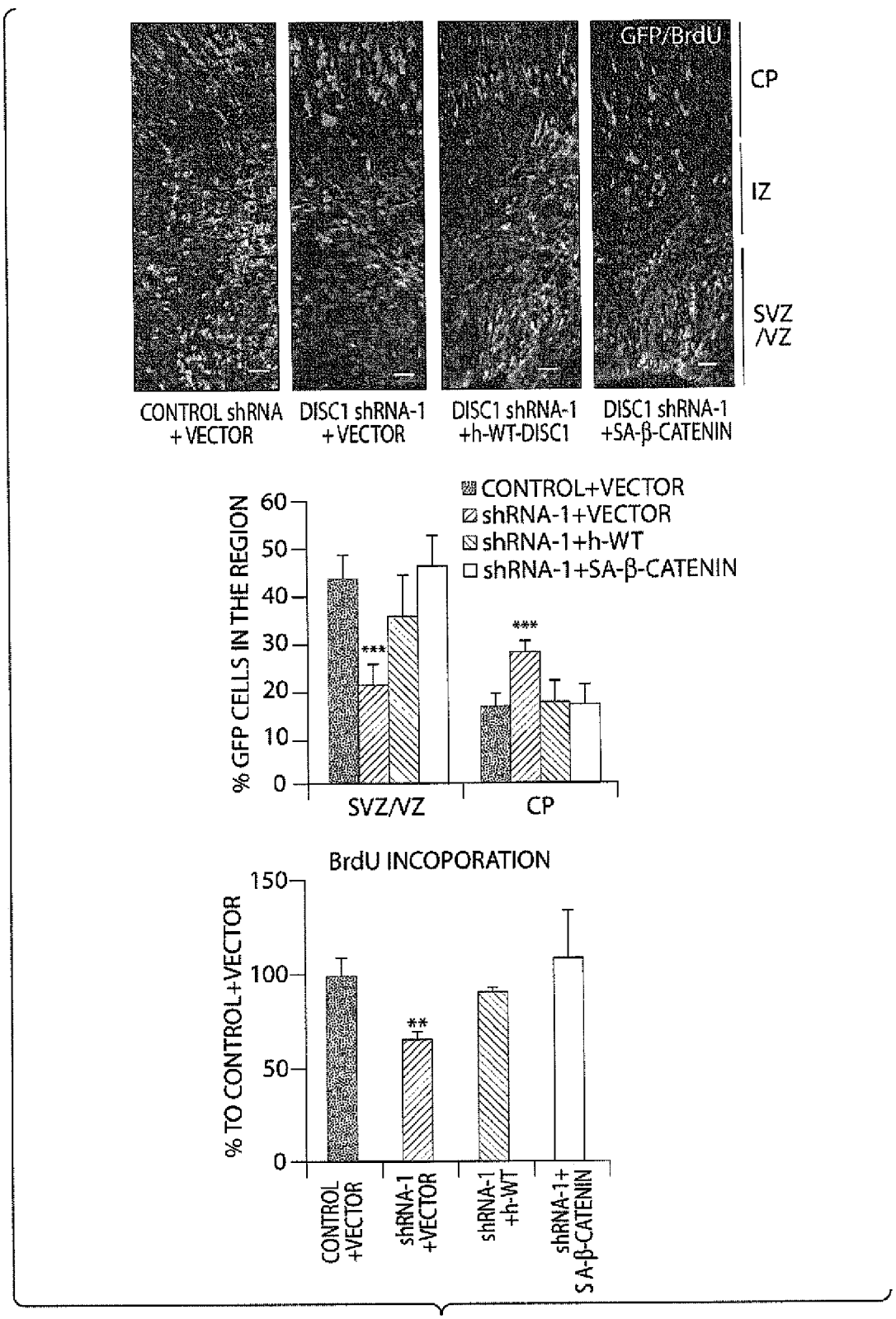
FIG. 5 shows the rescue of the proliferation defect caused by knockdown of DISC1 in vivo. a. Cell positioning and BrdU incorporation defects caused by DISC1 loss-of-function are rescued by human WT-DISC1 or SA-β-catenin. The percentage of GFP positive cells in the SVZ/VZ or CP is shown (n=5, , p<0.01; *, p<0.005). Scale bar=20 µm. b. The reduction in mitotic index caused by DISC1 knockdown in embryonic brains is rescued by human WT-DISC1 or SA-β-catenin. Arrows indicate GFP and pH3 double positive cells. Shown is the percentage of GFP and pH3 double positive cells in total GFP positive cells (n=4, *, p<0.05; ***, p<0.005). Scale bar=20 µm. c. Control or DISC1 shRNA-1 lentivirus was stereotactically injected into adult dentate gyrus. After 4 weeks of recovery, mice received SB216763 (2 mg/kg) every other day for 2 weeks and BrdU (100 mg/kg)
Figure 5B:
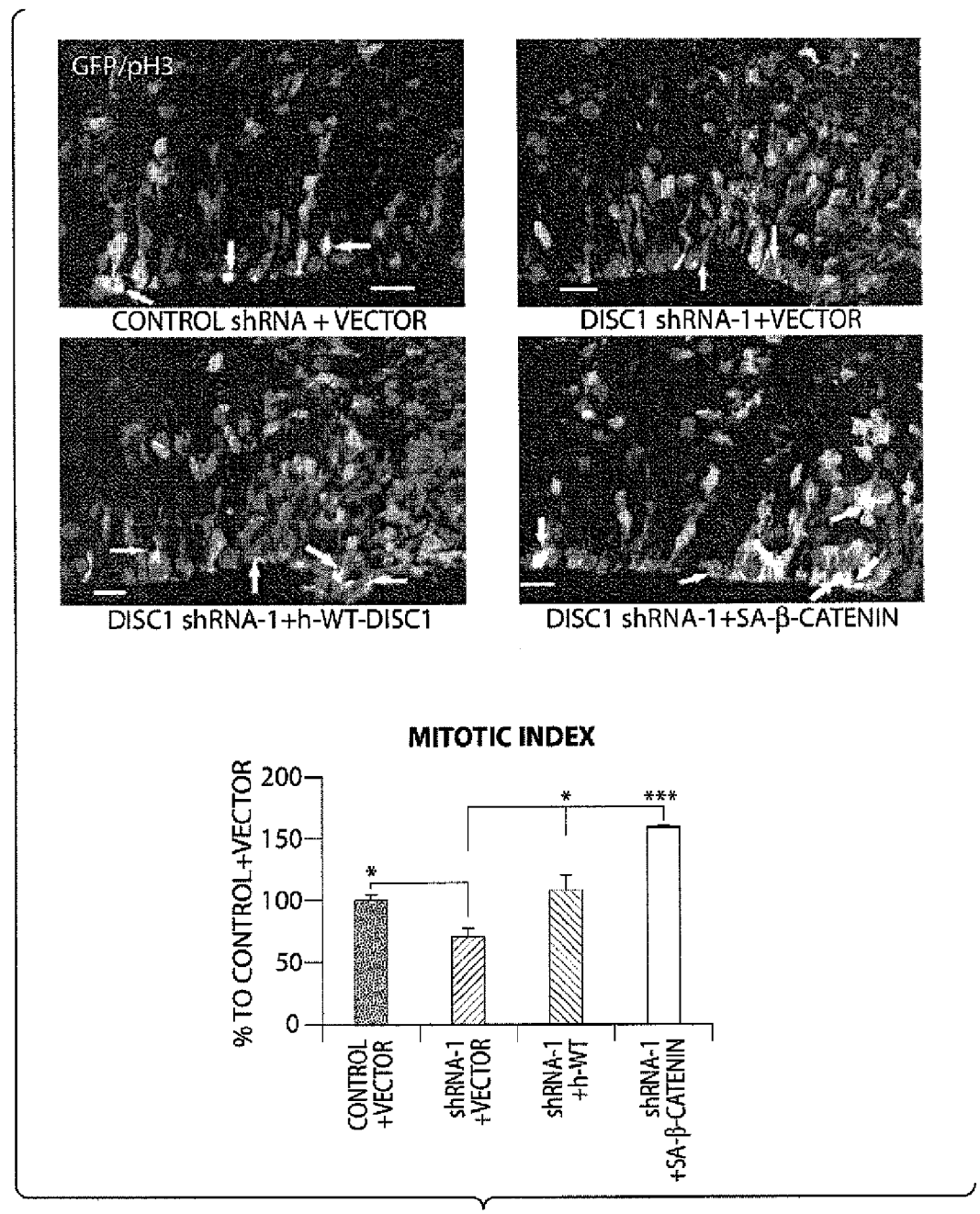

To further examine the relationship between DISC1 and the Wnt pathway in brain development, we determined whether the stable β-catenin mutant SA-β-catenin had an effect on cortical progenitor proliferation in vivo when DISC1 expression was silenced. DISC1 shRNA-1and SA-β-catenin constructs were co-electroporated into E13 mouse brains and the brains harvested 3 days later. As mentioned earlier, DISC1 knockdown reduced the percentage of GFP positive cells in the VZ/SVZ, increased GFP positive cells in the CP, and reduced BrdU labeling and mitotic index (FIG. 2, FIG. 8a). Remarkably, co-expression of SA-β-catenin with DISC1 shRNA-1 completely rescued these phenotypes (FIGS. 5a,b). In fact, SA-β-catenin exhibited a comparable, if not better, rescue effect compared to that of wildtype human DISC1 cDNA (FIGS. 5a,b). This observation underscores a major role for DISC1 in regulating progenitor proliferation by fine-tuning β-catenin levels.

Figure 5C:
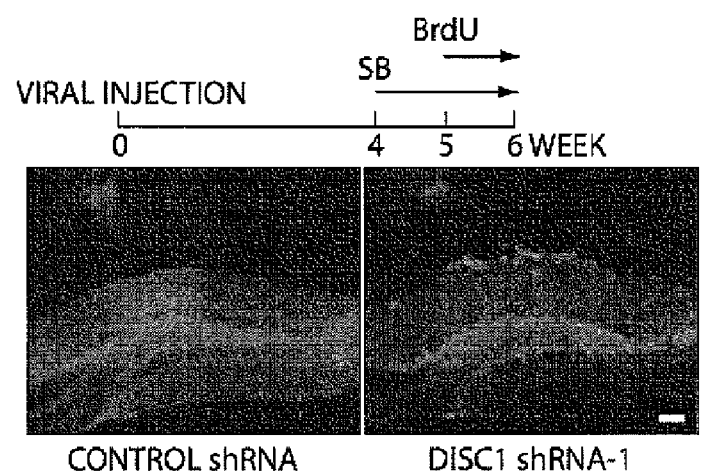
Figure 5D:
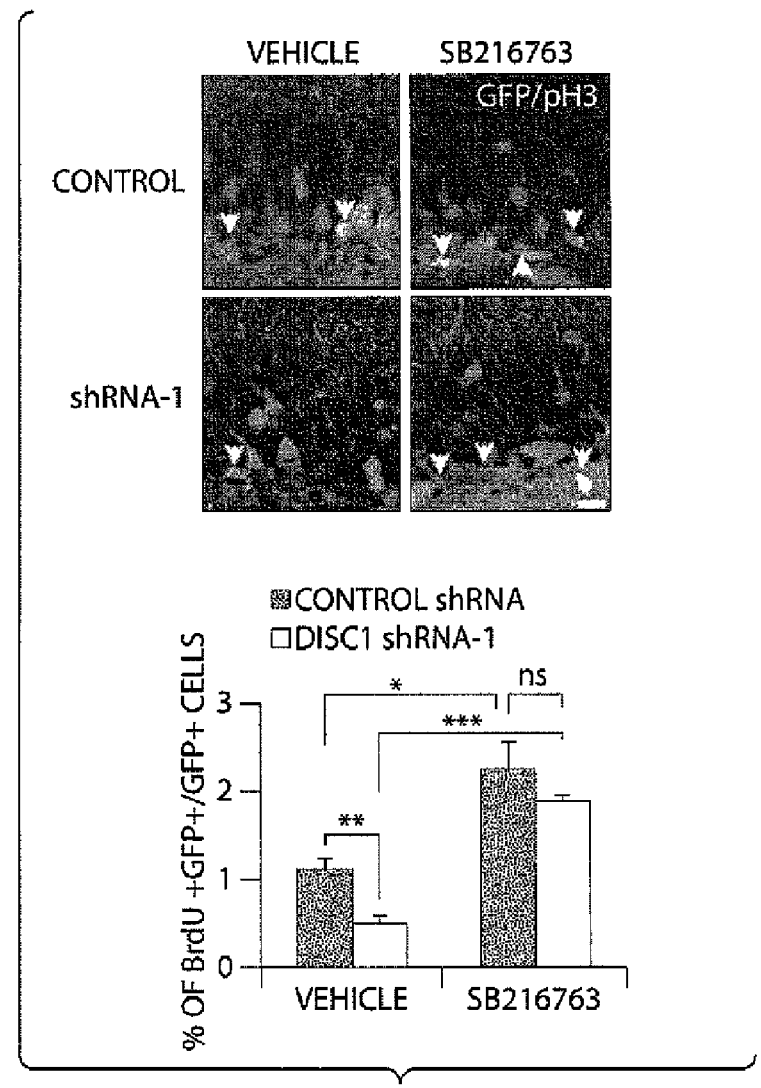
Figure 13A:
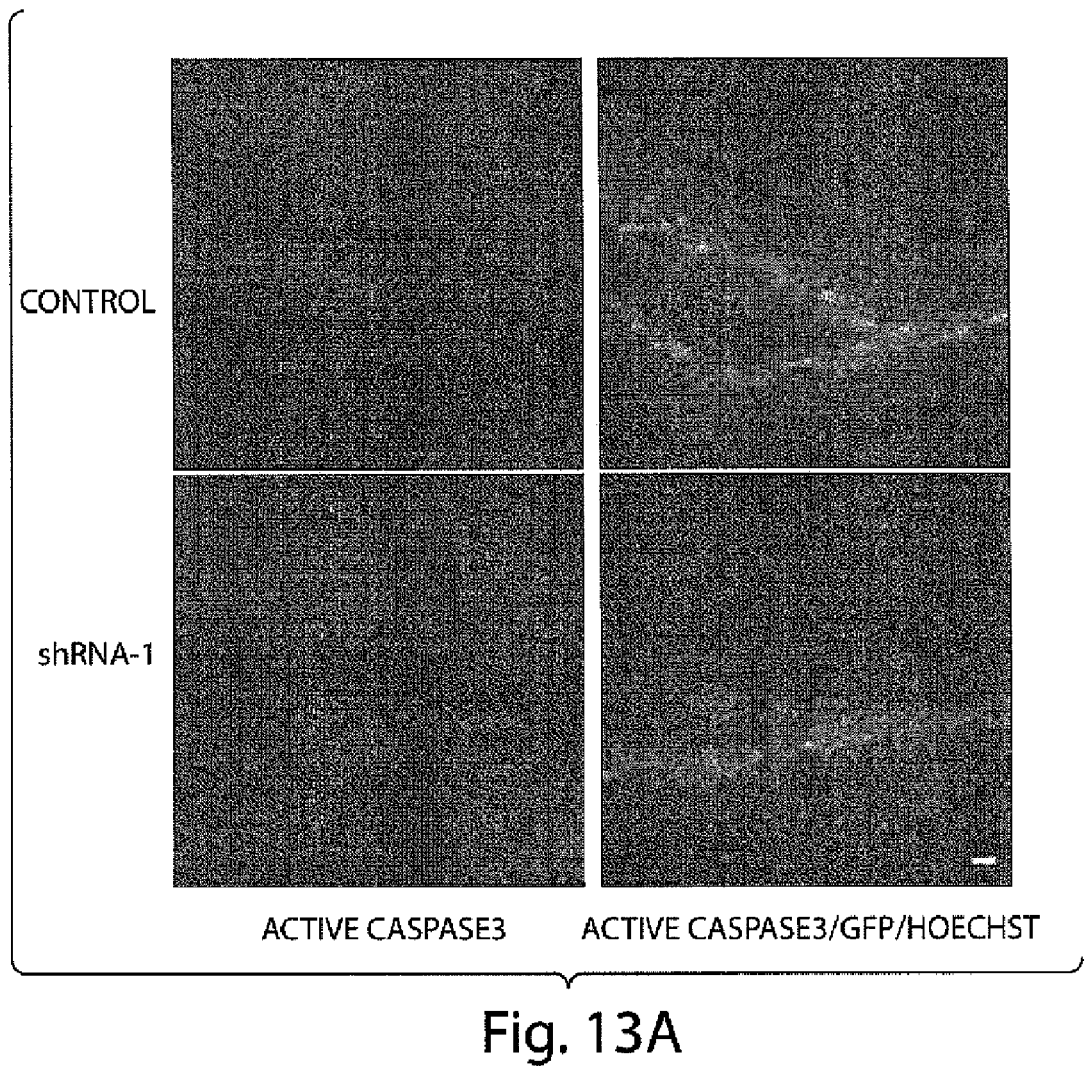
Figure 14A:
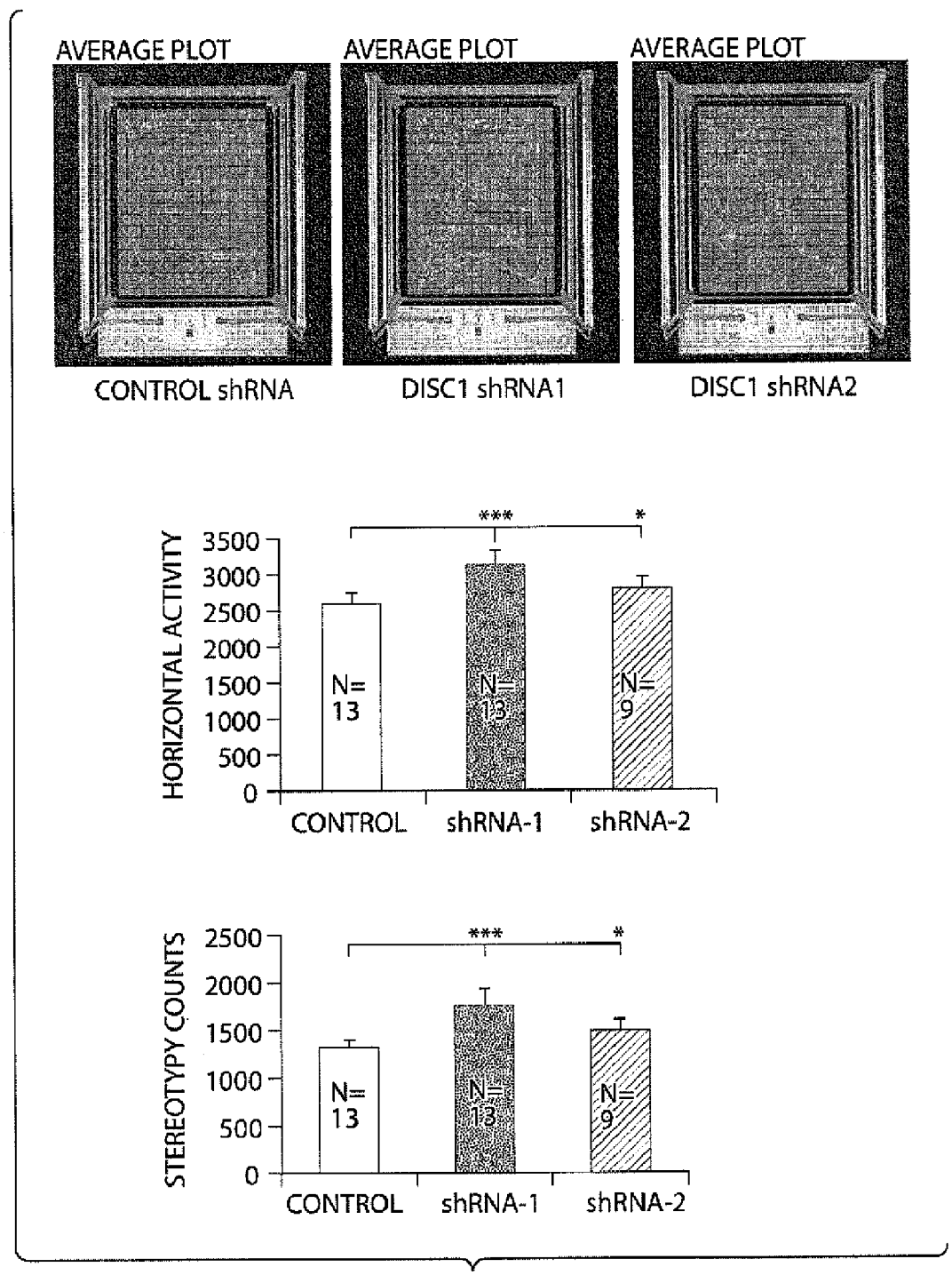
Figure 14B:
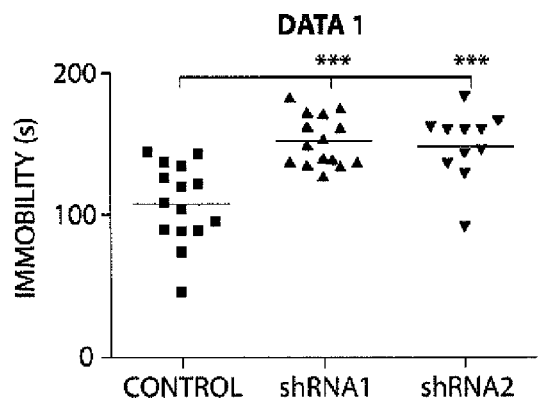
Figure 14C:
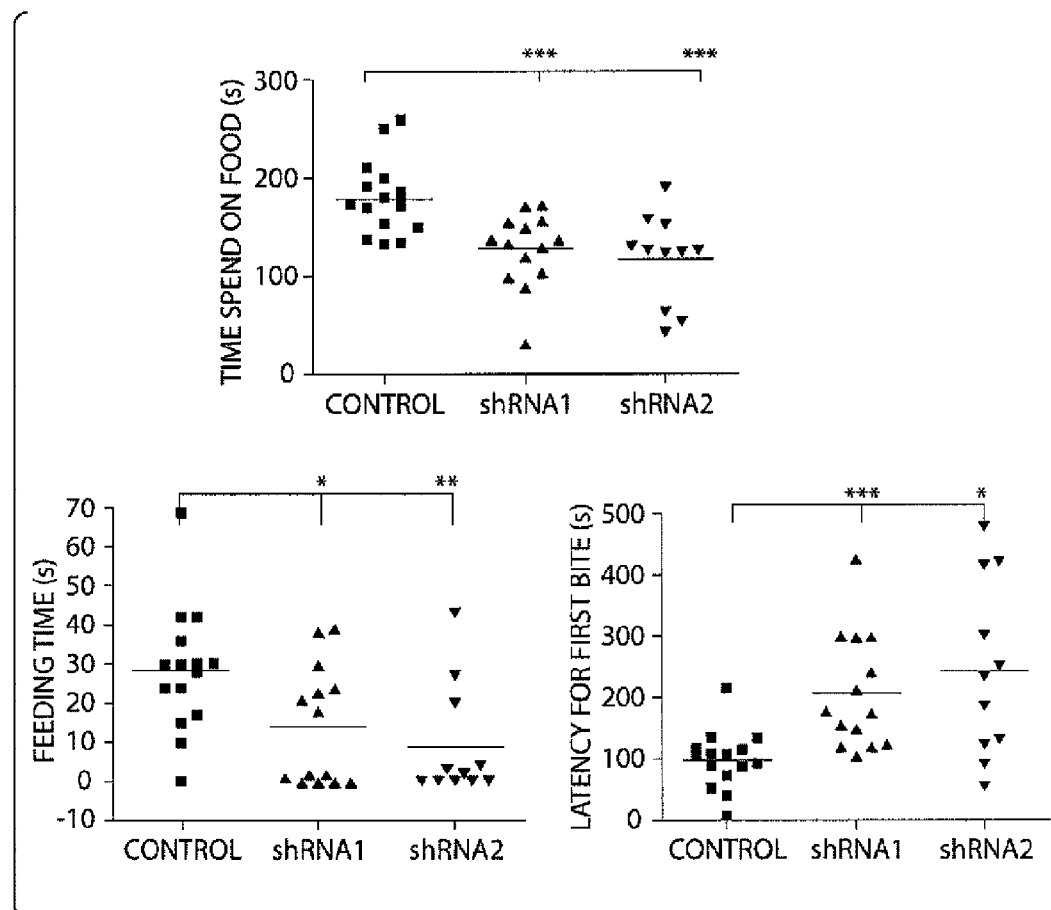
Figure 14D:
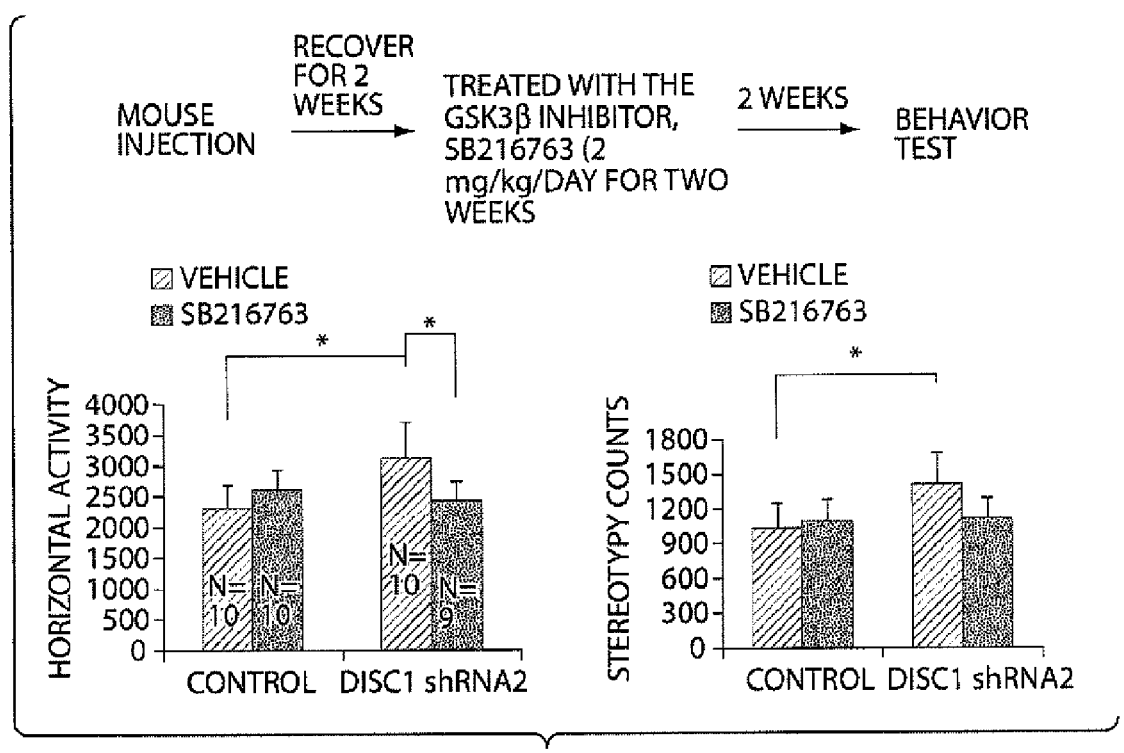

Since DISC1 is highly expressed in the adult dentate gyrus, we also investigated whether DISC1 plays a role in the proliferation of adult neural progenitors in vivo. We stereotactically injected control or DISC1 shRNA-1 lentivirus into the dentate gyrus of adult mouse brains. Five weeks later, we administered daily injections of BrdU over the course of 7 days (FIG. 5c). Lentivirus expressing control or DISC1 shRNA showed comparable infection rates in the subgranular zone of the dentate gyrus as revealed by the GFP signal (FIG. 5c). We observed a significant reduction in BrdU incorporation in DISC1 shRNA-1 cells compared to control shRNA cells, consistent with our observation in embryonic brains (FIG. 5d). The reduction of BrdU positive cells was not due to increased cell death, as there was no increase in active caspase 3 labeling in GFP positive cells in the dentate gyrus (FIG. 13a). To determine whether this effect is mediated through GSK3β activation as a consequence of DISC1 knockdown, vehicle or SB216763 (2 mg/kg) were administered to mice daily for 2 weeks (4 weeks after the administration of virus) (FIG. 5c). SB216763 has been previously reported to cross the blood-brain barrier (Selenica, M. L. et al. Efficacy of small-molecule glycogen synthase kinase-3 inhibitors in the postnatal rat model of tau hyperphosphorylation. Br J Pharmacol 152, 959-79 (2007)). Intriguingly, SB216763 treatment significantly increased the number of BrdU positive cells in mice infected with the control virus (FIG. 5d). In contrast, DISC1 shRNA-1 infected mice no longer exhibited a reduction in BrdU positive cells when treated with SB216763. Together, these results indicate that GSK3β plays a physiological role in regulation of progenitor proliferation in adult dentate gyrus and that the role of DISC1 in progenitor proliferation is mediated through the inhibition of GSK3β.

In summary, we demonstrated here that DISC1 is required for the proliferation of neural progenitors during embryonic brain development and in the adult dentate gyrus. This is a surprising result given that previous studies have focused on a role of DISC1 in postmitotic neurons (Duan, X. et al. Disrupted-In-Schizophrenia 1 regulates integration of newly generated neurons in the adult brain. Cell 130, 1146-58 (2007); Shinoda, T. et al. DISC1 regulates neurotrophin-induced axon elongation via interaction with Grb2. J Neurosci 27, 4-14 (2007)). We provided multiple lines of evidence supporting a role for DISC1 in regulating progenitor proliferation by modulating Wnt signaling. Specifically, DISC1 inhibits GSK3β activity, which in turn, positively influences the abundance of 3-catenin.

Example 7

DISC1 Inhibits GSK3β by Direct Physical Interaction

We found that two different domains of DISC1, spanning amino acids 1-220 and 356-595, directly associate with purified GSK3β in an in vitro binding assay. A recent report demonstrated that PDE4B also interacts with DISC1 through several distinct binding sites (Murdoch, H. et al. Isoform-selective susceptibility of DISC1/phosphodiesterase-4 complexes to dissociation by elevated intracellular cAMP levels. J Neurosci 27, 9513-24 (2007)). It is likely that the interaction of DISC1 with GSK3β directly impacts GSK3β catalytic activity, as fragment 195-238 of DISC1 inhibited the catalytic activity of recombinant GSK3β in an in vitro cell free system (FIG. 4h). Peptide 195-238 inhibited GSK3β in a dose-dependent manner more potently than the commercial peptide inhibitor, L803-MTS. Interestingly, although another peptide 40-78 is also evolutionally conserved from mouse to human, it did not inhibit GSK3β activity. At low concentrations (1 µM), peptide 195-238 did not inhibit GSK3β, wheras the DISC1 fragment 1-220 inhibited GSK3β at 0.5 µM, implying that multiple domains of DISC1 are involved in this inhibition. Prior to this study, peptides derived from FRAT1 (FRATide) (Thomas, G. M. et al. A GSK3-binding peptide from FRAT1 selectively inhibits the GSK3-catalysed phosphorylation of axin and beta-catenin. FEBS Lett 458, 247-51 (1999)) and axin (Hedgepeth, C. M., Deardorff, M. A., Rankin, K. & Klein, P. S. Regulation of glycogen synthase kinase 3beta and downstream Wnt signaling by axin. Mol Cell Biol 19, 7147-57 (1999)) were also shown to inhibit GSK3β activity. FRATide (Thomas, G. M. et al. A GSK3- binding peptide from FRAT1 selectively inhibits the GSK3-catalysed phosphorylation of axin and beta-catenin. FEBS Lett 458, 247-51 (1999)) inhibits GSK3β by binding to the C-terminal lobe of the kinase domain (Bax, B. et al. The structure of phosphorylated GSK-3beta complexed with a peptide, FRATtide, that inhibits beta-catenin phosphorylation. Structure 9, 1143-52 (2001)).

Example 8

DISC1 Regulates Neural Progenitor Proliferation by Modulating GSK3β/β-Catenin Signaling A major function of GSK3β is to regulate β-catenin stability upon activation of the canonical Wnt signaling pathway (Logan, C. Y. & Nusse, R. The Wnt signaling pathway in development and disease. Annu Rev Cell Dev Biol 20, 781-810 (2004)). β-catenin deficiency in the developing brain leads to depletion of nestin-positive neural progenitors in the ventricular zone (Zechner, D. et al. beta-Catenin signals regulate cell growth and the balance between progenitor cell expansion and differentiation in the nervous system. Dev Biol 258, 406-18 (2003)), whereas overexpression of stabilized β-catenin induces massive expansion of neural progenitors and enlarged brains (Chem, A. & Walsh, C. A. Regulation of cerebral cortical size by control of cell cycle exit in neural precursors. Science 297, 365-9 (2002)), indicating that β-catenin is critically involved in determining the fate of neural progenitors. Several lines of evidence imply that DISC1 controls neural progenitor fate by modulating β-catenin abundance. First, we observed a direct interaction between DISC1 and GSK3p. Second, luciferase reporter assays performed after in utero electroporation of TOP-FLASH and DISC1 shRNA or human DISC1 cDNA constructs revealed that DISC1 loss-of-function blunted TCF reporter activity, whereas DISC1 gain-of-function potentiated TCF reporter activity. This result indicates that DISC1 modulates Wnt signaling in the developing brain. Importantly, neural progenitor proliferation defects caused by DISC1 loss-of-function could be readily overcome by co-expression of the stable β-catenin mutant. This underscores the notion that regulation of β-catenin abundance is the primary mechanism linking DISC1 to neural progenitor proliferation. Similarly, the progenitor proliferation defect caused by DISC1 shRNA in the adult dentate gyrus was reversed by treating mice with a GSK3β-specific chemical inhibitor. Taken together, these observations provide compelling evidence for the integral role of DISC1 in modulating GSK3p/β-catenin signaling and neural progenitor proliferation.

Example 9

The Implication of DISC1/GSK3β/β-Catenin Interaction in Neural Psychiatric Disorders GSK3β is involved in several signaling pathways implicated in schizophrenia. It is a downstream mediator of dopamine signaling via the Dopamine D2 receptor/β-arrestin 2/phosphatase 2A complex (Beaulieu, J. M. et al. An Akti-beta-arrestin 2/PP2A signaling complex mediates dopaminergic neurotransmission and behavior. Cell 122, 261-73 (2005)). Dopamine D2 receptor is a target of many antipsychotic drugs (Seeman, P. Targeting the dopamine D2 receptor in schizophrenia. Expert Opin Ther Targets 10, 515-31 (2006)). Likewise, Neuregulin-1 signaling via Akt, both risk genes for schizophrenia (Ross, C. A., Margolis, R. L., Reading, S. A., Pletnikov, M. & Coyle, J. T. Neurobiology of schizophrenia. Neuron 52, 139-53 (2006)), regulates GSK3 activity. Furthermore, our observation that SA-β-catenin and specific GSK3β inhibitors can override the negative effects of DISC1 loss-of-function on cell proliferation in vitro and in vivo also imply that GSK3 is a target for therapeutic intervention. Indeed, it was shown previously that genetic or pharmacological inhibition of GSK3 reduced amphetamine induced hyperactivity in mice (Beaulieu, J. M. et al. Lithium antagonizes dopamine-dependent behaviors mediated by an AKT/glycogen synthase kinase 3 signaling cascade. Proc Natl Acad Sci USA 101, 5099-104 (2004)).

Alterations in neurogenesis are implicated in the development of depression and other abnormal behaviors. To examine the behavioral consequences of disrupting the DICS1/GSK3β pathway, we silenced DISC1 expression in the adult dentate gyrus and evaluated behavioral consequences. Four weeks after the injection of control or DISC1 shRNA-1 lentivirus, mice were treated with vehicle or SB-216763 (2 mg/kg i.p.) every other day for 10 days. Compared to control mice, DISC1 shRNA injected mice exhibited hyperlocomotion in response to novelty, which is considered a model of symptoms of schizophrenia. DISC1 shRNA injected mice traveled a greater distance and spent more time moving in a novel open field than control mice (FIG. 17A). These behaviors were normalized by SB-216763 treatment. We further tested whether DISC1 loss-of-function had consequences on depression-like behavior in the forced swim test. DISC1 shRNA infected mice displayed greater immobility (FIG. 17B), an indicator of depressive behavior, which was also suppressed by SB-216763. Importantly, swimming velocity was unchanged. DISC1 shRNA infected mice did not display increased anxiety, as there was no difference in time spent in the closed arms versus the aversive open arms in the elevated plus-maze (FIG. 17C). Thus, increased GSK3β activity caused by DISC1 loss-of-function is associated with schizophrenia- and depression-like behaviors.

Example 10

Evaluation of the Activity of DISC1 Human Variants on Inhibition of GSK3 and Wnt Signaling The effects of hDISC1 variants on Wnt-induced TCF-LEF reporter activity were examined. The results are shown in FIG. 19A. The common R264Q variant, but not the rare S24R variant, was unable to potentiate Wnt-induced TCF-LEF luciferase reporter activity compared to WT-hDISC1 in vitro. The effects of hDISC1 variants on cell positioning in the developing neocortex after in utero electroporation were also examined. The results are shown in FIG. 19B. Overexpression of WT-hDISC1 or the S24R rare variant in utero causes an increased number of GFP-positive cells in the ventricular (VZ)/sub-ventricular zones (SVZ) compared to overexpression of GFP alone. However, overexpression of the R264Q common variant causes a depletion of GFP-positive cells from the VZ/SVZ and a corresponding increase in the number of cells in the cortical plate (CP), suggesting premature differentiation of neural progenitor cells.

It is shown herein that some human DISC1 variants display markedly reduced potentiation of TCF/LEF activity. These results suggest that compromised Wnt pathway caused by human DISC1 variants contributes to the pathophysiology of schizophrenia.

Example 11

DISC1 is Required for AKT Activation

Figure 20A:
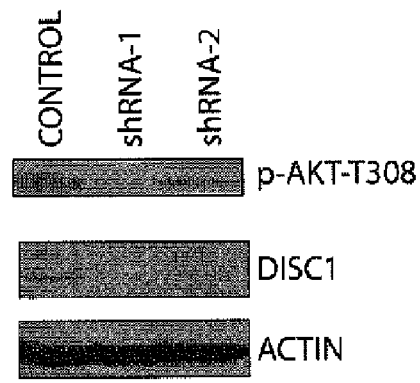
Figure 20B:
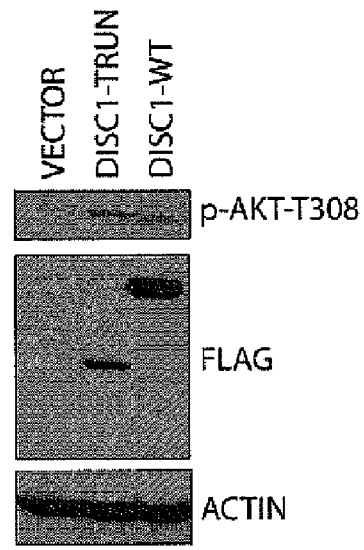
Figure 20C:
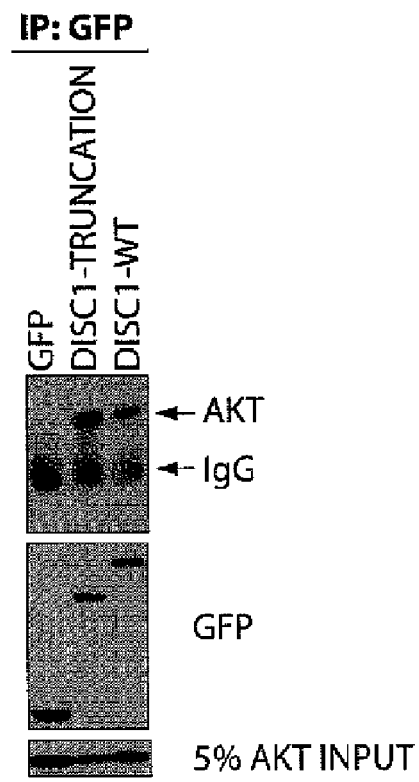

Our results show that DISC1 positive regulates AKT (FIG. 20). DISC1 loss of function reduced AKT T308 phosphorylation, a marker for active AKT (FIG. 20a). Conversely, over expression of DISC1 increased AKT T308 phosphorylation (FIG. 20b). Furthermore, DISC1 physically associates with AKT (FIG. 20c). The properties of DISC1, namely activation of AKT and inhibition of GSK3β, draw striking parallels with those of lithium.

Example 12

Discovery of Small-Molecule Probes of Human DISC1 Isoforms

Figure 21A:
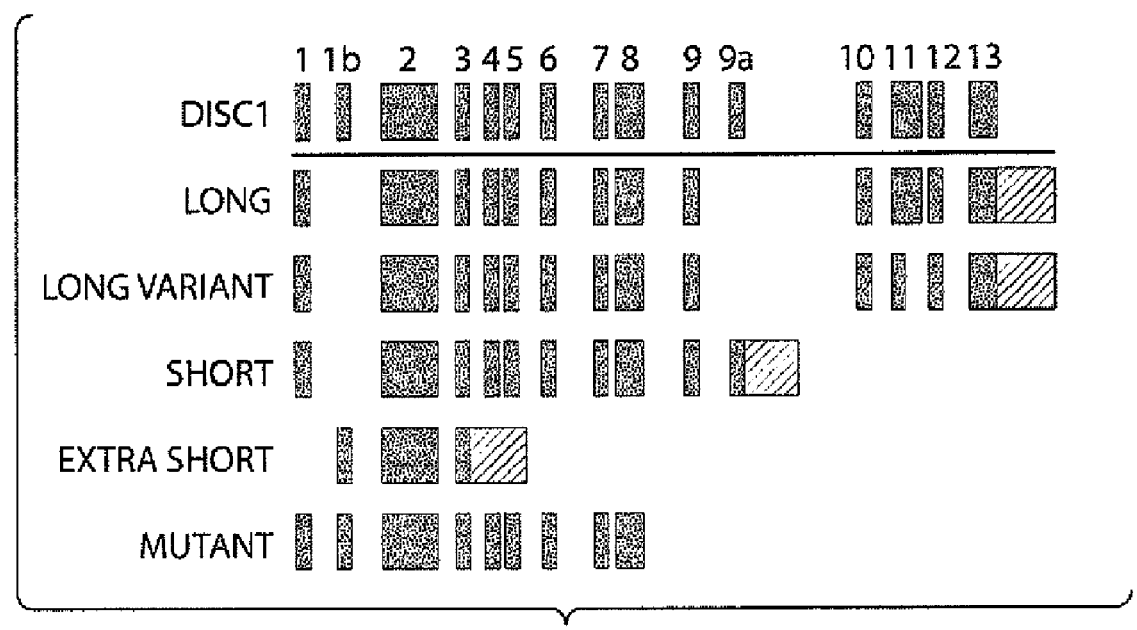

Small-molecule microarrays (SMMs) were used to identify small molecules that bind to DISC1 and its different isoforms (FIG. 21A). Several DISC1 variants (Long, Short, Extra Short, Mutant, Long Variant) were expressed in tissue culture cells, and we have confirmed that they are expressed and are full length. We have identified small molecules that specifically bind to these variants. These small molecules can be used as chemical probes to better understand how the DISC1 effecter pathways are regulated.

Methods. To express the above DISC1 splice variants in tissue culture cells, lentiviral constructs were constructed for each of the 4 major DISC1 isoforms (Long (L), Long variant (LV), Short (S), or Extra short (Es)) known at the time, as well as the truncated mutant form (Mutant (M)) corresponding to the disease associated variant. Subsequently, stable HEK-293 cell lines expressing these proteins were derived.

Figure 21B:
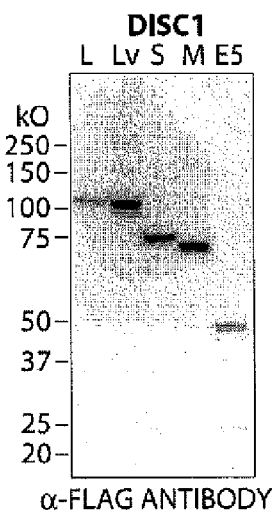

To verify expression of the DISC1 isoforms, HEK-293 cells stably expressing DISC1 variants were fixed and stained with an anti-FLAG epitope antibody. Whole cell lysates were isolated from cells stably expressing the Long (L), Long variant (LV), Short (S), Mutant (M) or Extra short (Es) variant of FLAG-DISC1. A sample of each lysate was run on a polyacrylamide gel and a western blot was performed (FIG. 21B). Western blots were probed with an anti-FLAG antibody. Molecular weight markers are shown at the left of the western blot. All of the proteins are expressed and appear to be full length.

Results. Using SMM screening technology and an array of ~10,000 small molecules, which included FDA approved drugs, CNS active compounds, and novel synthetic compounds from the Broad Institute's Chemical Biology platform, 65 compounds were selected as "hits" for three out of the five DISC1 variants. Some of these "hits" can be grouped together, such as the examples below in FIG. 22A. There were 10 compounds that were selected as "hits" for four out of the five DISC1 variants. Some examples of chemical structure are shown below in FIG. 22B. There were only two compounds that were selected as "hits" for all five DISC1 variants. Their chemical structures are shown below in FIG. 22C.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims.

We claim:

1. A composition comprising a DISC1 pathway activator, and optionally comprising a linker molecule, a detectable moiety, a fatty acid, or a heterologous protein sequence, and a carrier, wherein the DISC1 pathway activator is a DISC1 fragment selected from human DISC1 peptide 2 consisting of SEQ ID NO: 8, mouse DISC1 peptide 2 consisting of SEQ ID NO: 2, human DISC1 peptide 3 consisting of SEQ ID NO: 9 and mouse DISC1 peptide 3 consisting of SEQ ID NO: 10.

2. The composition of claim 1, wherein the DISC1 fragment is human or mouse DISC1 peptide 2.

3. The composition of claim 1, wherein the DISC1 fragment is human or mouse DISC1 peptide 3.

4. The composition of claim 1, wherein the composition is sterile.

5. The composition of claim 1, wherein the detectable moiety is biotin.

6. A polypeptide comprising a DISC1 fragment, and optionally comprising a linker molecule, a detectable moiety, a fatty acid, or a heterologous protein sequence, wherein the DISC1 fragment is selected from the group consisting of human DISC1 peptide 2 consisting of SEQ ID NO: 8, mouse DISC1 peptide 2 consisting of SEQ ID NO: 2, human DISC1 peptide 3 consisting of SEQ ID NO: 9 and mouse DISC1 peptide 3 consisting of SEQ ID NO: 10.

7. The polypeptide of claim 6, wherein the detectable moiety is biotin.

8. A method comprising,
contacting the DISC1 fragment polypeptide of claim 6 with a GSK3β molecule, in the presence and in the absence of a putative modulator;
detecting binding between said DISC1 fragment polypeptide and the GSK3β molecule in the presence and absence of the putative modulator; and
identifying a modulator based on a decrease or increase in binding between the DISC1 fragment polypeptide and the GSK3β molecule in the presence of the putative modulator, as compared to binding in the absence of the putative modulator.

9. A method for identifying a DISC1 modulator comprising,
incubating a cell expressing the DISC1 fragment polypeptide of claim 6 in the presence and in the absence of a putative modulator;
detecting GSK3β activity in the presence and absence of the putative modulator; and
identifying a DISC1 modulator based on a decrease or increase in the GSK3β activity in the presence of the putative modulator, as compared to the activity in the absence of the putative modulator.

* * * * *